United States Patent
McDonald et al.

(10) Patent No.: US 10,981,893 B2
(45) Date of Patent: Apr. 20, 2021

(54) THERAPEUTIC INHIBITORY COMPOUNDS

(71) Applicant: Attune Pharmaceuticals, Inc., New York, NY (US)

(72) Inventors: Andrew McDonald, New York, NY (US); Shawn Qian, New York, NY (US)

(73) Assignee: ATTUNE PHARMACEUTICALS, INC., New York, NY (US)

( * ) Notice: Subject to any disclaimer, the term of this patent is extended or adjusted under 35 U.S.C. 154(b) by 0 days.

(21) Appl. No.: 15/741,191

(22) PCT Filed: Jun. 30, 2016

(86) PCT No.: PCT/IB2016/001053
§ 371 (c)(1),
(2) Date: Dec. 29, 2017

(87) PCT Pub. No.: WO2017/001926
PCT Pub. Date: Jan. 5, 2017

(65) Prior Publication Data
US 2019/0263783 A1 Aug. 29, 2019

Related U.S. Application Data

(60) Provisional application No. 62/187,475, filed on Jul. 1, 2015.

(51) Int. Cl.
| | | |
|---|---|---|
| *C07D 401/14* | (2006.01) | |
| *C07D 471/04* | (2006.01) | |
| *A61K 31/437* | (2006.01) | |
| *A61K 31/506* | (2006.01) | |
| *A61P 7/10* | (2006.01) | |
| *C07D 401/12* | (2006.01) | |
| *C07D 401/10* | (2006.01) | |
| *C07D 413/14* | (2006.01) | |
| *A61P 37/06* | (2006.01) | |
| *A61P 17/00* | (2006.01) | |

(52) U.S. Cl.
CPC ............. *C07D 401/14* (2013.01); *A61P 7/10* (2018.01); *A61P 17/00* (2018.01); *A61P 37/06* (2018.01); *C07D 401/10* (2013.01); *C07D 401/12* (2013.01); *C07D 413/14* (2013.01); *C07D 471/04* (2013.01)

(58) Field of Classification Search
CPC ............................ C07D 401/14; C07D 471/04
See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 7,459,452 B2 * | 12/2008 | Di Francesco .... C07D 239/557 514/235.8 |
| 2008/0182849 A1 | 7/2008 | Currie et al. |
| 2010/0056527 A1 | 3/2010 | Eatherton et al. |
| 2011/0065757 A1 | 3/2011 | Aiello et al. |
| 2012/0053165 A1 | 3/2012 | Allen et al. |

FOREIGN PATENT DOCUMENTS

| | | |
|---|---|---|
| WO | WO-03035076 A1 | 5/2003 |
| WO | WO-2015022546 A1 | 2/2015 |
| WO | WO-2017001926 A2 | 1/2017 |

OTHER PUBLICATIONS

Berge et al. Pharmaceutical Salts. Journal of Pharmaceutical Sciences 66(1):1-19 (Jan. 1977).
Bork et al. Treatment of 193 episodes of laryngeal edema with Cl inhibitor concentrate in patients with hereditary angioedema. Arch. Intern. Med. 161:714-718 (2001).
Bork et al. Treatment with C1 inhibitor concentrate in abdominal pain attacks of patients with hereditary angioedema. Transfusion 45:1774-1784 (2005).
Bundgaard et al. Design of Prodrugs pp. 7-9, 21-24 (1985).
Colman et al. Effect of cleavage of the heavy chain of human plasma kallikrein on its functional properties. Blood 65:311-318 (1985).
Cool. Characterization of the human blood coagulation factor XII gene. Intron/exon gene organization and analysis of the 5'-flanking region. The Journal of Biological Chemistry 262(28):13662-13673 (1987).
Cugno et al. C1-inhibitor deficiency and angioedema: molecular mechanisms and clinical progress. Trends Mol. Med. 15(2):69-78 (2009).
Cugno et al. Generation of plasmin during acute attacks of hereditary angioedema. The Journal of Laboratory and Clinical Medicine 121(1):38—43 (1993).
Evans. Synthesis of radiolabeled compounds. J Radioanal Chem 64(1-2):9-32 (1981).

(Continued)

*Primary Examiner* — Emily A Bernhardt
(74) *Attorney, Agent, or Firm* — Wilson Sonsini Goodrich & Rosati

(57) ABSTRACT

Provided herein are heterocyclic derivative compounds of Formula (I) and pharmaceutical compositions comprising said compounds. The compounds of Formula (I) are useful for inhibiting plasma kallikrein. Furthermore, the disclosed compounds and compositions are useful for the treatment of diseases wherein the inhibition of plasma kallikrein inhibition has been implicated, such as angioedema and the like.

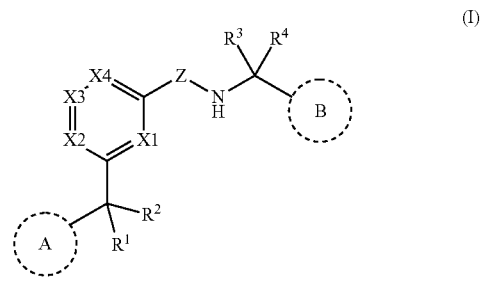

(I)

2 Claims, No Drawings

(56) References Cited

OTHER PUBLICATIONS

Gao et al. Extracellular carbonic anhydrase mediates hemorrhagic retinal and cerebral vascular permeability through prekallikrein activation. Nat Med 13(2):181-188 (2007).
Kabalka et al. The Synthesis of radiolabeled compounds via organometallic intermediates. Tetrahedron Report No. 263 45(21):6601-6621 (1989).
Kaplan et al. Angioedema. J. Am. Acad. Dermatol. 53(3):373-388 (2005).
Kaplan et al. The intrinsic coagulation/kinin-forming cascade: assembly in plasma and cell surfaces in inflammation. Advances in Immunology 66:225-272 (1997).
Liu et al. Plasma kallikrein-kinin system and diabetic retinopathy. Biol Chem 394(3):319-328 (2013).
Liu et al. TGFβ signaling induces expression of Gadd45b in retinal ganglion cells. Invest. Ophthalmol. Vis. Sci. 54(2):1061-1069 (2013).
Mehta et al. Signaling mechanisms regulating endothelial permeability. Physiol. Rev. 86(1):279-367 (2006).
Muller et al. Novel roles for factor XII-driven plasma contact activation system. Curr. Opin. Hematol. 15:516-521 (2008).
NY et al. The structure of the human tissue-type plasminogen activator gene: correlation of intron and exon structures to functional and structural domains. PNAS USA 81(17):5355-5359 (1984).
PCT/IB2016/001053 International Search Report and Written Opinion dated Jan. 25, 2017.
Phipps et al. Plasma kallikrein mediates angiotensin II type 1 receptor-stimulated retinal vascular permeability. Hypertension 53:175-181 (2009).
Pixley et al. The regulation of human factor XIIa by plasma proteinase inhibitors. The Journal of Biological Chemistry 260(3):1723-1729 (1985).
Sandoval et al. Ca(2+) signalling and PKCalpha activate increased endothelial permeability by disassembly of VE-cadherin junctions. J. Physiol. 533(pt 2):433-445 (2001).
Schapira et al. Protection of human plasma kallikrein from inactivation by C1 inhibitor and other protease inhibitors. The role of high molecular weight kininogen. Biochemistry 20:2738-2743 (1981).
Stavrou. Factor XII: what does it contribute to our understanding of the physiology and pathophysiology of hemostasis & thrombosis. Thrombosis Research 125(3):210-215 (2010).
Storini et al. Selective Inhibition of Plasma Kallikrein Protects brain from Reperfusion Injury. JPET 381:849-954 (2006).
Stahl et al. Handbook of Pharmaceutical Salts. Verlag Helvetica Chimica Acta, Zurich, 2002.

\* cited by examiner

THERAPEUTIC INHIBITORY COMPOUNDS

CROSS REFERENCE

This application is the U.S. National Phase application of International Application No. PCT/IB2016/001053, filed Jun. 30, 2016; and claims the benefit of U.S. Provisional Application No. 62/187,475, filed Jul. 1, 2015, all of which are incorporated by reference herein in their entirety.

BACKGROUND

A need exists in the medicinal arts for the effective treatment of diseases and disorders related to the vascular system. Such diseases and disorders include, but are not limited to, angioedema, macular edema and brain edema.

BRIEF SUMMARY OF THE INVENTION

Provided herein are heterocyclic derivative compounds and pharmaceutical compositions comprising said compounds. The subject compounds and compositions are useful for inhibiting plasma kallikrein.

One embodiment provides the compound, or a pharmaceutically acceptable salt thereof, having the structure of Formula (I):

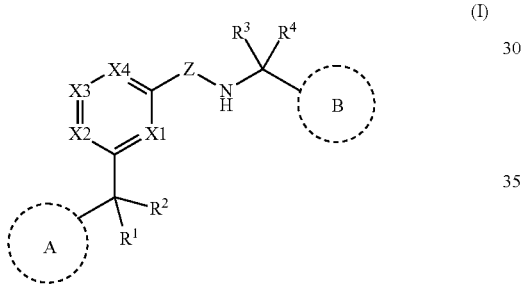

wherein,

Z is C=O, SO$_2$, C=NH, C=N(CN), or C=N—(C1-C3 alkyl);

Ring A is an optionally substituted bicyclic heterocyclic ring;

Ring B is a optionally substituted monocyclic heterocyclic ring or optionally substituted bicyclic heterocyclic ring;

X1 is N or C—R$^{11}$;
X2 is N or C—R$^{12}$;
X3 is N or C—R$^{13}$;
X4 is N or C—R$^{14}$; with the provision that at least two of X1, X2, X3 or X4 is N;

each R$^{11}$, R$^{12}$, R$^{13}$, or R$^{14}$ is independently selected from hydrogen, cyano, halo, hydroxy, azido, amino, nitro, —CO$_2$H, —S(O)—R$^{20}$, —S—R$^{20}$, —S(O)$_2$—R$^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—R$^{20}$, —CO$_2$—R$^{20}$, —CO(NR$^{21}$)$_2$, —SO$_2$(NR$^{21}$)$_2$, —C(=NR$^{22}$)—(NR$^{21}$)$_2$, or optionally substituted alkynyl;

each R$^1$ or R$^2$ is independently selected from hydrogen, halo, hydroxy, amino, —CO$_2$H, —S(O)—R$^{20}$, —S—R$^{20}$, —S(O)$_2$—R$^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—R$^{20}$, —CO$_2$—R$^{20}$, —CO(NR$^{21}$)$_2$, —SO$_2$(NR$^{21}$)$_2$, —C(=NR$^{22}$)—(NR$^{21}$)$_2$, or optionally substituted alkynyl; or optionally, R$^1$ and R$^2$ are optionally substituted C1-C5 alkyl and join to form a ring; or optionally, R$^1$ and R$^2$ together form an oxo;

each R$^3$ or R$^4$ is independently selected from hydrogen, —CO$_2$H, optionally substituted alkyl, optionally substituted cycloalkyl, optionally substituted alkenyl, optionally substituted aryl, optionally substituted heteroaryl, optionally substituted heterocyclyl, —CO—R$^{20}$, —CO$_2$—R$^{20}$, —CO(NR$^{21}$)$_2$, —SO$_2$(NR$^{21}$)$_2$, —C(=NR$^{22}$)—(NR$^{21}$)$_2$, or optionally substituted alkynyl; or optionally, R$^3$ and R$^4$ are optionally substituted C1-C5 alkyl and join to form a ring;

each R$^{20}$ is selected from optionally substituted alkyl, optionally substituted cycloalkyl, optionally substituted aryl, optionally substituted heteroaryl, or optionally substituted heterocyclyl;

each R$^{21}$ is selected from hydrogen, optionally substituted alkyl, optionally substituted cycloalkyl, optionally substituted aryl, optionally substituted heteroaryl, or optionally substituted heterocyclyl; and each R$^{22}$ is selected from hydrogen, —CN, optionally substituted alkyl, optionally substituted cycloalkyl, optionally substituted aryl, optionally substituted heteroaryl, or optionally substituted heterocyclyl.

One embodiment provides the compound, or a pharmaceutically acceptable salt thereof, having the structure of Formula (II):

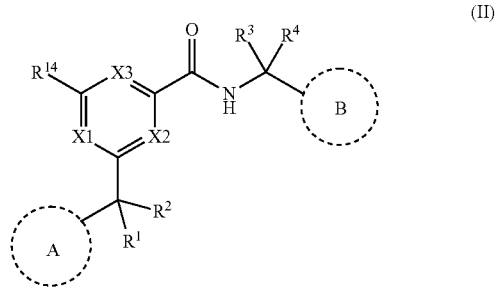

wherein,

Ring A is an optionally substituted bicyclic heterocyclic ring;

Ring B is a optionally substituted monocyclic heterocyclic ring or optionally substituted bicyclic heterocyclic ring;

X1 is C—R$^{11}$;
X2 is N or C—R$^{12}$
X3 is N or C—R$^{13}$; with the provision that only one of X2 or X3 is N;

each R$^{11}$, R$^{12}$, R$^{13}$, or R$^{14}$ is independently selected from hydrogen, cyano, halo, hydroxy, azido, amino, nitro, —CO$_2$H, —S(O)—R$^{20}$, —S—R$^{20}$, —S(O)$_2$—R$^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —CO(NR$^{21}$)$_2$, —SO$_2$(NR$^{21}$)$_2$, —C(=NR$^{22}$)—(NR$^{21}$)$_2$, or optionally substituted alkynyl;

each $R^1$ or $R^2$ is independently selected from hydrogen, halo, hydroxy, amino, —$CO_2$H, —S(O)—$R^{20}$, —S—$R^{20}$, —S(O)$_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —CO(NR$^{21}$)$_2$, —SO$_2$(NR$^{21}$)$_2$, —C(=NR$^{22}$)—(NR$^{21}$)$_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2$H, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —CO(NR$^{21}$)$_2$, —SO$_2$(NR$^{21}$)$_2$, —C(=NR$^{22}$)—(NR$^{21}$)$_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl;

each $R^{22}$ is selected from hydrogen, —CN, optionally substituted alkyl, optionally substituted cycloalkyl, optionally substituted aryl, optionally substituted heteroaryl, or optionally substituted heterocyclyl.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (II), or a pharmaceutically acceptable salt thereof, and a pharmaceutically acceptable excipient.

One embodiment provides a method of inhibiting kallikrein enzyme comprising contacting the kallikrein enzyme with a compound of Formula (I). One embodiment provides a method of inhibiting kallikrein enzyme comprising contacting the kallikrein enzyme with a compound of Formula (II).

One embodiment provides a method for treating angioedema in a patient in need thereof comprising administration to the patient a composition comprising a compound of Formula (I), or a pharmaceutically acceptable salt thereof. One embodiment provides a method for treating angioedema in a patient in need thereof comprising administration to the patient a composition comprising a compound of Formula (II), or a pharmaceutically acceptable salt thereof.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O— alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—R—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

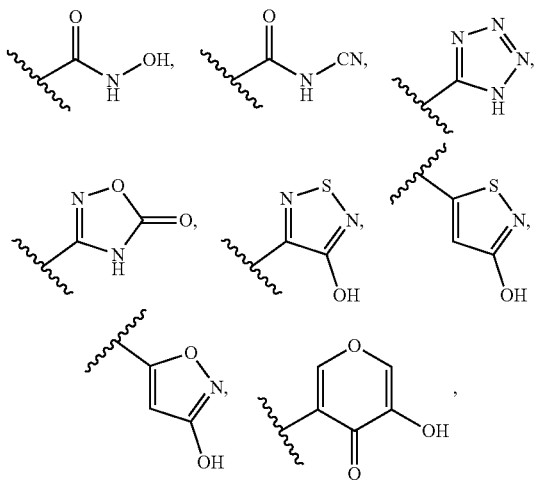

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) in-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

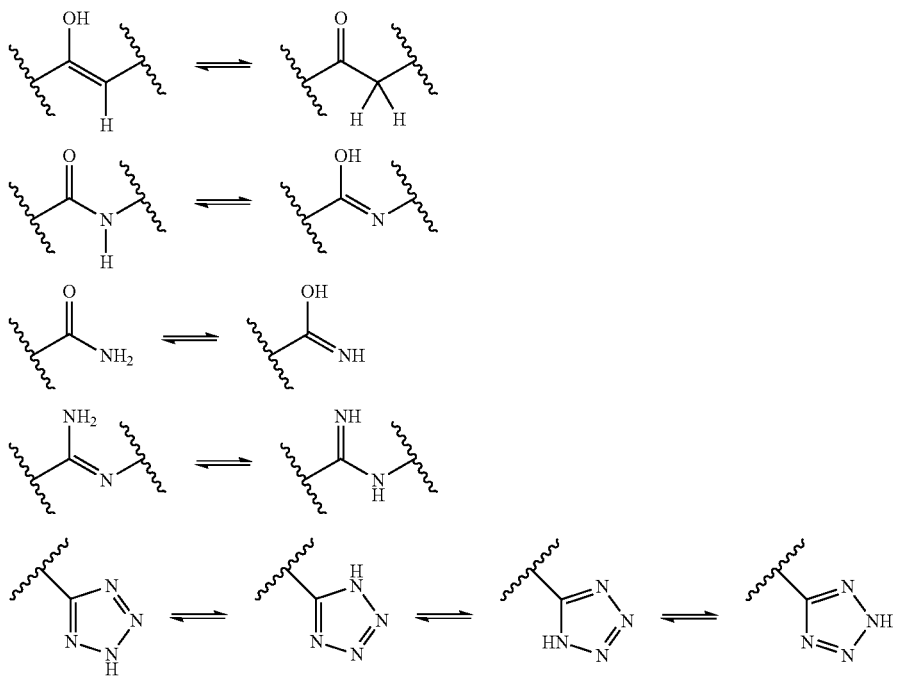

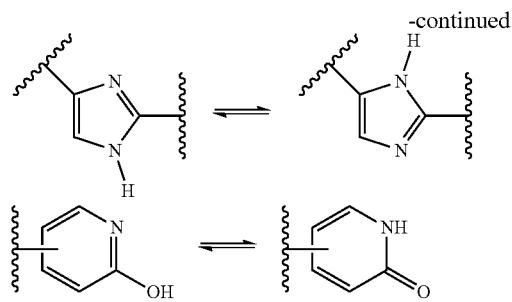

The compounds disclosed herein, in some embodiments, be used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-d₃ (CD₃I), are readily available and may be employed to transfer a deuterium-substituted carbon atom under nucleophilic substitution reaction conditions to the reaction substrate. The use of CD₃I is illustrated, by way of example only, in the reaction schemes below.

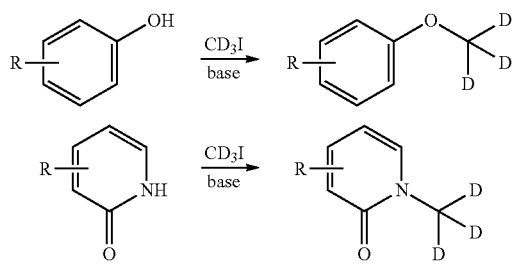

Deuterium-transfer reagents, such as lithium aluminum deuteride (LiAlD₄), are employed to transfer deuterium under reducing conditions to the reaction substrate. The use of LiAlD₄ is illustrated, by way of example only, in the reaction schemes below.

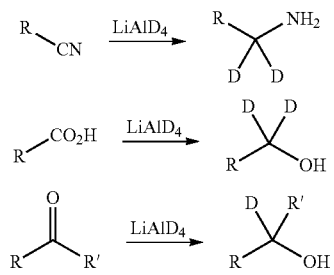

Deuterium gas and palladium catalyst are employed to reduce unsaturated carbon-carbon linkages and to perform a reductive substitution of aryl carbon-halogen bonds as illustrated, by way of example only, in the reaction schemes below.

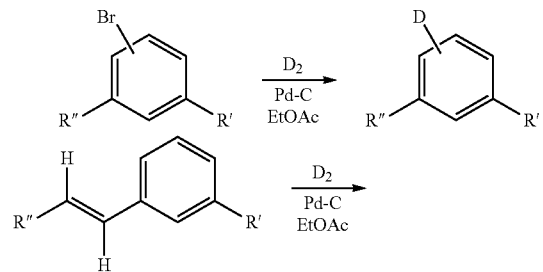

-continued

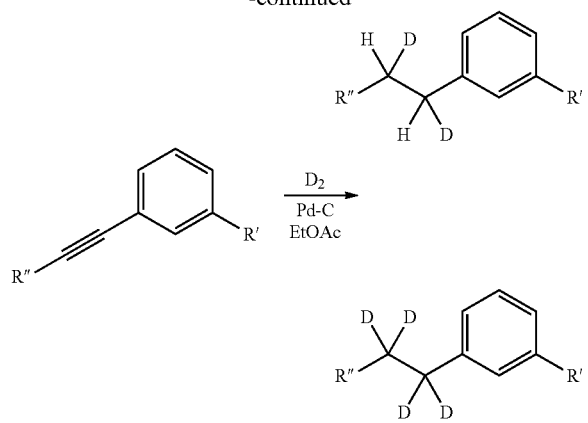

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the kallikrein inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Kallikrein Inhibitory Compounds

Provided herein are heterocyclic derivative compounds and pharmaceutical compositions comprising said compounds. The subject compounds and compositions are useful for inhibiting plasma kallikrein.

One embodiment provides the compound, or a pharmaceutically acceptable salt thereof, having the structure of Formula (I):

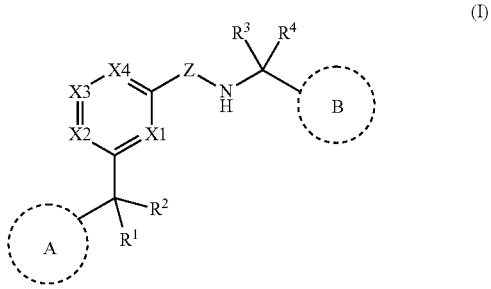

wherein,

Z is C=O, $SO_2$, C=NH, C=N(CN), or C=N—(C1-C3 alkyl);

Ring A is an optionally substituted bicyclic heterocyclic ring;

Ring B is a optionally substituted monocyclic heterocyclic ring or optionally substituted bicyclic heterocyclic ring;

X1 is N or C—$R^1$;

X2 is N or C—$R^2$;

X3 is N or C—$R^3$;

X4 is N or C—$R^{14}$; with the provision that at least two of X1, X2, X3 or X4 is N;

each $R^{11}$, $R^{12}$, $R^{13}$, or $R^{14}$ is independently selected from hydrogen, cyano, halo, hydroxy, azido, amino, nitro, —$CO_2H$, —S(O)—$R^{20}$, —S—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —CO($NR^{21}$)$_2$, —$SO_2$($NR^{21}$)$_2$, —C(=$NR^{22}$)—($NR^{21}$)$_2$, or optionally substituted alkynyl;

each $R^1$ or $R^2$ is independently selected from hydrogen, halo, hydroxy, amino, —$CO_2H$, —S(O)—$R^{20}$, —S—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —CO($NR^{21}$)$_2$, —$SO_2$($NR^{21}$)$_2$, —C(=$NR^{22}$)—($NR^{21}$)$_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —CO($NR^{21}$)$_2$, —$SO_2$($NR^{21}$)$_2$, —C(=$NR^{22}$)—($NR^{21}$)$_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl; and each $R^{22}$ is selected from hydrogen, —CN, optionally substituted alkyl, optionally substituted cycloalkyl, optionally substituted aryl, optionally substituted heteroaryl, or optionally substituted heterocyclyl.

Another embodiment provides the compound, or a pharmaceutically acceptable salt thereof, having the structure of Formula (I), wherein Z is C=O.

Another embodiment provides the compound, or a pharmaceutically acceptable salt thereof, having the structure of Formula (I), wherein X1 is N. Another embodiment provides the compound, or a pharmaceutically acceptable salt thereof, having the structure of Formula (I), wherein X2 is N. Another embodiment provides the compound, or a pharmaceutically acceptable salt thereof, having the structure of Formula (I), wherein X3 is N. Another embodiment provides the compound, or a pharmaceutically acceptable salt thereof, having the structure of Formula (I), wherein X4 is N. Another embodiment provides the compound, or a pharmaceutically acceptable salt thereof, having the structure of Formula (I), wherein only two of X1, X2, X3 or X4 is N. Another embodiment provides the compound, or a pharmaceutically acceptable salt thereof, having the structure of Formula (I), wherein only three of X1, X2, X3 or X4 is N.

Another embodiment provides the compound, or a pharmaceutically acceptable salt thereof, having the structure of Formula (I), wherein X1 is C—$R^{11}$. Another embodiment provides the compound, or a pharmaceutically acceptable salt thereof, having the structure of Formula (I), wherein X2 is C—$R^{12}$. Another embodiment provides the compound, or a pharmaceutically acceptable salt thereof, having the structure of Formula (I), wherein X3 is C—$R^{13}$. Another embodiment provides the compound, or a pharmaceutically acceptable salt thereof, having the structure of Formula (I), wherein X4 is C—$R^{14}$.

Another embodiment provides the compound, or a pharmaceutically acceptable salt thereof, having the structure of Formula (I), wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1 (2H)-on-2-yl; or optionally substituted quinolin-6-yl. Another embodiment provides the compound, or a pharmaceutically acceptable salt thereof, having the structure of Formula (I), wherein Ring A is an optionally substituted quinolin-6-yl. Another embodiment provides the compound, or a pharmaceutically acceptable salt thereof, having the structure of Formula (I), wherein the quinolin-6-yl is substituted with at least one substituent selected from optionally substituted C1-C3 alkyl, halogen, —CN, —SO₂Me, —SO₂NH₂, —CONH₂, —CH₂NHAc, —CO₂Me, —CO₂H, —CH₂OH, —CH₂NH₂, —NH₂, —OH, or OMe. Another embodiment provides the compound, or a pharmaceutically acceptable salt thereof, having the structure of Formula (I), wherein the quinolin-6-yl is substituted at least at the 3-position. Another embodiment provides the compound, or a pharmaceutically acceptable salt thereof, having the structure of Formula (I), wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl.

Another embodiment provides the compound, or a pharmaceutically acceptable salt thereof, having the structure of Formula (I), wherein Ring B is selected from an optionally substituted monocyclic heterocyclic ring. Another embodiment provides the compound, or a pharmaceutically acceptable salt thereof, having the structure of Formula (I), wherein the optionally substituted monocyclic heterocyclic ring is selected from optionally substituted imidazolyl, optionally substituted pyrazolyl, optionally substituted pyridinyl, optionally substituted pyridazinyl, optionally substituted pyrimidinyl, or optionally substituted pyrazinyl. Another embodiment provides the compound, or a pharmaceutically acceptable salt thereof, having the structure of Formula (I), wherein the optionally substituted monocyclic heterocyclic ring is an optionally substituted pyridinyl. Another embodiment provides the compound, or a pharmaceutically acceptable salt thereof, having the structure of Formula (I), wherein the optionally substituted pyridinyl is an optionally substituted aminopyridinyl. Another embodiment provides the compound, or a pharmaceutically acceptable salt thereof, having the structure of Formula (I), wherein the optionally substituted aminopyridinyl is an optionally substituted 6-aminopyridin-3-yl.

Another embodiment provides the compound, or a pharmaceutically acceptable salt thereof, having the structure of Formula (I), wherein Ring B is selected from an optionally substituted bicyclic heterocyclic ring. Another embodiment provides the compound, or a pharmaceutically acceptable salt thereof, having the structure of Formula (I), wherein the optionally substituted bicyclic heterocyclic ring is selected from optionally substituted quinolinyl, isoquinolinyl, quinazolinyl, indolyl, indazolyl, 1H-pyrrolo[2,3-b]pyridinyl, benzoxazolyl, benzoisoxazolyl, or benzimidazolyl. Another embodiment provides the compound, or a pharmaceutically acceptable salt thereof, having the structure of Formula (I), wherein the optionally substituted bicyclic heterocyclic ring is an optionally substituted indolyl. Another embodiment provides the compound, or a pharmaceutically acceptable salt thereof, having the structure of Formula (I), wherein the optionally substituted bicyclic heterocyclic ring is an optionally substituted indazolyl. Another embodiment provides the compound, or a pharmaceutically acceptable salt thereof, having the structure of Formula (I), wherein the optionally substituted indolyl is an optionally substituted indol-5-yl. Another embodiment provides the compound, or a pharmaceutically acceptable salt thereof, having the structure of Formula (I), wherein the optionally substituted indazolyl is an optionally substituted indazol-5-yl.

One embodiment provides the compound, or a pharmaceutically acceptable salt thereof, having the structure of Formula (II):

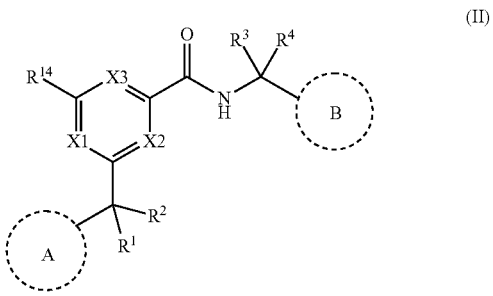

(II)

wherein,
Ring A is an optionally substituted bicyclic heterocyclic ring;
Ring B is a optionally substituted monocyclic heterocyclic ring or optionally substituted bicyclic heterocyclic ring;
X1 is C—$R^{11}$;
X2 is N or C—$R^{12}$;
X3 is N or C—$R^{13}$; with the provision that only one of X2 or X3 is N;
each $R^{11}$, $R^{12}$, $R^{13}$, or $R^{14}$ is independently selected from hydrogen, cyano, halo, hydroxy, azido, amino, nitro, —CO₂H, —S(O)—$R^{20}$, —S—$R^{20}$, —S(O)₂—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —CO₂—$R^{20}$, —CO(NR²¹)₂, —SO₂(NR²¹)₂, —C(=NR²²)—(NR²¹)₂, or optionally substituted alkynyl;
each $R^1$ or $R^2$ is independently selected from hydrogen, halo, hydroxy, amino, —CO₂H, —S(O)—$R^{20}$, —S—$R^{20}$, —S(O)₂—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —CO₂—$R^{20}$, —CO(NR²¹)₂, —SO₂(NR²¹)₂, —C(=NR²²)—(NR²¹)₂, or optionally substituted alkynyl; or optionally, $R^1$ and $R^2$ are optionally substituted C1-C5 alkyl and join to form a ring; or optionally, $R^1$ and $R^2$ together form an oxo;
each $R^3$ or $R^4$ is independently selected from hydrogen, —CO₂H, optionally substituted alkyl, optionally substituted cycloalkyl, optionally substituted alkenyl, optionally substituted aryl, optionally substituted heteroaryl, optionally substituted heterocyclyl, —CO—R$^{20}$, —CO$_2$—R$^{20}$, —CO(NR$^{21}$)$_2$, —SO$_2$(NR$^{21}$)$_2$, —C(═NR$^{22}$)—(NR$^{21}$)$_2$, or optionally substituted alkynyl; or optionally, R$^3$ and R$^4$ are optionally substituted C1-C5 alkyl and join to form a ring;

each R$^{20}$ is selected from optionally substituted alkyl, optionally substituted cycloalkyl, optionally substituted aryl, optionally substituted heteroaryl, or optionally substituted heterocyclyl;

each R$^{21}$ is selected from hydrogen, optionally substituted alkyl, optionally substituted cycloalkyl, optionally substituted aryl, optionally substituted heteroaryl, or optionally substituted heterocyclyl;

each R$^{22}$ is selected from hydrogen, —CN, optionally substituted alkyl, optionally substituted cycloalkyl, optionally substituted aryl, optionally substituted heteroaryl, or optionally substituted heterocyclyl.

Another embodiment provides the compound, or a pharmaceutically acceptable salt thereof, having the structure of Formula (II), wherein X2 is N. Another embodiment provides the compound, or a pharmaceutically acceptable salt thereof, having the structure of Formula (II), wherein X3 is N.

Another embodiment provides the compound, or a pharmaceutically acceptable salt thereof, having the structure of Formula (II), wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1 (2H)-on-2-yl; or optionally substituted quinolin-6-yl. Another embodiment provides the compound, or a pharmaceutically acceptable salt thereof, having the structure of Formula (II), wherein Ring A is an optionally substituted quinolin-6-yl. Another embodiment provides the compound, or a pharmaceutically acceptable salt thereof, having the structure of Formula (II), wherein the quinolin-6-yl is substituted with at least one substituent selected from optionally substituted C1-C3 alkyl, halogen, —CN, —SO$_2$Me, —SO$_2$NH$_2$, —CONH$_2$, —CH$_2$NHAc, —CO$_2$Me, —CO$_2$H, —CH$_2$OH, —CH$_2$NH$_2$, —NH$_2$, —OH, or OMe. Another embodiment provides the compound, or a pharmaceutically acceptable salt thereof, having the structure of Formula (II), wherein the quinolin-6-yl is substituted at least at the 3-position. Another embodiment provides the compound, or a pharmaceutically acceptable salt thereof, having the structure of Formula (II), wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl.

Another embodiment provides the compound, or a pharmaceutically acceptable salt thereof, having the structure of Formula (II), wherein Ring B is selected from an optionally substituted monocyclic heterocyclic ring. Another embodiment provides the compound, or a pharmaceutically acceptable salt thereof, having the structure of Formula (II), wherein the optionally substituted monocyclic heterocyclic ring is selected from optionally substituted imidazolyl, optionally substituted pyrazolyl, optionally substituted pyridinyl, optionally substituted pyridazinyl, optionally substituted pyrimidinyl, or optionally substituted pyrazinyl. Another embodiment provides the compound, or a pharmaceutically acceptable salt thereof, having the structure of Formula (II), wherein the optionally substituted monocyclic heterocyclic ring is an optionally substituted pyridinyl. Another embodiment provides the compound, or a pharmaceutically acceptable salt thereof, having the structure of Formula (II), wherein the optionally substituted pyridinyl is an optionally substituted aminopyridinyl. Another embodiment provides the compound, or a pharmaceutically acceptable salt thereof, having the structure of Formula (II), wherein the optionally substituted aminopyridinyl is an optionally substituted 6-aminopyridin-3-yl.

Another embodiment provides the compound, or a pharmaceutically acceptable salt thereof, having the structure of Formula (II), wherein Ring B is selected from an optionally substituted bicyclic heterocyclic ring. Another embodiment provides the compound, or a pharmaceutically acceptable salt thereof, having the structure of Formula (II), wherein the optionally substituted bicyclic heterocyclic ring is selected from optionally substituted quinolinyl, isoquinolinyl, quinazolinyl, indolyl, indazolyl, 1H-pyrrolo[2,3-b]pyridinyl, benzoxazolyl, benzoisoxazolyl, or benzimidazolyl. Another embodiment provides the compound, or a pharmaceutically acceptable salt thereof, having the structure of Formula (II), wherein the optionally substituted bicyclic heterocyclic ring is an optionally substituted indolyl. Another embodiment provides the compound, or a pharmaceutically acceptable salt thereof, having the structure of Formula (II), wherein the optionally substituted bicyclic heterocyclic ring is an optionally substituted indazolyl. Another embodiment provides the compound, or a pharmaceutically acceptable salt thereof, having the structure of Formula (II), wherein the optionally substituted indolyl is an optionally substituted indol-5-yl. Another embodiment provides the compound, or a pharmaceutically acceptable salt thereof, having the structure of Formula (II), wherein the optionally substituted indazolyl is an optionally substituted indazol-5-yl.

One embodiment provides a compound, or a pharmaceutically acceptable salt thereof, selected from:

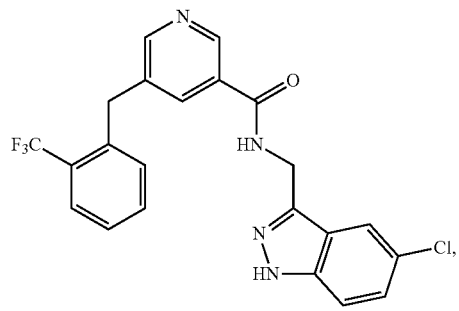

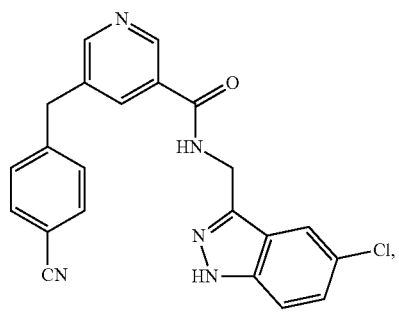

25
-continued
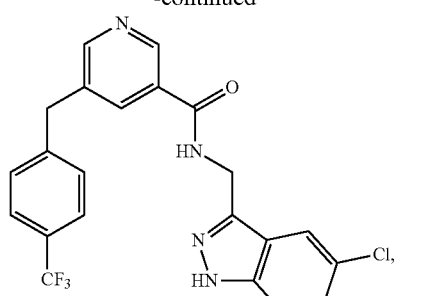
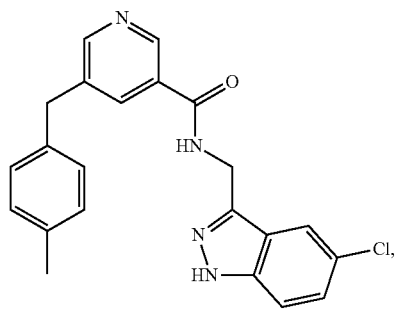
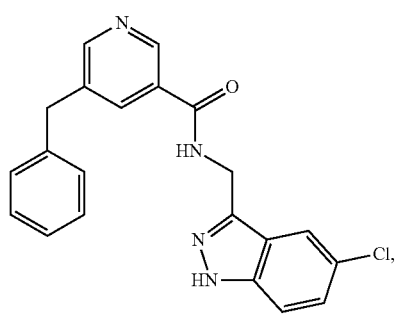
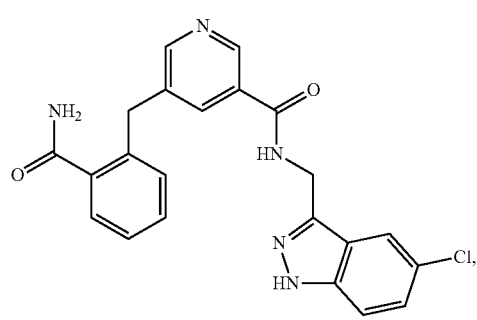
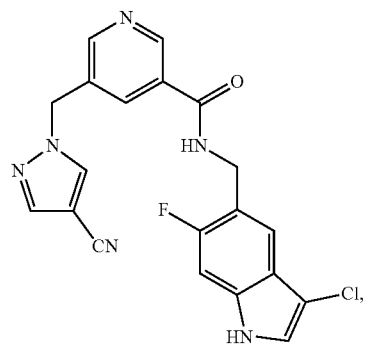
26
-continued
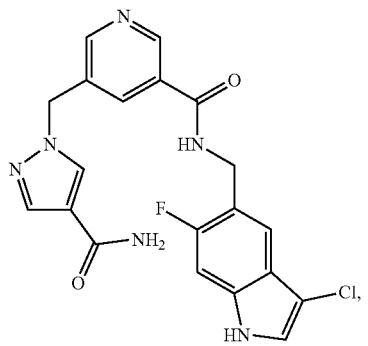
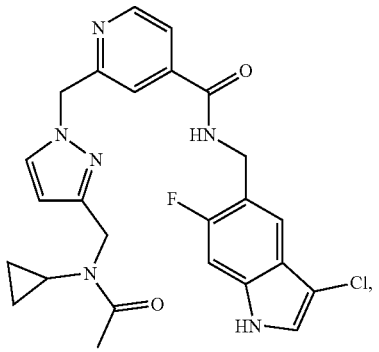
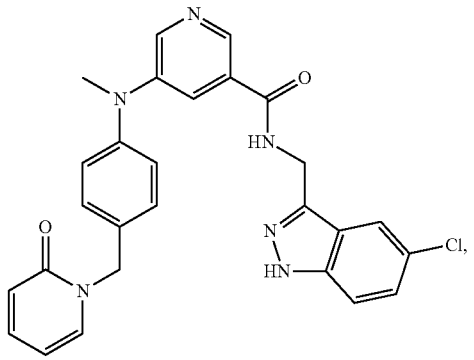
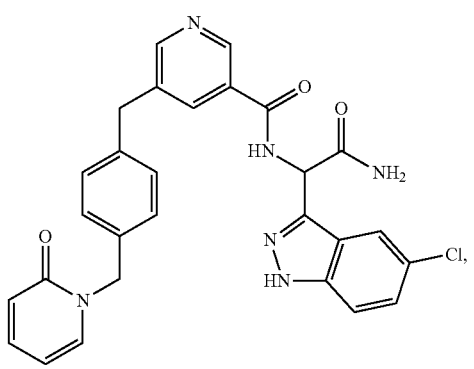

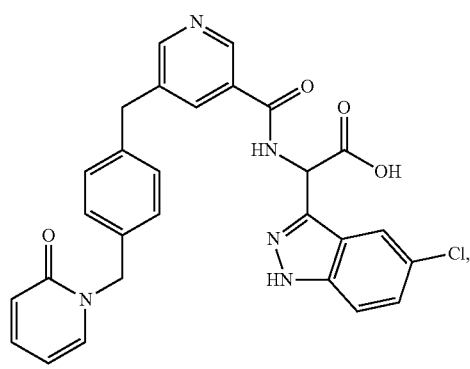
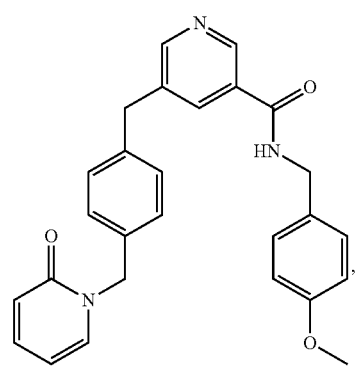
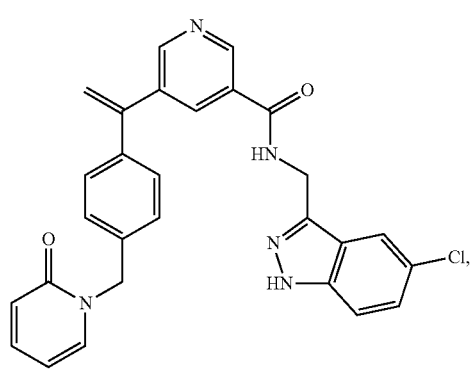
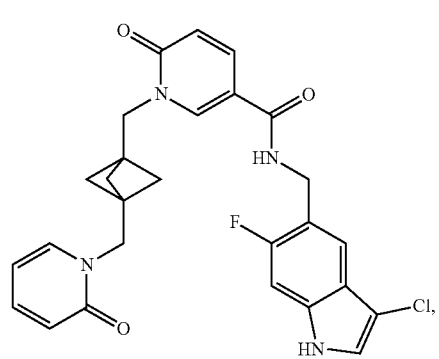
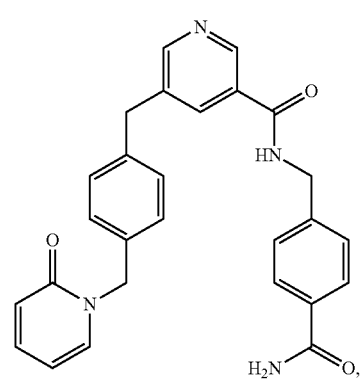
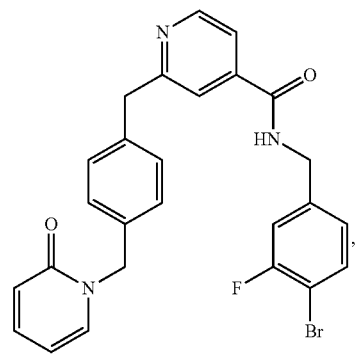
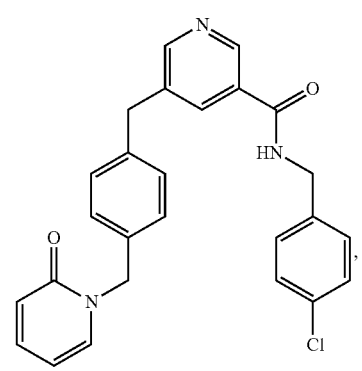
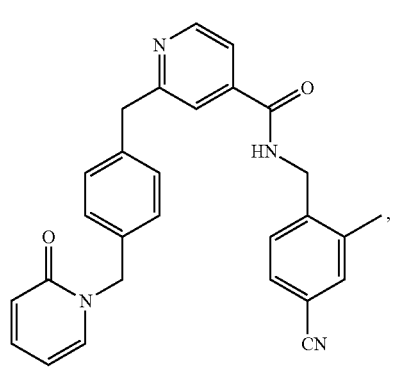

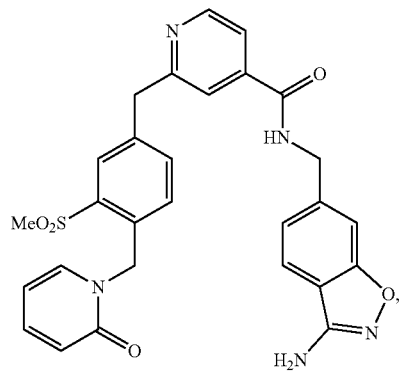
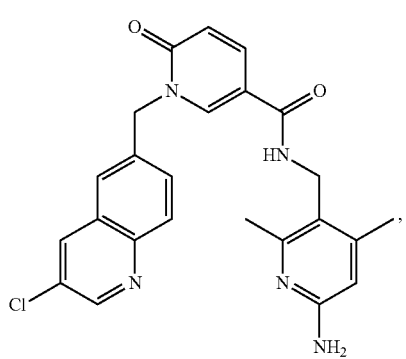
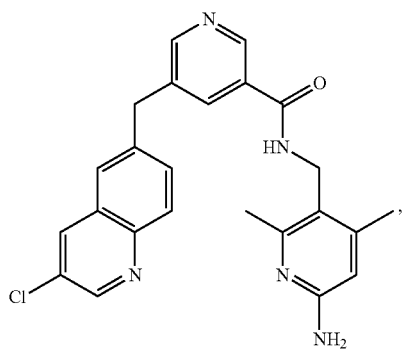
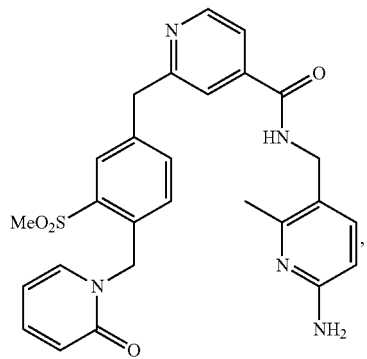
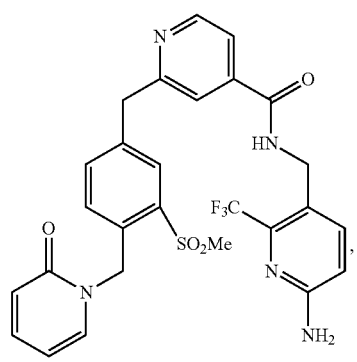
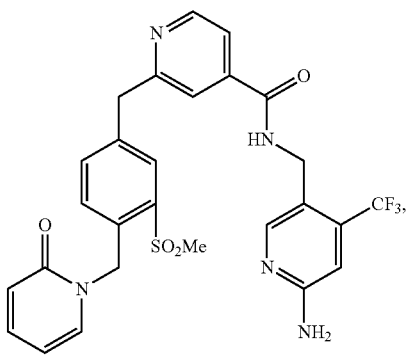
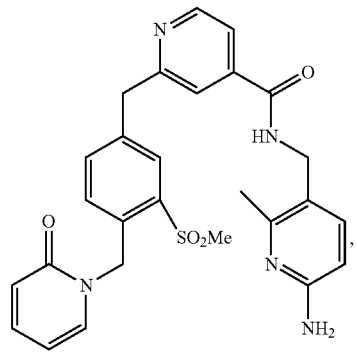
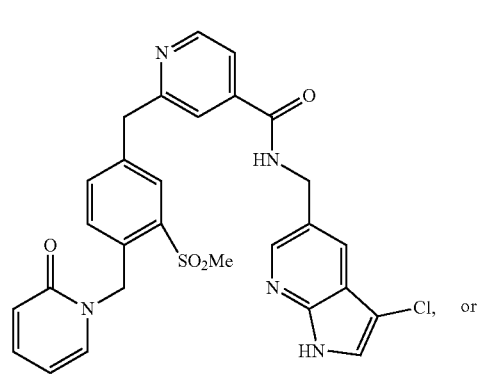

-continued
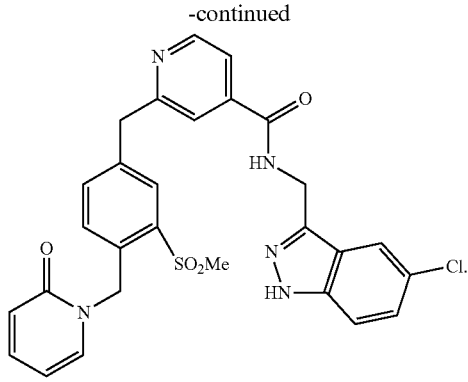
One embodiment provides a compound, or a pharmaceutically acceptable salt thereof, selected from:
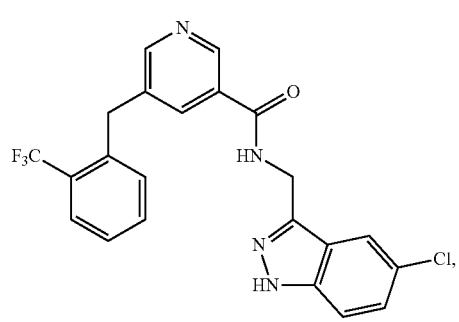
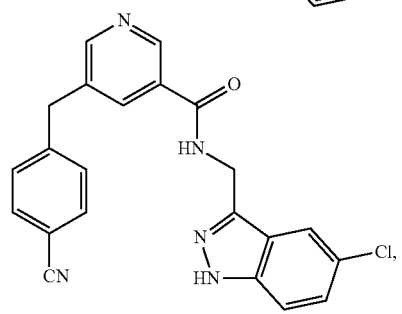
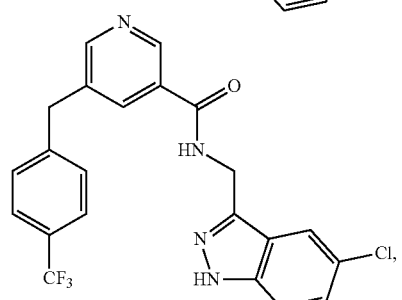
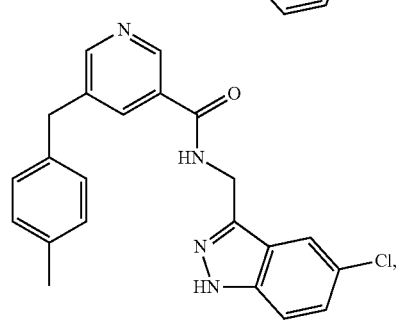
-continued
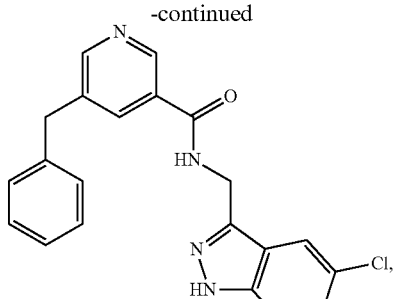
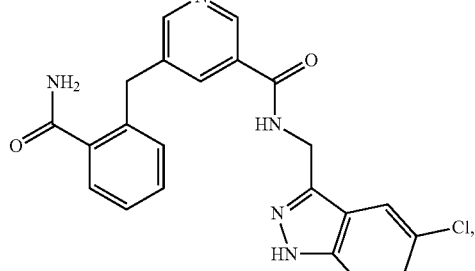
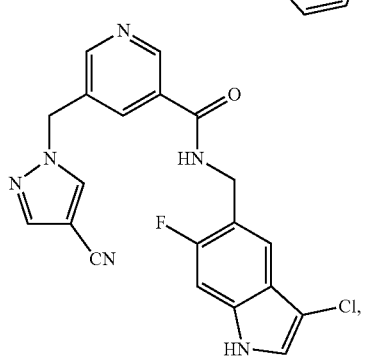
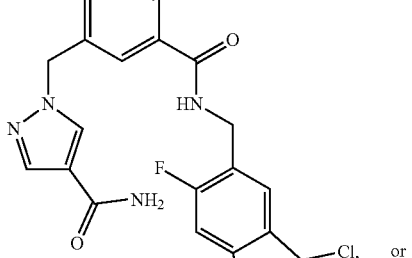
or
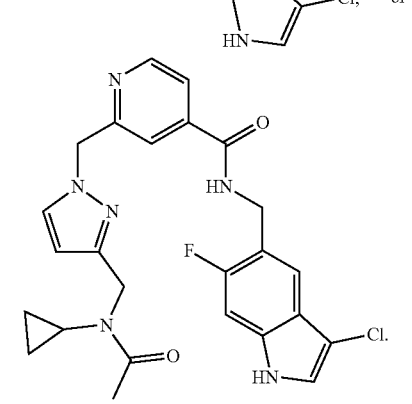
One embodiment provides a compound, or a pharmaceutically acceptable salt thereof, selected from:

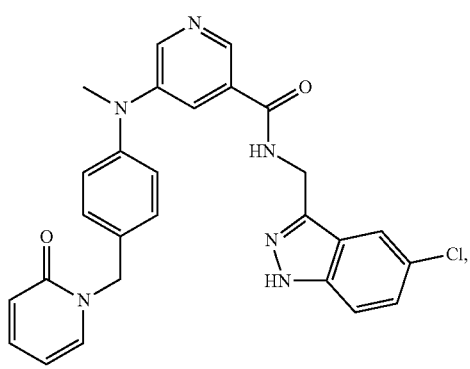
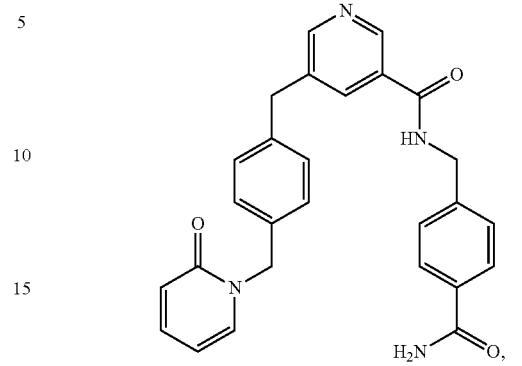
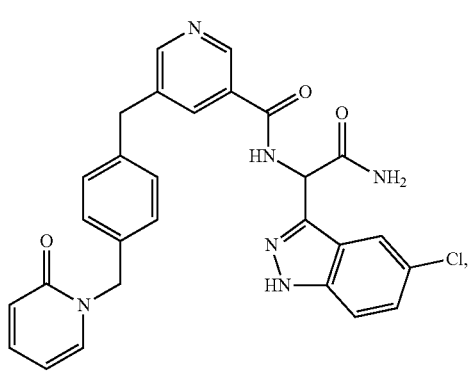
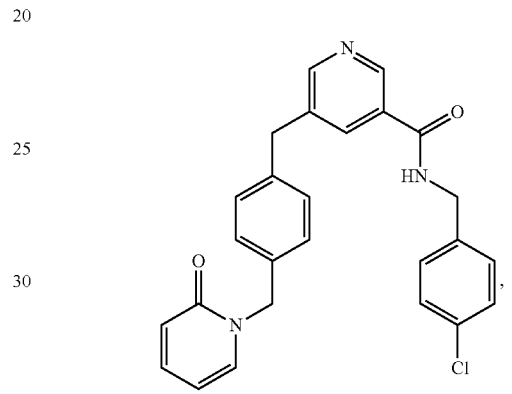
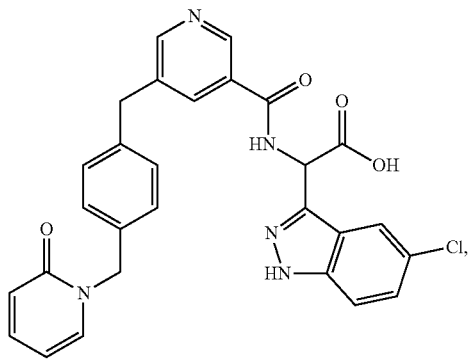
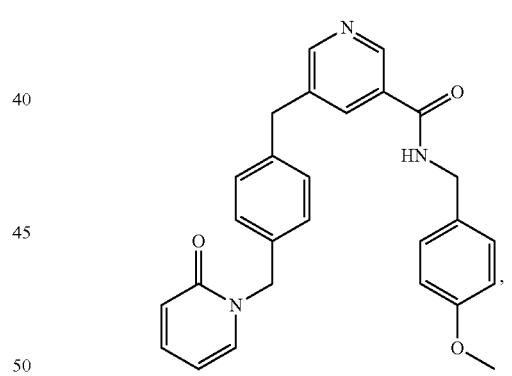
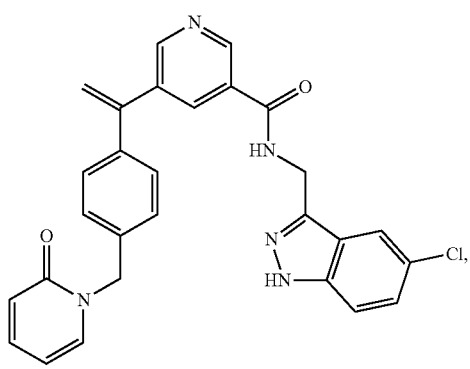
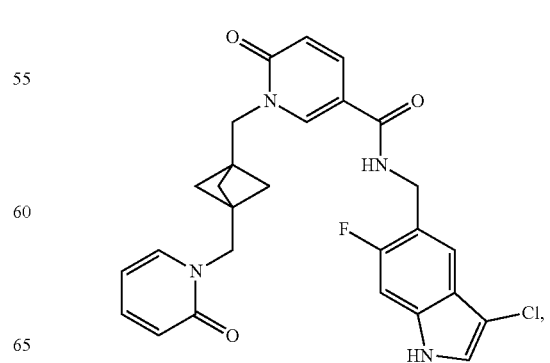

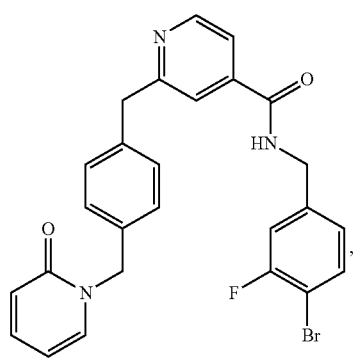
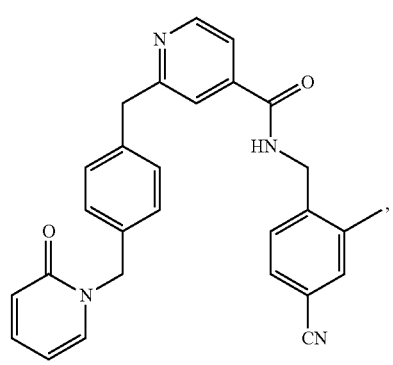
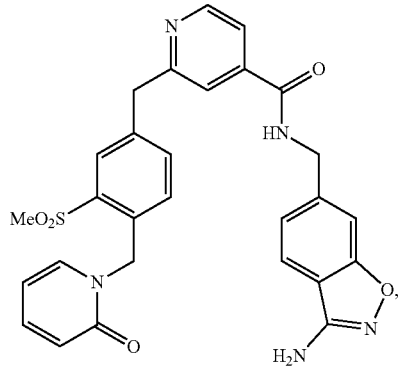
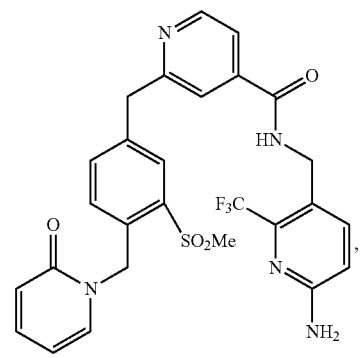
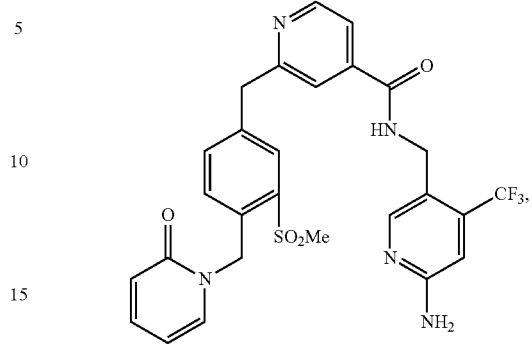
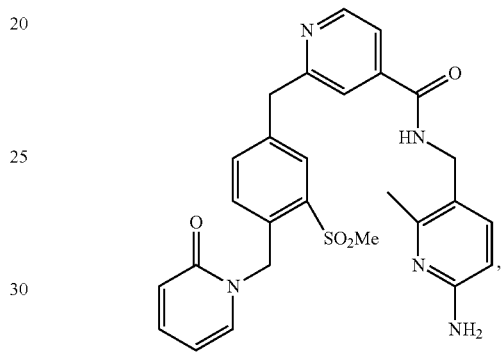
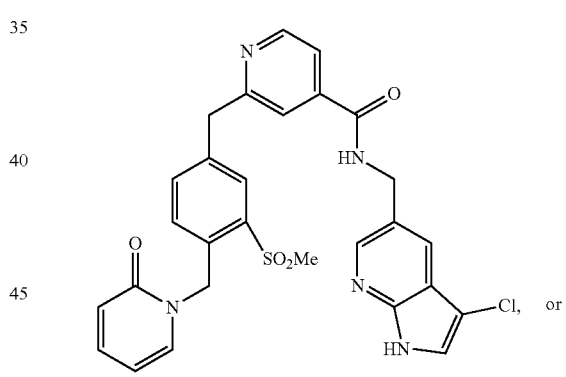
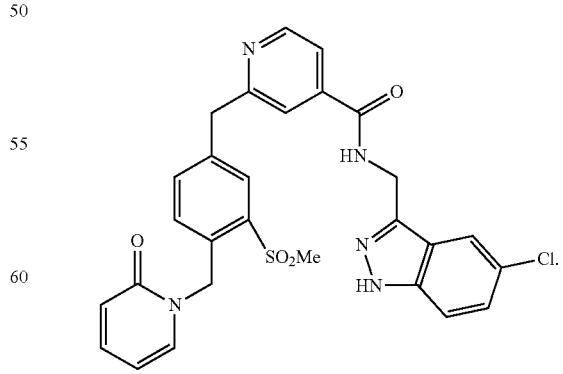
One embodiment provides a compound, or a pharmaceutically acceptable salt thereof, selected from:

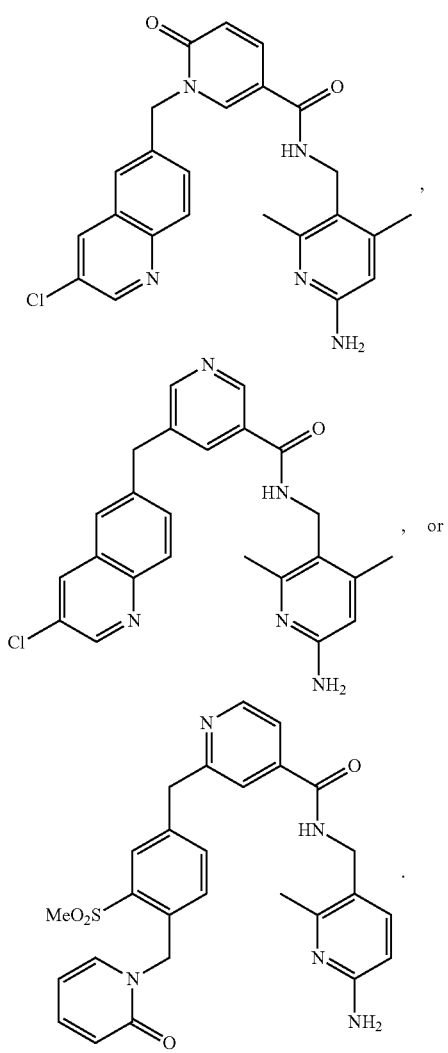
One embodiment provides a compound, or a pharmaceutically acceptable salt thereof, selected from:
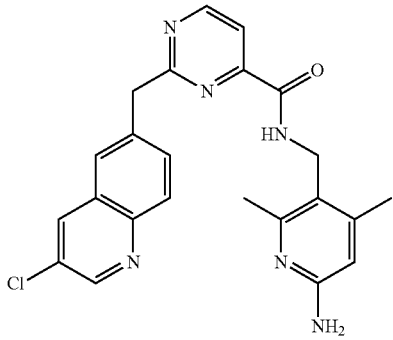
or
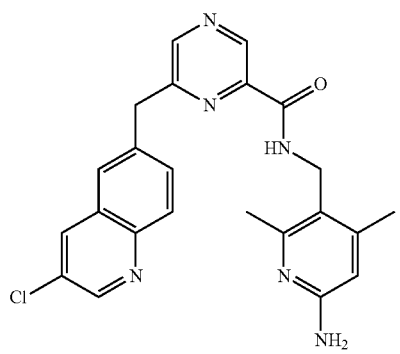
In some embodiments, the kallikrein inhibitory compound described herein has a structure provided in Table 1.
TABLE 1
| Chemical Synthesis Example | Structure | Name |
| --- | --- | --- |
| 1 | 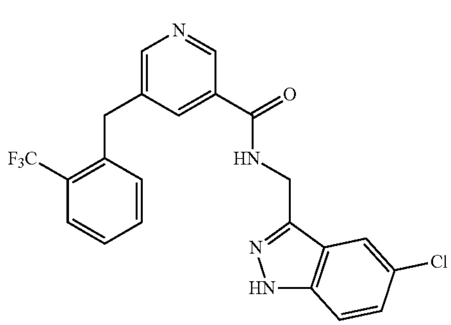 [SMILES: O=C(NCc1n[nH]c2ccc(Cl)cc12)c1cncc(Cc2ccccc2C(F)(F)F)c1] | N-((5-chloro-1H-indazol-3-yl)methyl)-5-(2-(trifluoromethyl)benzyl)nicotinamide |

TABLE 1-continued

| Chemical Synthesis Example | Structure | Name |
|---|---|---|
| 2 | 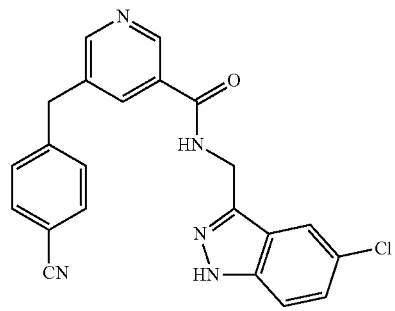 | N-((5-chloro-1H-indazol-3-yl)methyl)-5-(4-cyanobenzyl)nicotinamide |
| 3 | 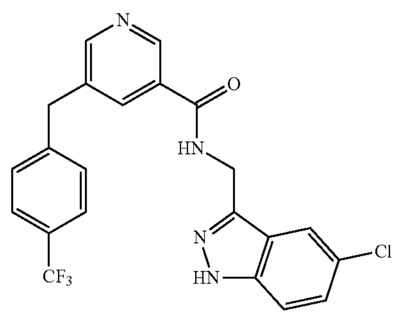 [SMILES: N#Cc1ccc(Cc2cncc(C(=O)NCc3n[nH]c4ccc(Cl)cc34)c2)cc1] | N-((5-chloro-1H-indazol-3-yl)methyl)-5-(4-(trifluoromethyl)benzyl)nicotinamide |
| 4 | 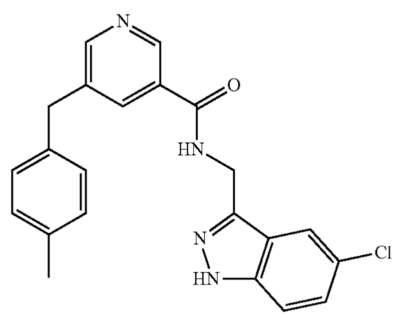 [SMILES: Cc1ccc(Cc2cncc(C(=O)NCc3n[nH]c4ccc(Cl)cc34)c2)cc1] | N-((5-chloro-1H-indazol-3-yl)methyl)-5-(4-methylbenzyl)nicotinamide |
| 5 | 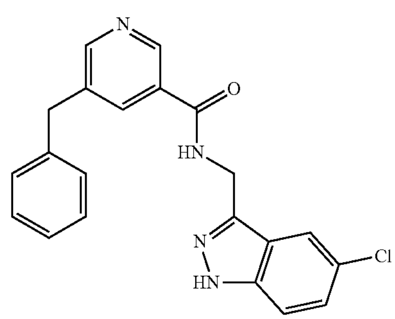 [SMILES: O=C(NCc1n[nH]c2ccc(Cl)cc12)c1cncc(Cc2ccccc2)c1] | 5-benzyl-N-((5-chloro-1H-indazol-3-yl)methyl)nicotinamide |
| 6 | 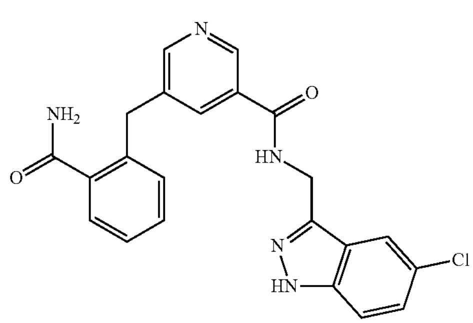 [SMILES: NC(=O)c1ccccc1Cc1cncc(C(=O)NCc2n[nH]c3ccc(Cl)cc23)c1] | 5-(2-carbamoylbenzyl)-N-((5-chloro-1H-indazol-3-yl)methyl)nicotinamide |

TABLE 1-continued

| Chemical Synthesis Example | Structure | Name |
|---|---|---|
| 7 | 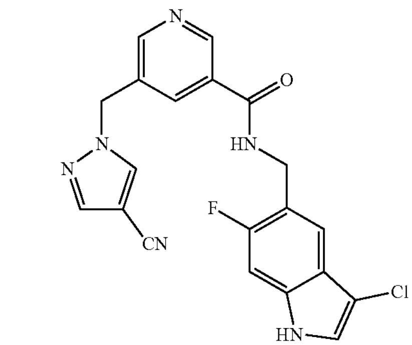 [SMILES: N#Cc1cnn(Cc2cncc(C(=O)NCc3cc4c(Cl)c[nH]c4cc3F)c2)c1] | N-((3-chloro-6-fluoro-1H-indol-5-yl)methyl)-5-((4-cyano-1H-pyrazol-1-yl)methyl)nicotinamide |
| 8 | 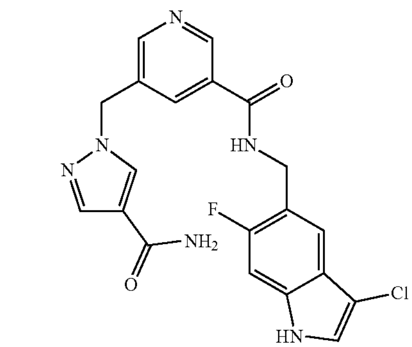 [SMILES: NC(=O)c1cnn(Cc2cncc(C(=O)NCc3cc4c(Cl)c[nH]c4cc3F)c2)c1] | 5-((4-carbamoyl-1H-pyrazol-1-yl)methyl)-N-((3-chloro-6-fluoro-1H-indol-5-yl)methyl)nicotinamide |
| 9 | 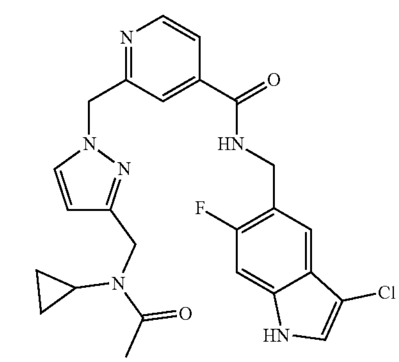 [SMILES: CC(=O)N(Cc1ccn(Cc2cc(C(=O)NCc3cc4c(Cl)c[nH]c4cc3F)ccn2)n1)C1CC1] | N-((3-chloro-6-fluoro-1H-indol-5-yl)methyl)-2-((3-((N-cyclopropylacetamido)methyl)-1H-pyrazol-1-yl)methyl)isonicotinamide |
| 10 | 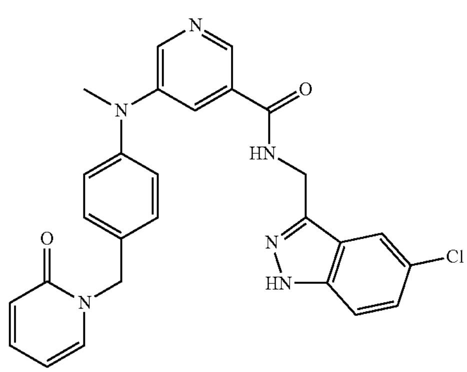 [SMILES: CN(c1ccc(Cn2ccccc2=O)cc1)c1cncc(C(=O)NCc2n[nH]c3ccc(Cl)cc23)c1] | N-((5-chloro-1H-indazol-3-yl)methyl)-6-(methyl(4-((2-oxopyridin-1(2H)-yl)methyl)phenyl)amino)picolinamide |

TABLE 1-continued

| Chemical Synthesis Example | Structure | Name |
| --- | --- | --- |
| 11 | 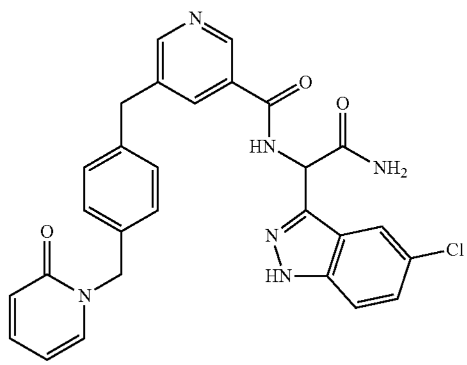 [SMILES: NC(=O)C(NC(=O)c1cncc(Cc2ccc(Cn3ccccc3=O)cc2)c1)c1n[nH]c2ccc(Cl)cc12] | N-(2-amino-1-(5-chloro-1H-indazol-3-yl)-2-oxoethyl)-5-(4-((2-oxopyridin-1(2H)-yl)methyl)benzyl) nicotinamide |
| 12 | 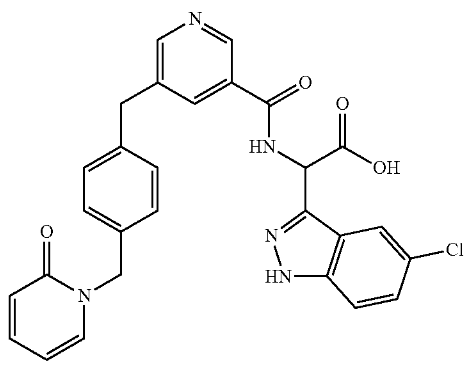 [SMILES: O=C(NC(C(=O)O)c1n[nH]c2ccc(Cl)cc12)c1cncc(Cc2ccc(Cn3ccccc3=O)cc2)c1] | 2-(5-chloro-1H-indazol-3-yl)-2-(5-(4-((2-oxopyridin-1(2H)-yl)methyl)benzyl) nicotinamido)acetic acid |
| 13 | 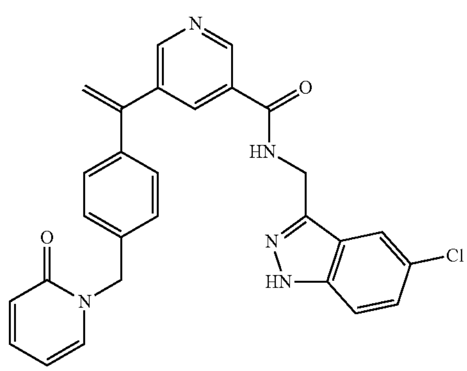 [SMILES: C=C(c1ccc(Cn2ccccc2=O)cc1)c1cncc(C(=O)NCc2n[nH]c3ccc(Cl)cc23)c1] | N-((5-chloro-1H-indazol-3-yl)methyl)-3-(1-(4-((2-oxopyridin-1(2H)-yl)methyl)phenyl)vinyl) benzamide |
| 14 | 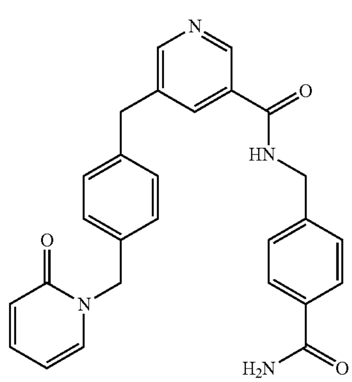 [SMILES: NC(=O)c1ccc(CNC(=O)c2cncc(Cc3ccc(Cn4ccccc4=O)cc3)c2)cc1] | N-(4-carbamoylbenzyl)-5-(4-((2-oxopyridin-1(2H)-yl)methyl)benzyl) nicotinamide |

TABLE 1-continued

| Chemical Synthesis Example | Structure | Name |
| --- | --- | --- |
| 15 | 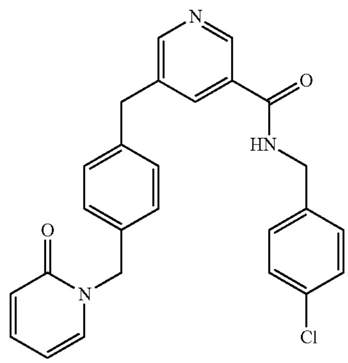 [SMILES: O=C(NCc1ccc(Cl)cc1)c1cncc(Cc2ccc(Cn3ccccc3=O)cc2)c1] | N-(4-chlorobenzyl)-5-(4-((2-oxopyridin-1(2H)-yl)methyl)benzyl)nicotinamide |
| 16 | 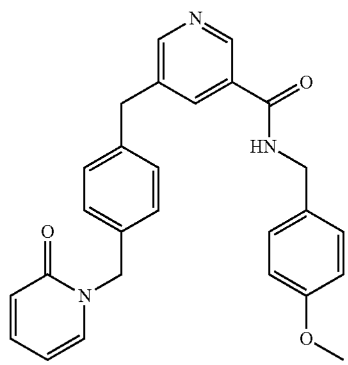 [SMILES: COc1ccc(CNC(=O)c2cncc(Cc3ccc(Cn4ccccc4=O)cc3)c2)cc1] | N-(4-methoxybenzyl)-5-(4-((2-oxopyridin-1(2H)-yl)methyl)benzyl)nicotinamide |
| 17 | 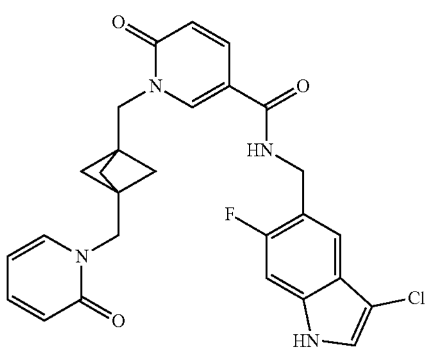 [SMILES: O=C(NCc1cc2c(Cl)c[nH]c2cc1F)c1ccc(=O)n(CC23CC(Cn4ccccc4=O)(C2)C3)c1] | N-((3-chloro-6-fluoro-1H-indol-5-yl)methyl)-6-oxo-1-((3-((2-oxopyridin-1(2H)-yl)methyl)bicyclo[1.1.1]pentan-1-yl)methyl)-1,6-dihydropyridine-3-carboxamide |
| 18 | 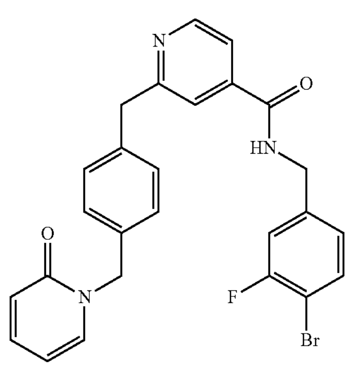 [SMILES: O=C(NCc1ccc(Br)c(F)c1)c1ccnc(Cc2ccc(Cn3ccccc3=O)cc2)c1] | N-(4-bromo-3-fluorobenzyl)-2-(4-((2-oxopyridin-1(2H)-yl)methyl)benzyl)isonicotinamide |

TABLE 1-continued

| Chemical Synthesis Example | Structure | Name |
| --- | --- | --- |
| 19 | 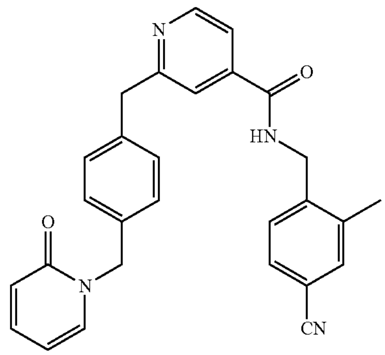 [SMILES: Cc1cc(C#N)ccc1CNC(=O)c1ccnc(Cc2ccc(Cn3ccccc3=O)cc2)c1] | N-(4-cyano-2-methylbenzyl)-2-(4-((2-oxopyridin-1(2H)-yl)methyl)benzyl)isonicotinamide |
| 20 | 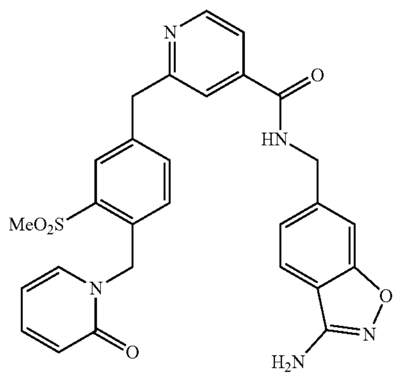 [SMILES: CS(=O)(=O)c1cc(Cc2cc(C(=O)NCc3ccc4c(N)noc4c3)ccn2)ccc1Cn1ccccc1=O] | N-((3-aminobenzo[d]isoxazol-6-yl)methyl)-2-(3-(methylsulfonyl)-4-((2-oxopyridin-1(2H)-yl)methyl)benzyl)isonicotinamide |
| 21 | 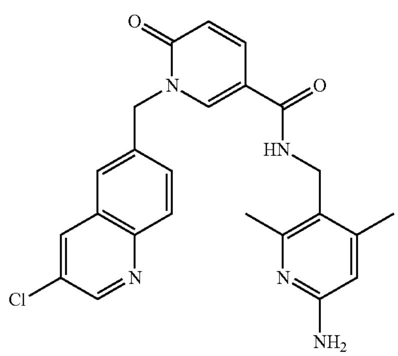 [SMILES: Cc1cc(N)nc(C)c1CNC(=O)c1ccc(=O)n(Cc2ccc3ncc(Cl)cc3c2)c1] | N-((6-amino-2,4-dimethylpyridin-3-yl)methyl)-1-((3-chloroquinolin-6-yl)methyl)-6-oxo-1,6-dihydropyridine-3-carboxamide |
| 22 | 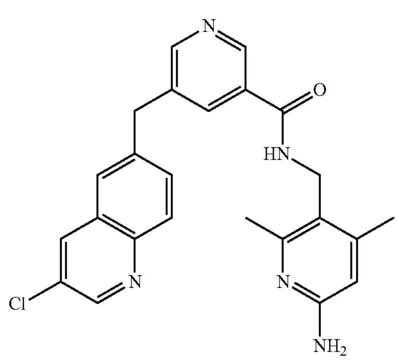 [SMILES: Cc1cc(N)nc(C)c1CNC(=O)c1cncc(Cc2ccc3ncc(Cl)cc3c2)c1] | N-((6-amino-2,4-dimethylpyridin-3-yl)methyl)-5-((3-chloroquinolin-6-yl)methyl)nicotinamide |

TABLE 1-continued

| Chemical Synthesis Example | Structure | Name |
|---|---|---|
| 23 | 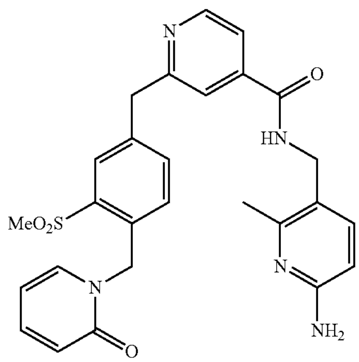 [SMILES: Cc1nc(N)ccc1CNC(=O)c1ccnc(Cc2ccc(Cn3ccccc3=O)c(S(C)(=O)=O)c2)c1] | N-((6-amino-2-methylpyridin-3-yl)methyl)-2-(3-(methylsulfonyl)-4-((2-oxopyridin-1(2H)-yl)methyl)benzyl)isonicotinamide |
| 24 | 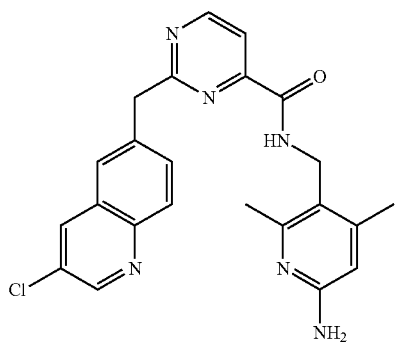 [SMILES: Cc1cc(N)nc(C)c1CNC(=O)c1ccnc(Cc2ccc3ncc(Cl)cc3c2)n1] | N-((6-amino-2,4-dimethylpyridin-3-yl)methyl)-2-((3-chloroquinolin-6-yl)methyl)pyrimidine-4-carboxamide |
| 25 | 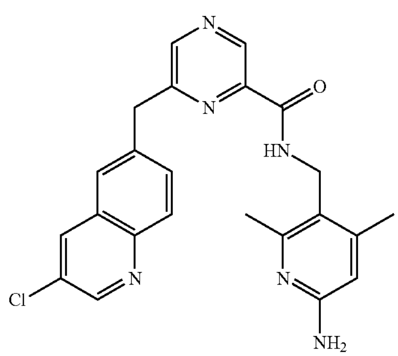 [SMILES: Cc1cc(N)nc(C)c1CNC(=O)c1cncc(Cc2ccc3ncc(Cl)cc3c2)n1] | N-((6-amino-2,4-dimethylpyridin-3-yl)methyl)-6-((3-chloroquinolin-6-yl)methyl)pyrazine-2-carboxamide |
| 26 | 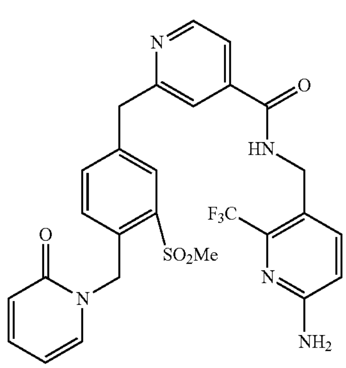 [SMILES: CS(=O)(=O)c1cc(Cc2cc(C(=O)NCc3ccc(N)nc3C(F)(F)F)ccn2)ccc1Cn1ccccc1=O] | N-((6-amino-2-(trifluoromethyl)pyridin-3-yl)methyl)-2-(3-(methylsulfonyl)-4-((2-oxopyridin-1(2H)-yl)methyl)benzyl)isonicotinamide |

TABLE 1-continued

| Chemical Synthesis Example | Structure | Name |
| --- | --- | --- |
| 27 | 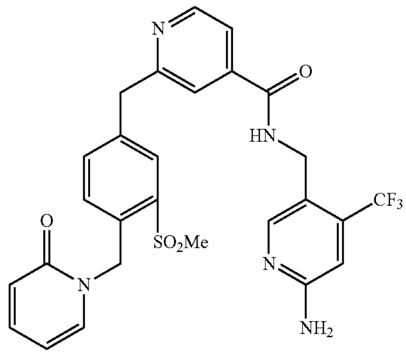 [SMILES: CS(=O)(=O)c1cc(Cc2cc(C(=O)NCc3cnc(N)cc3C(F)(F)F)ccn2)ccc1Cn1ccccc1=O] | N-((6-amino-4-(trifluoromethyl)pyridin-3-yl)methyl)-2-(3-(methylsulfonyl)-4-((2-oxopyridin-1(2H)-yl)methyl)benzyl)isonicotinamide |
| 28 | 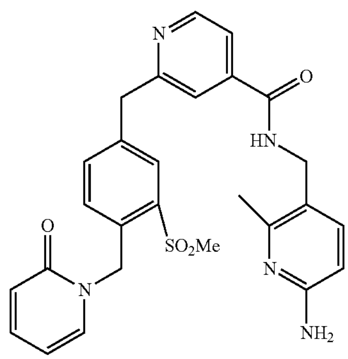 [SMILES: Cc1nc(N)ccc1CNC(=O)c1ccnc(Cc2ccc(Cn3ccccc3=O)c(S(C)(=O)=O)c2)c1] | N-((6-amino-2-methylpyridin-3-yl)methyl)-2-(3-(methylsulfonyl)-4-((2-oxopyridin-1(2H)-yl)methyl)benzyl)isonicotinamide |
| 29 | 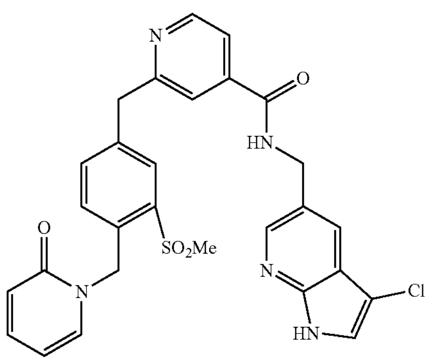 [SMILES: CS(=O)(=O)c1cc(Cc2cc(C(=O)NCc3cnc4[nH]cc(Cl)c4c3)ccn2)ccc1Cn1ccccc1=O] | N-((3-chloro-1H-indol-5-yl)methyl)-2-(3-(methylsulfonyl)-4-((2-oxopyridin-1(2H)-yl)methyl)benzyl)isonicotinamide |
| 30 | 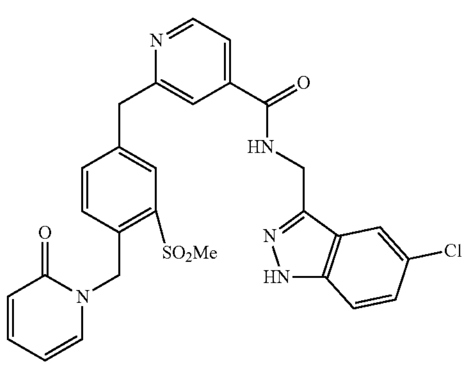 [SMILES: CS(=O)(=O)c1cc(Cc2cc(C(=O)NCc3n[nH]c4ccc(Cl)cc34)ccn2)ccc1Cn1ccccc1=O] | N-((5-chloro-1H-indazol-3-yl)methyl)-2-(3-(methylsulfonyl)-4-((2-oxopyridin-1(2H)-yl)methyl)benzyl)isonicotinamide |

In some embodiments, the kallikrein inhibitory compound described in Formula (I) has a structure provided in Table 2.

TABLE 2

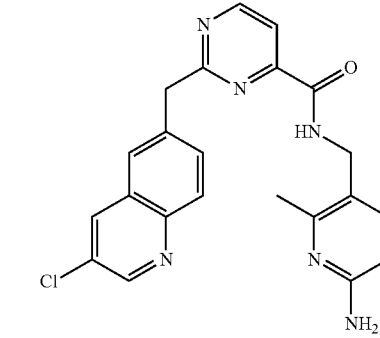

N-((6-amino-2-methylpyridin-3-yl)methyl)-2-((3-chloroquinolin-6-yl)methyl)pyrimidine-4-carboxamide

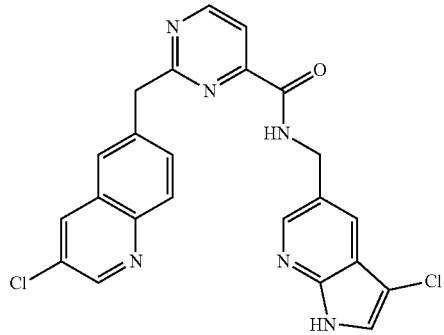 [SMILES: O=C(NCc1cnc2[nH]cc(Cl)c2c1)c1ccnc(Cc2ccc3ncc(Cl)cc3c2)n1]

N-((3-chloro-1H-pyrrolo[2,3-b]pyridin-5-yl)methyl)-2-((3-chloroquinolin-6-yl)methyl)pyrimidine-4-carboxamide

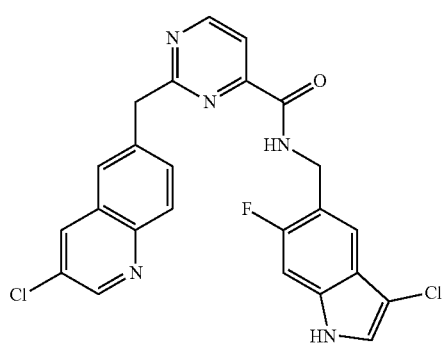 [SMILES: O=C(NCc1cc2c(Cl)c[nH]c2cc1F)c1ccnc(Cc2ccc3ncc(Cl)cc3c2)n1]

N-((3-chloro-6-fluoro-1H-indol-5-yl)methyl)-2-((3-chloroquinolin-6-yl)methyl)pyrimidine-4-carboxamide TABLE 2-continued

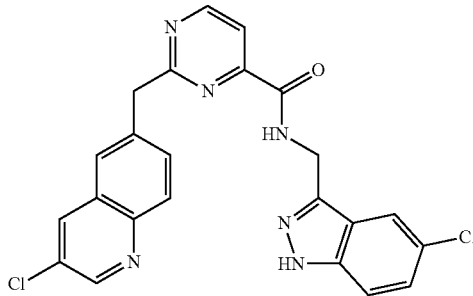

N-((5-chloro-1H-indazol-3-yl)methyl)-2-((3-chloroquinolin-6-yl)methyl)pyrimidine-4-carboxamide

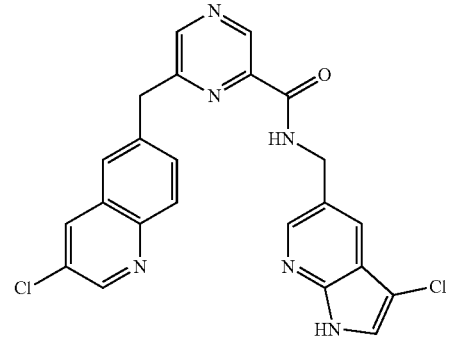 [SMILES: O=C(NCc1cnc2[nH]cc(Cl)c2c1)c1cncc(Cc2ccc3ncc(Cl)cc3c2)n1]

N-((3-chloro-1H-pyrrolo[2,3-b]pyridin-5-yl)methyl)-6-((3-chloroquinolin-6-yl)methyl)pyrazine-2-carboxamide

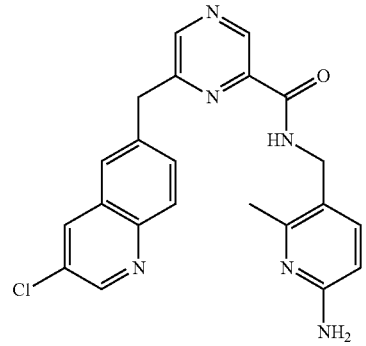 [SMILES: Cc1nc(N)ccc1CNC(=O)c1cncc(Cc2ccc3ncc(Cl)cc3c2)n1]

N-((6-amino-2-methylpyridin-3-yl)methyl)-6-((3-chloroquinolin-6-yl)methyl)pyrazine-2-carboxamide

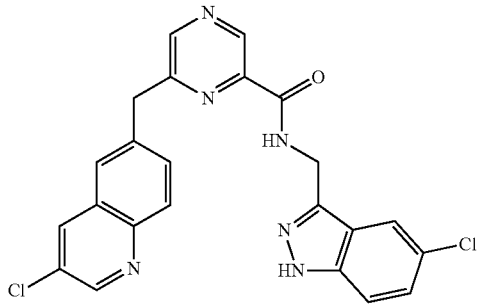 [SMILES: O=C(NCc1n[nH]c2ccc(Cl)cc12)c1cncc(Cc2ccc3ncc(Cl)cc3c2)n1]

N-((5-chloro-1H-indazol-3-yl)methyl)-6-((3-chloroquinolin-6-yl)methyl)pyrazine-2-carboxamide TABLE 2-continued

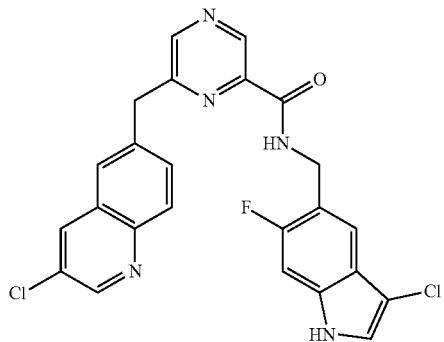 [SMILES: O=C(NCc1cc2c(Cl)c[nH]c2cc1F)c1cncc(Cc2ccc3ncc(Cl)cc3c2)n1]

N-((3-chloro-6-fluoro-1H-indol-5-yl)methyl)-6-
((3-chloroquinolin-6-yl)methyl)pyrazine-2-
carboxamide

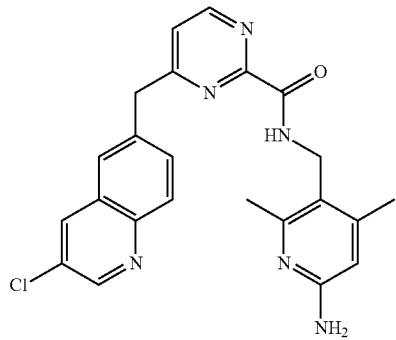

N-((6-amino-2,4-dimethylpyridin-3-yl)methyl)-4-
((3-chloroquinolin-6-yl)methyl)pyrimidine-2-
carboxamide

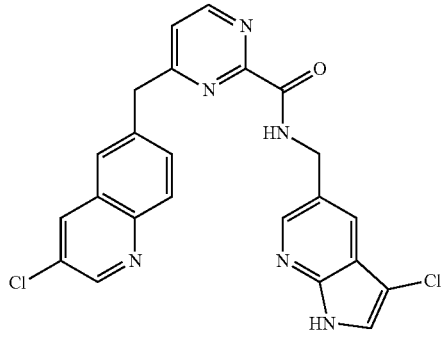 [SMILES: O=C(NCc1cnc2[nH]cc(Cl)c2c1)c1nccc(Cc2ccc3ncc(Cl)cc3c2)n1]

N-((3-chloro-1H-pyrrolo[2,3-b]pyridin-5-
yl)methyl)-4-((3-chloroquinolin-6-
yl)methyl)pyrimidine-2-carboxamide

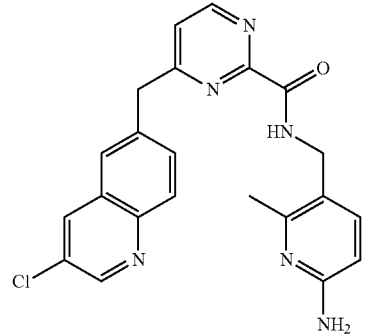 [SMILES: Cc1nc(N)ccc1CNC(=O)c1nccc(Cc2ccc3ncc(Cl)cc3c2)n1]

N-((6-amino-2-methylpyridin-3-yl)methyl)-4-((3-
chloroquinolin-6-yl)methyl)pyrimidine-2-
carboxamide TABLE 2-continued

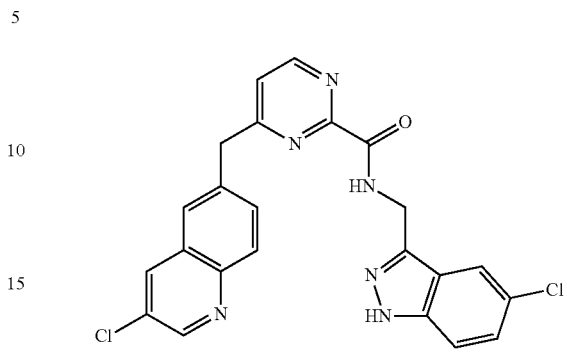

N-((5-chloro-1H-indazol-3-yl)methyl)-4-((3-
chloroquinolin-6-yl)methyl)pyrimidine-2-
carboxamide

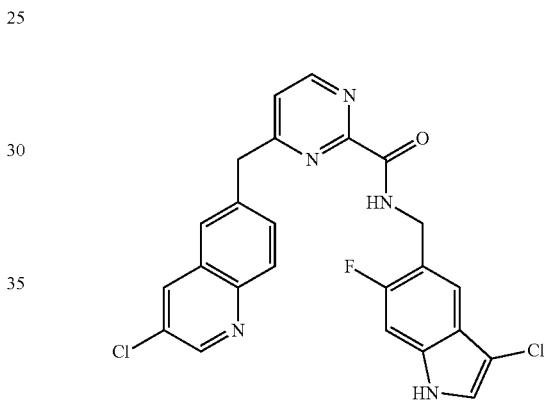

N-((3-chloro-6-fluoro-1H-indol-5-yl)methyl)-4-
((3-chloroquinolin-6-yl)methyl)pyrimidine-2-
carboxamide

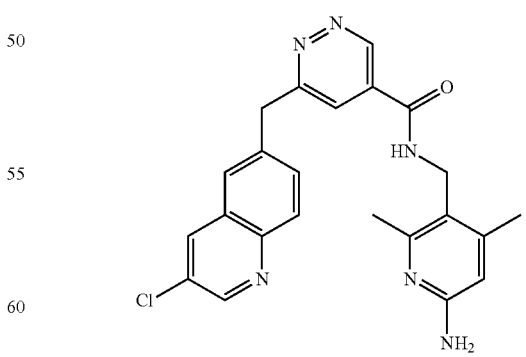

N-((6-amino-2,4-dimethylpyridin-3-yl)methyl)-6-
((3-chloroquinolin-6-yl)methyl)pyridazine-4-
carboxamide TABLE 2-continued

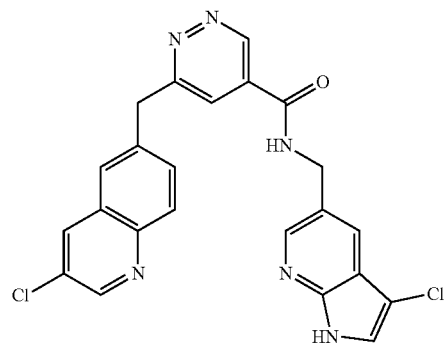 [SMILES: O=C(NCc1cnc2[nH]cc(Cl)c2c1)c1cnnc(Cc2ccc3ncc(Cl)cc3c2)c1]

N-((3-chloro-1H-pyrrolo[2,3-b]pyridin-5-yl)methyl)-6-((3-chloroquinolin-6-yl)methyl)pyridazine-4-carboxamide

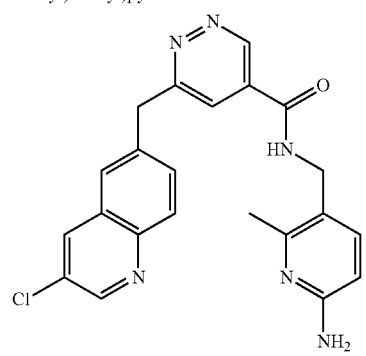

N-((6-amino-2-methylpyridin-3-yl)methyl)-6-((3-chloroquinolin-6-yl)methyl)pyridazine-4-carboxamide

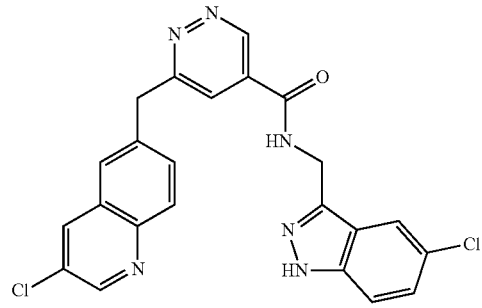 [SMILES: O=C(NCc1n[nH]c2ccc(Cl)cc12)c1cnnc(Cc2ccc3ncc(Cl)cc3c2)c1]

N-((5-chloro-1H-indazol-3-yl)methyl)-6-((3-chloroquinolin-6-yl)methyl)pyridazine-4-carboxamide

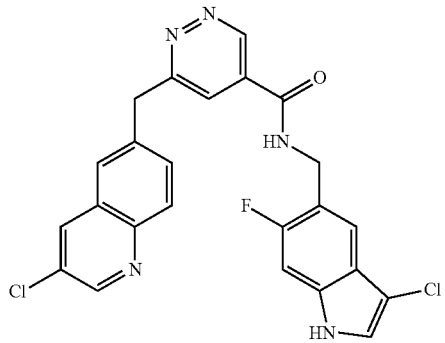 [SMILES: O=C(NCc1cc2c(Cl)c[nH]c2cc1F)c1cnnc(Cc2ccc3ncc(Cl)cc3c2)c1]

N-((3-chloro-6-fluoro-1H-indol-5-yl)methyl)-6-((3-chloroquinolin-6-yl)methyl)pyridazine-4-carboxamide TABLE 2-continued

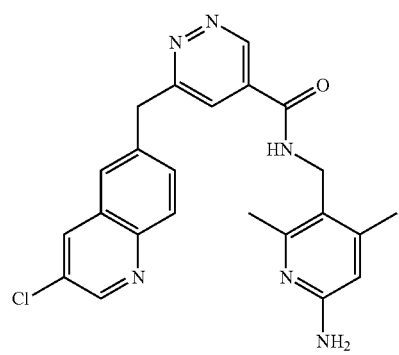 [SMILES: Cc1cc(N)nc(C)c1CNC(=O)c1cnnc(Cc2ccc3ncc(Cl)cc3c2)c1]

N-((6-amino-2,4-dimethylpyridin-3-yl)methyl)-6-((3-chloroquinolin-6-yl)methyl)pyrimidine-4-carboxamide

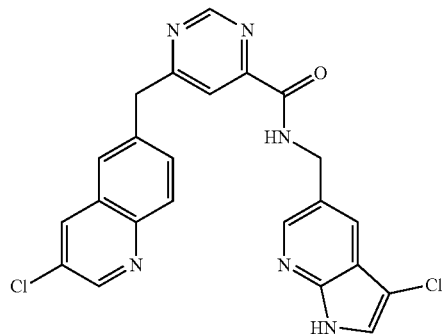 [SMILES: O=C(NCc1cnc2[nH]cc(Cl)c2c1)c1cc(Cc2ccc3ncc(Cl)cc3c2)ncn1]

N-((3-chloro-1H-pyrrolo[2,3-b]pyridin-5-yl)methyl)-6-((3-chloroquinolin-6-yl)methyl)pyrimidine-4-carboxamide

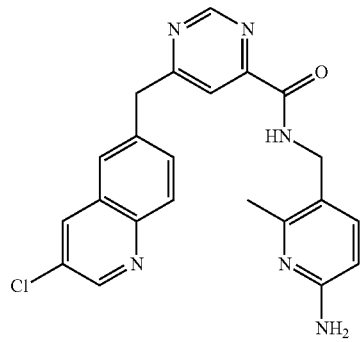

N-((6-amino-2-methylpyridin-3-yl)methyl)-6-((3-chloroquinolin-6-yl)methyl)pyrimidine-4-carboxamide TABLE 2-continued

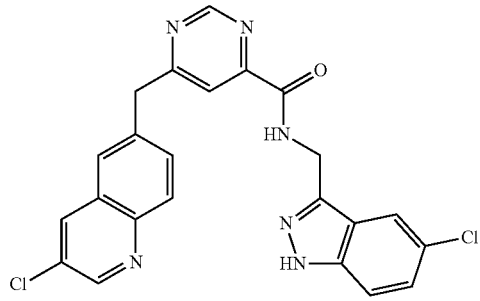 [SMILES: O=C(NCc1n[nH]c2ccc(Cl)cc12)c1cc(Cc2ccc3ncc(Cl)cc3c2)ncn1]

N-((5-chloro-1H-indazol-3-yl)methyl)-6-((3-chloroquinolin-6-yl)methyl)pyrimidine-4-carboxamide

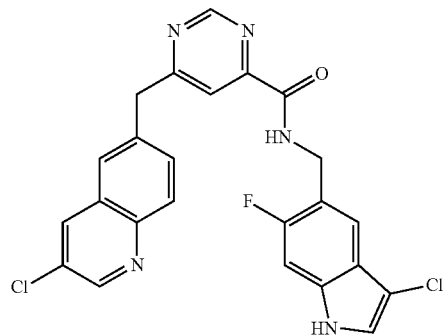

N-((3-chloro-6-fluoro-1H-indol-5-yl)methyl)-6-((3-chloroquinolin-6-yl)methyl)pyrimidine-4-carboxamide

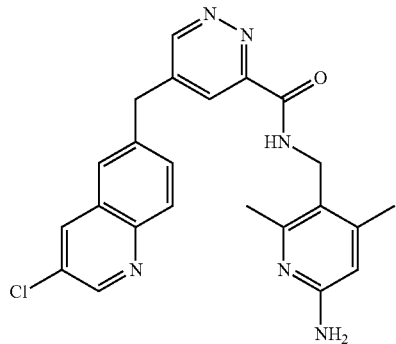 [SMILES: Cc1cc(N)nc(C)c1CNC(=O)c1cc(Cc2ccc3ncc(Cl)cc3c2)cnn1]

N-((6-amino-2,4-dimethylpyridin-3-yl)methyl)-5-((3-chloroquinolin-6-yl)methyl)pyridazine-3-carboxamide

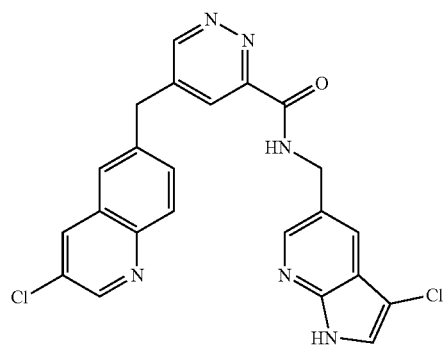 [SMILES: O=C(NCc1cnc2[nH]cc(Cl)c2c1)c1cc(Cc2ccc3ncc(Cl)cc3c2)cnn1]

N-((3-chloro-1H-pyrrolo[2,3-b]pyridin-5-yl)methyl)-5-((3-chloroquinolin-6-yl)methyl)pyridazine-3-carboxamide TABLE 2-continued

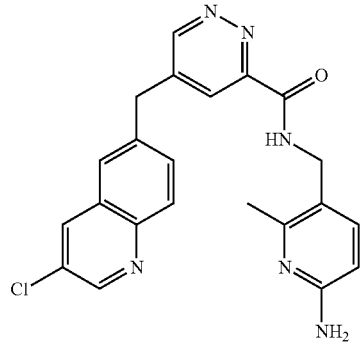 [SMILES: Cc1nc(N)ccc1CNC(=O)c1cc(Cc2ccc3ncc(Cl)cc3c2)cnn1]

N-((6-amino-2-methylpyridin-3-yl)methyl)-5-((3-chloroquinolin-6-yl)methyl)pyridazine-3-carboxamide

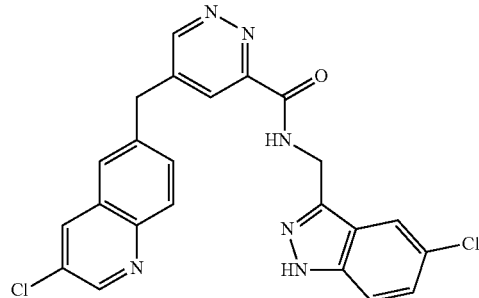

N-((5-chloro-1H-indazol-3-yl)methyl)-5-((3-chloroquinolin-6-yl)methyl)pyridazine-3-carboxamide

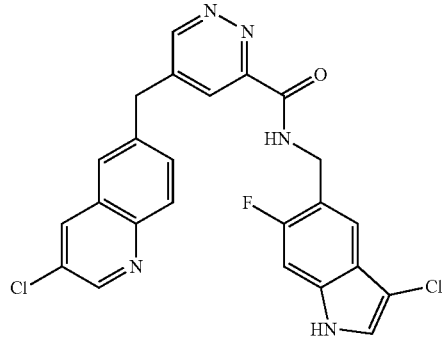 [SMILES: O=C(NCc1cc2c(Cl)c[nH]c2cc1F)c1cc(Cc2ccc3ncc(Cl)cc3c2)cnn1]

N-((3-chloro-6-fluoro-1H-indol-5-yl)methyl)-5-((3-chloroquinolin-6-yl)methyl)pyridazine-3-carboxamide

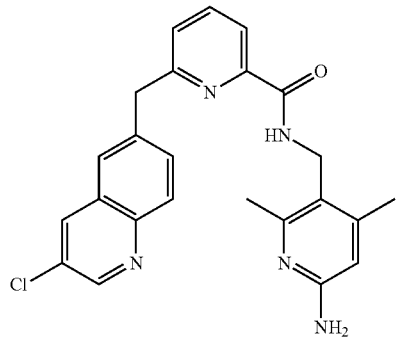 [SMILES: Cc1cc(N)nc(C)c1CNC(=O)c1cccc(Cc2ccc3ncc(Cl)cc3c2)n1]

N-((6-amino-2,4-dimethylpyridin-3-yl)methyl)-6-((3-chloroquinolin-6-yl)methyl)picolinamide TABLE 2-continued

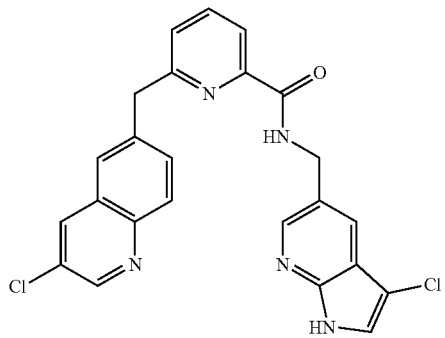 [SMILES: O=C(NCc1cnc2[nH]cc(Cl)c2c1)c1cccc(Cc2ccc3ncc(Cl)cc3c2)n1]

N-((3-chloro-1H-pyrrolo[2,3-b]pyridin-5-yl)methyl)-6-((3-chloroquinolin-6-yl)methyl)picolinamide

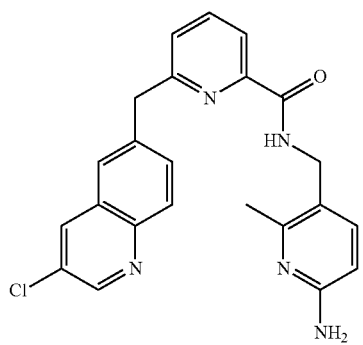 [SMILES: Cc1nc(N)ccc1CNC(=O)c1cccc(Cc2ccc3ncc(Cl)cc3c2)n1]

N-((6-amino-2-methylpyridin-3-yl)methyl)-6-((3-chloroquinolin-6-yl)methyl)picolinamide

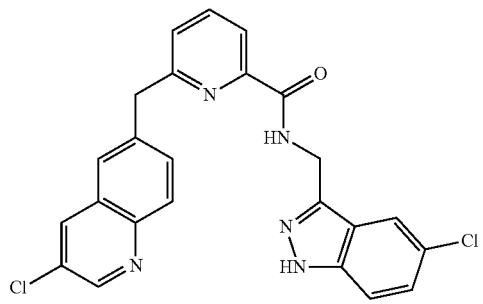 [SMILES: O=C(NCc1n[nH]c2ccc(Cl)cc12)c1cccc(Cc2ccc3ncc(Cl)cc3c2)n1]

N-((5-chloro-1H-indazol-3-yl)methyl)-6-((3-chloroquinolin-6-yl)methyl)picolinamide

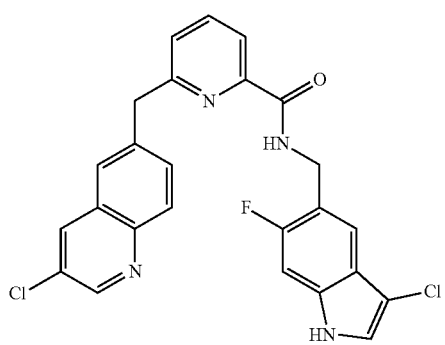 [SMILES: O=C(NCc1cc2c(Cl)c[nH]c2cc1F)c1cccc(Cc2ccc3ncc(Cl)cc3c2)n1]

N-((3-chloro-6-fluoro-1H-indol-5-yl)methyl)-6-((3-chloroquinolin-6-yl)methyl)picolinamide TABLE 2-continued

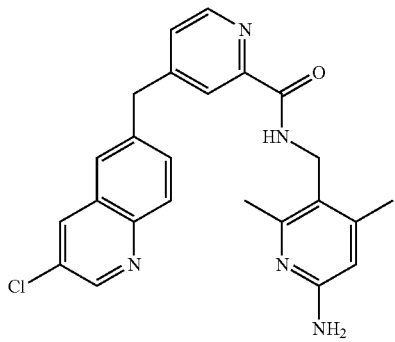 [SMILES: Cc1cc(N)nc(C)c1CNC(=O)c1cc(Cc2ccc3ncc(Cl)cc3c2)ccn1]

N-((6-amino-2,4-dimethylpyridin-3-yl)methyl)-4-((3-chloroquinolin-6-yl)methyl)picolinamide

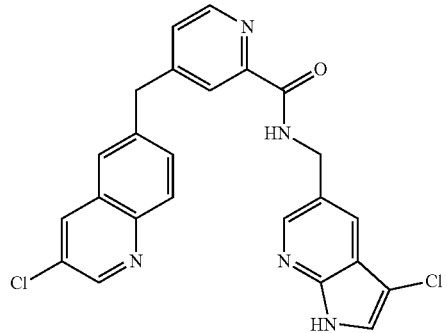 [SMILES: O=C(NCc1cnc2[nH]cc(Cl)c2c1)c1cc(Cc2ccc3ncc(Cl)cc3c2)ccn1]

N-((3-chloro-1H-pyrrolo[2,3-b]pyridin-5-yl)methyl)-4-((3-chloroquinolin-6-yl)methyl)picolinamide

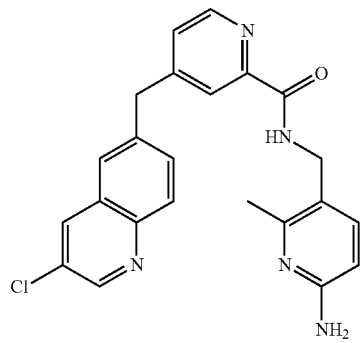 [SMILES: Cc1nc(N)ccc1CNC(=O)c1cc(Cc2ccc3ncc(Cl)cc3c2)ccn1]

N-((6-amino-2-methylpyridin-3-yl)methyl)-4-((3-chloroquinolin-6-yl)methyl)picolinamide

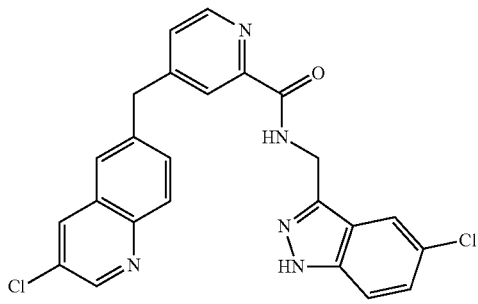 [SMILES: O=C(NCc1n[nH]c2ccc(Cl)cc12)c1cc(Cc2ccc3ncc(Cl)cc3c2)ccn1]

N-((5-chloro-1H-indazol-3-yl)methyl)-4-((3-chloroquinolin-6-yl)methyl)picolinamide TABLE 2-continued

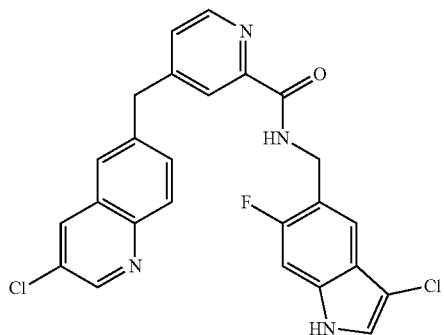 [SMILES: O=C(NCc1cc2c(Cl)c[nH]c2cc1F)c1cc(Cc2ccc3ncc(Cl)cc3c2)ccn1]

N-((3-chloro-6-fluoro-1H-indol-5-yl)methyl)-4-
((3-chloroquinolin-6-yl)methyl)picolinamide

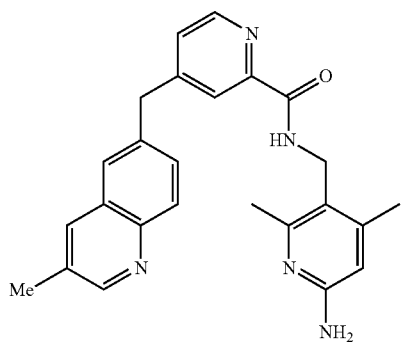 [SMILES: Cc1cnc2ccc(Cc3ccnc(C(=O)NCc4c(C)cc(N)nc4C)c3)cc2c1]

N-((6-amino-2,4-dimethylpyridin-3-yl)methyl)-4-
((3-methylquinolin-6-yl)methyl)picolinamide

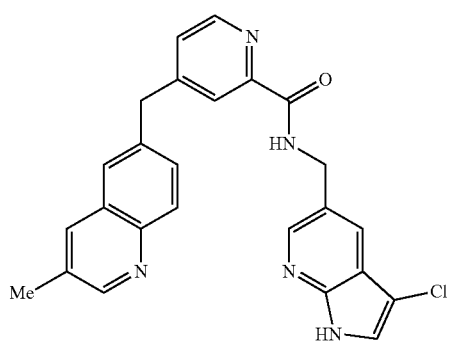 [SMILES: Cc1cnc2ccc(Cc3ccnc(C(=O)NCc4cnc5[nH]cc(Cl)c5c4)c3)cc2c1]

N-((3-chloro-1H-pyrrolo[2,3-b]pyridin-5-
yl)methyl)-4-((3-methylquinolin-6-
yl)methyl)picolinamide

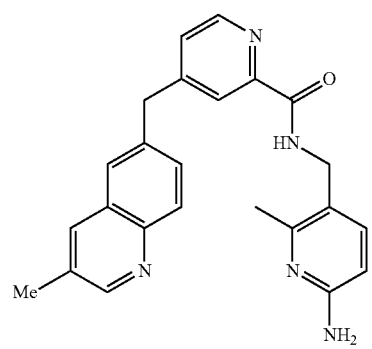 [SMILES: Cc1cnc2ccc(Cc3ccnc(C(=O)NCc4ccc(N)nc4C)c3)cc2c1]

N-((6-amino-2-methylpyridin-3-yl)methyl)-4-((3-
methylquinolin-6-yl)methyl)picolinamide TABLE 2-continued

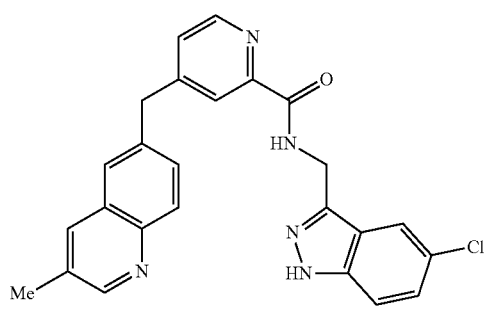

N-((5-chloro-1H-indazol-3-yl)methyl)-4-((3-
methylquinolin-6-yl)methyl)picolinamide

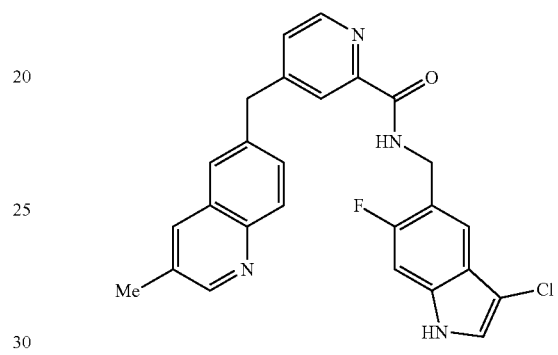

N-((3-chloro-6-fluoro-1H-indol-5-yl)methyl)-4-
((3-methylquinolin-6-yl)methyl)picolinamide

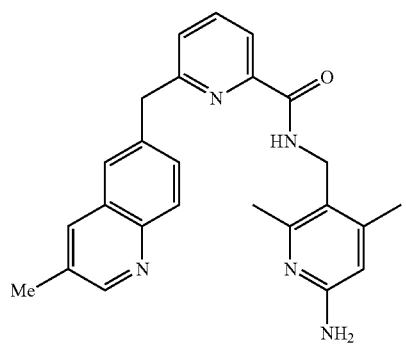

N-((6-amino-2,4-dimethylpyridin-3-yl)methyl)-6-
((3-methylquinolin-6-yl)methyl)picolinamide

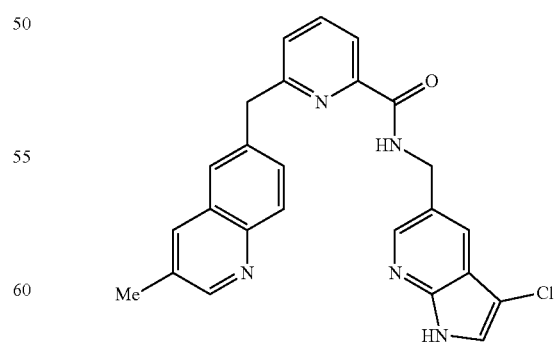

N-((3-chloro-1H-pyrrolo[2,3-b]pyridin-5-
yl)methyl)-6-((3-methylquinolin-6-
yl)methyl)picolinamide TABLE 2-continued

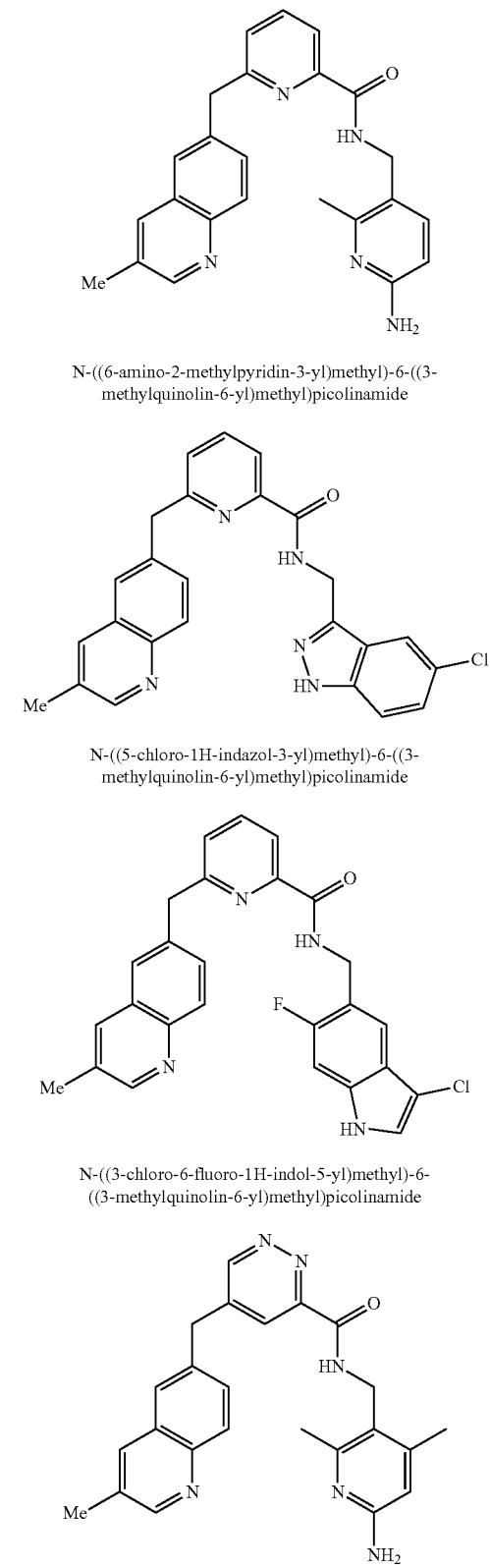

N-((6-amino-2-methylpyridin-3-yl)methyl)-6-((3-methylquinolin-6-yl)methyl)picolinamide N-((5-chloro-1H-indazol-3-yl)methyl)-6-((3-methylquinolin-6-yl)methyl)picolinamide N-((3-chloro-6-fluoro-1H-indol-5-yl)methyl)-6-((3-methylquinolin-6-yl)methyl)picolinamide N-((6-amino-2,4-dimethylpyridin-3-yl)methyl)-5-((3-methylquinolin-6-yl)methyl)pyridazine-3-carboxamide

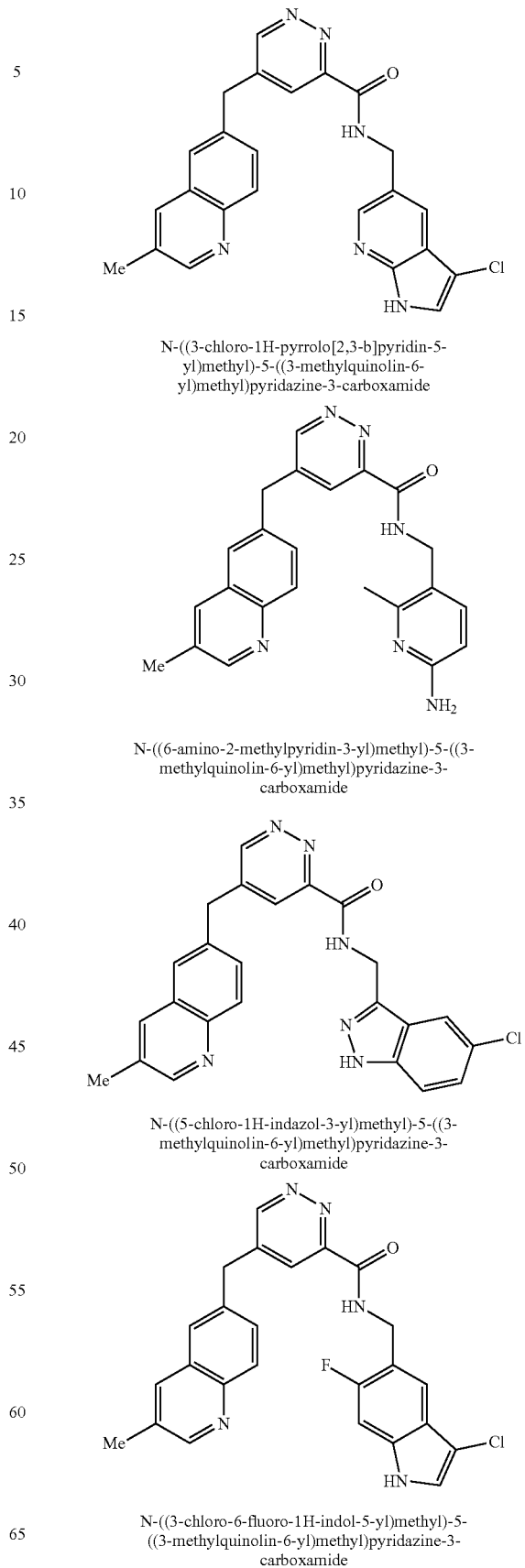

N-((3-chloro-1H-pyrrolo[2,3-b]pyridin-5-yl)methyl)-5-((3-methylquinolin-6-yl)methyl)pyridazine-3-carboxamide N-((6-amino-2-methylpyridin-3-yl)methyl)-5-((3-methylquinolin-6-yl)methyl)pyridazine-3-carboxamide N-((5-chloro-1H-indazol-3-yl)methyl)-5-((3-methylquinolin-6-yl)methyl)pyridazine-3-carboxamide N-((3-chloro-6-fluoro-1H-indol-5-yl)methyl)-5-((3-methylquinolin-6-yl)methyl)pyridazine-3-carboxamide TABLE 2-continued

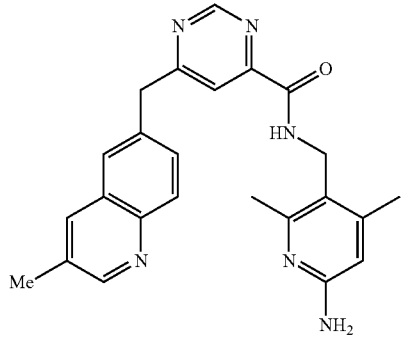

N-((6-amino-2,4-dimethylpyridin-3-yl)methyl)-6-
((3-methylquinolin-6-yl)methyl)pyrimidine-4-
carboxamide

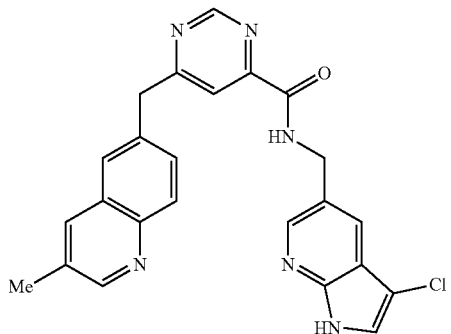 [SMILES: Cc1cnc2ccc(Cc3cc(C(=O)NCc4cnc5[nH]cc(Cl)c5c4)ncn3)cc2c1]

N-((3-chloro-1H-pyrrolo[2,3-b]pyridin-5-
yl)methyl)-6-((3-methylquinolin-6-
yl)methyl)pyrimidine-4-carboxamide

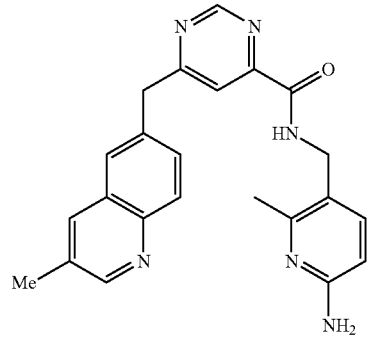

N-((6-amino-2-methylpyridin-3-yl)methyl)-6-((3-
methylquinolin-6-yl)methyl)pyrimidine-4-
carboxamide

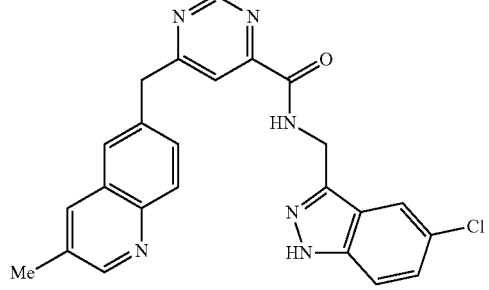

N-((5-chloro-1H-indazol-3-yl)methyl)-6-((3-
methylquinolin-6-yl)methyl)pyrimidine-4-
carboxamide TABLE 2-continued

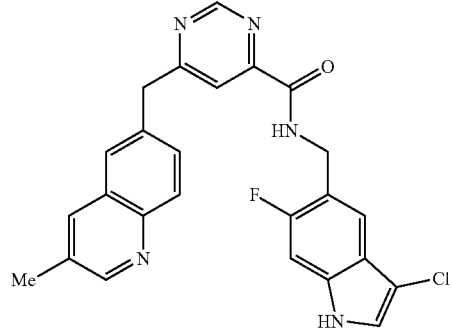 [SMILES: Cc1cnc2ccc(Cc3cc(C(=O)NCc4cc5c(Cl)c[nH]c5cc4F)ncn3)cc2c1]

N-((3-chloro-6-fluoro-1H-indol-5-yl)methyl)-6-
((3-methylquinolin-6-yl)methyl)pyrimidine-4-
carboxamide

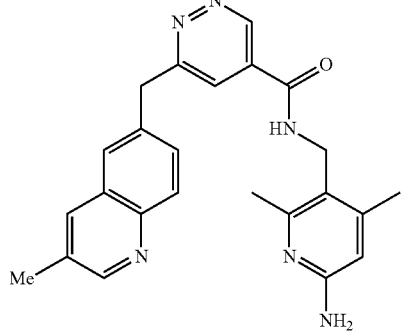

N-((6-amino-2,4-dimethylpyridin-3-yl)methyl)-6-
((3-methylquinolin-6-yl)methyl)pyridazine-4-
carboxamide

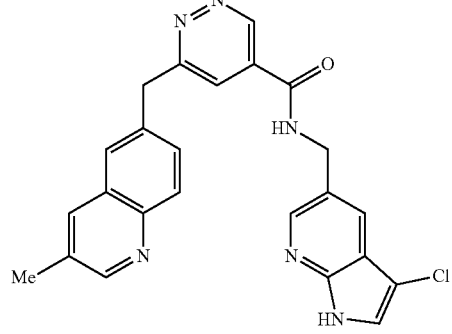

N-((3-chloro-1H-pyrrolo[2,3-b]pyridin-5-
yl)methyl)-6-((3-methylquinolin-6-
yl)methyl)pyridazine-4-carboxamide

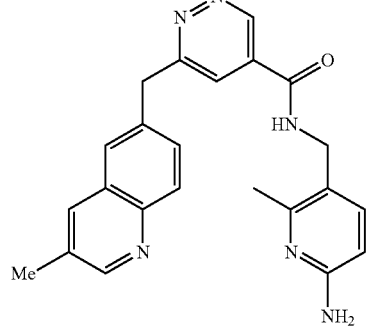

N-((6-amino-2-methylpyridin-3-yl)methyl)-6-((3-
methylquinolin-6-yl)methyl)pyridazine-4-
carboxamide TABLE 2-continued

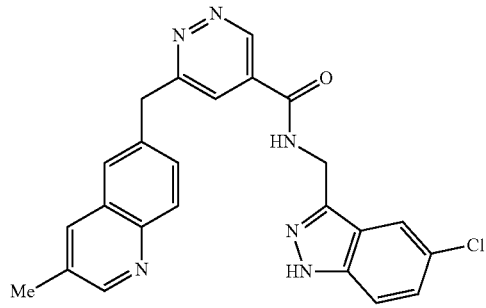 [SMILES: Cc1cnc2ccc(Cc3cc(C(=O)NCc4n[nH]c5ccc(Cl)cc45)cnn3)cc2c1]

N-((5-chloro-1H-indazol-3-yl)methyl)-6-((3-methylquinolin-6-yl)methyl)pyridazine-4-carboxamide

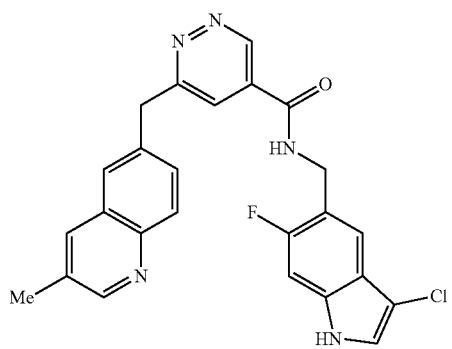 [SMILES: Cc1cnc2ccc(Cc3cc(C(=O)NCc4cc5c(Cl)c[nH]c5cc4F)cnn3)cc2c1]

N-((3-chloro-6-fluoro-1H-indol-5-yl)methyl)-6-((3-methylquinolin-6-yl)methyl)pyridazine-4-carboxamide

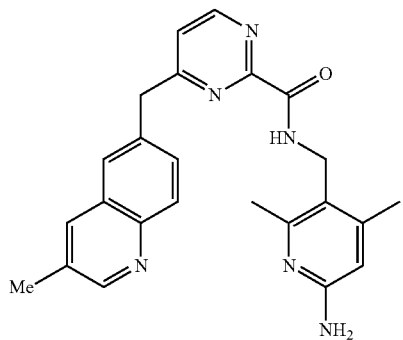 [SMILES: Cc1cnc2ccc(Cc3ccnc(C(=O)NCc4c(C)cc(N)nc4C)n3)cc2c1]

N-((6-amino-2,4-dimethylpyridin-3-yl)methyl)-4-((3-methylquinolin-6-yl)methyl)pyrimidine-2-carboxamide

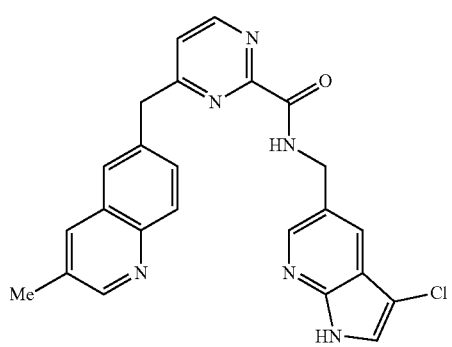

N-((3-chloro-1H-pyrrolo[2,3-b]pyridin-5-yl)methyl)-4-((3-methylquinolin-6-yl)methyl)pyrimidine-2-carboxamide TABLE 2-continued

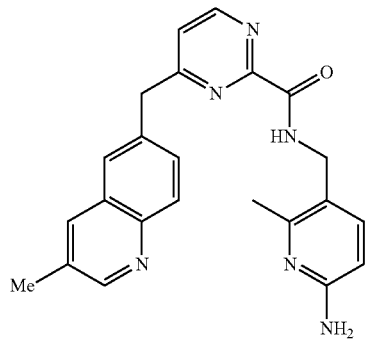 [SMILES: Cc1cnc2ccc(Cc3ccnc(C(=O)NCc4ccc(N)nc4C)n3)cc2c1]

N-((6-amino-2-methylpyridin-3-yl)methyl)-4-((3-methylquinolin-6-yl)methyl)pyrimidine-2-carboxamide

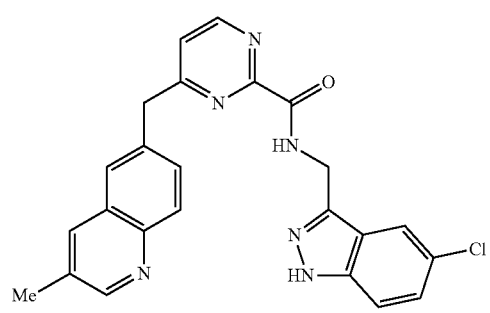 [SMILES: Cc1cnc2ccc(Cc3ccnc(C(=O)NCc4n[nH]c5ccc(Cl)cc45)n3)cc2c1]

N-((5-chloro-1H-indazol-3-yl)methyl)-4-((3-methylquinolin-6-yl)methyl)pyrimidine-2-carboxamide

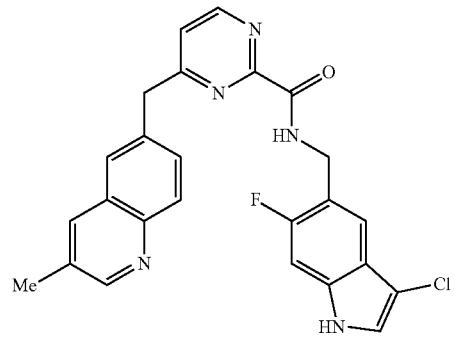

N-((3-chloro-6-fluoro-1H-indol-5-yl)methyl)-4-((3-methylquinolin-6-yl)methyl)pyrimidine-2-carboxamide

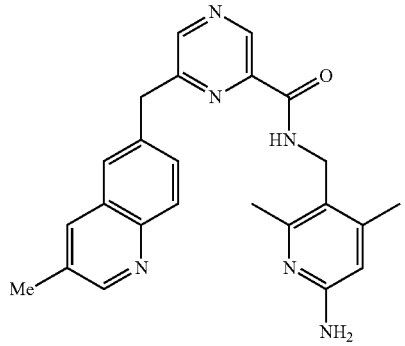 [SMILES: Cc1cnc2ccc(Cc3cncc(C(=O)NCc4c(C)cc(N)nc4C)n3)cc2c1]

N-((6-amino-2,4-dimethylpyridin-3-yl)methyl)-6-((3-methylquinolin-6-yl)methyl)pyrazine-2-carboxamide TABLE 2-continued

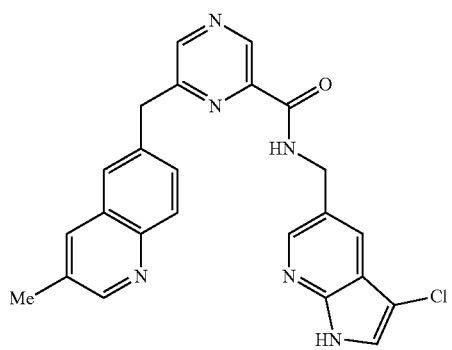 [SMILES: Cc1cnc2ccc(Cc3cncc(C(=O)NCc4cnc5[nH]cc(Cl)c5c4)n3)cc2c1]

N-((3-chloro-1H-pyrrolo[2,3-b]pyridin-5-yl)methyl)-6-((3-methylquinolin-6-yl)methyl)pyrazine-2-carboxamide

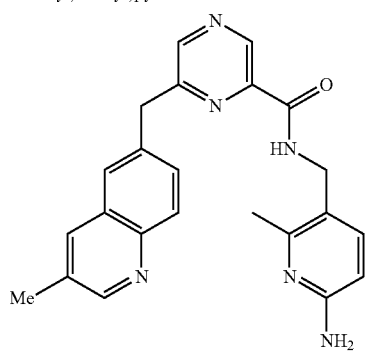

N-((6-amino-2-methylpyridin-3-yl)methyl)-6-((3-methylquinolin-6-yl)methyl)pyrazine-2-carboxamide

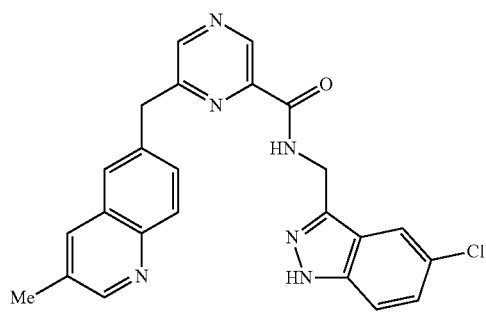 [SMILES: Cc1cnc2ccc(Cc3cncc(C(=O)NCc4n[nH]c5ccc(Cl)cc45)n3)cc2c1]

N-((5-chloro-1H-indazol-3-yl)methyl)-6-((3-methylquinolin-6-yl)methyl)pyrazine-2-carboxamide

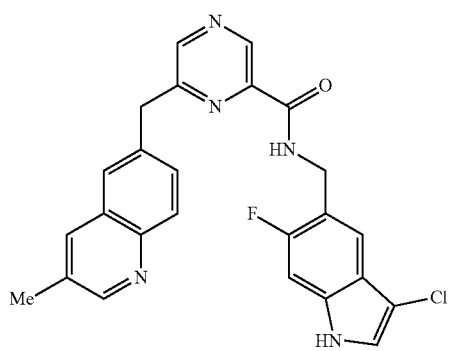 [SMILES: Cc1cnc2ccc(Cc3cncc(C(=O)NCc4cc5c(Cl)c[nH]c5cc4F)n3)cc2c1]

N-((3-chloro-6-fluoro-1H-indol-5-yl)methyl)-6-((3-methylquinolin-6-yl)methyl)pyrazine-2-carboxamide TABLE 2-continued

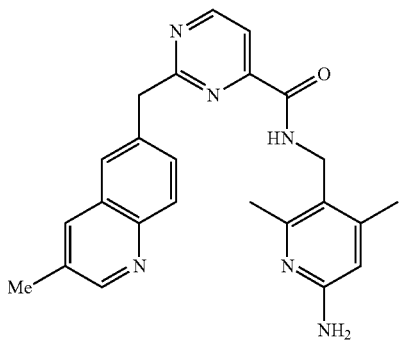 [SMILES: Cc1cnc2ccc(Cc3nccc(C(=O)NCc4c(C)cc(N)nc4C)n3)cc2c1]

N-((6-amino-2,4-dimethylpyridin-3-yl)methyl)-2-((3-methylquinolin-6-yl)methyl)pyrimidine-4-carboxamide

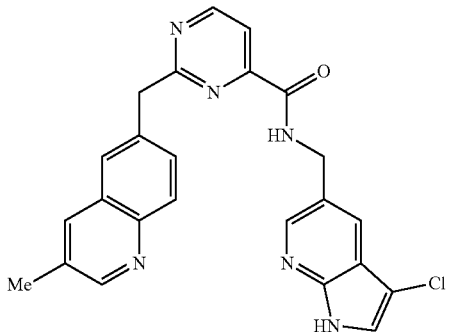 [SMILES: Cc1cnc2ccc(Cc3nccc(C(=O)NCc4cnc5[nH]cc(Cl)c5c4)n3)cc2c1]

N-((3-chloro-1H-pyrrolo[2,3-b]pyridin-5-yl)methyl)-2-((3-methylquinolin-6-yl)methyl)pyrimidine-4-carboxamide

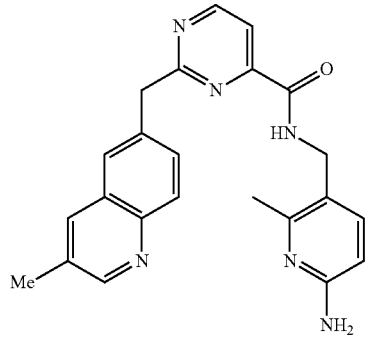 [SMILES: Cc1cnc2ccc(Cc3nccc(C(=O)NCc4ccc(N)nc4C)n3)cc2c1]

N-((6-amino-2-methylpyridin-3-yl)methyl)-2-((3-methylquinolin-6-yl)methyl)pyrimidine-4-carboxamide

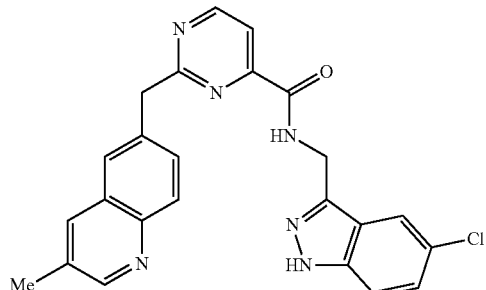

N-((5-chloro-1H-indazol-3-yl)methyl)-2-((3-methylquinolin-6-yl)methyl)pyrimidine-4-carboxamide TABLE 2-continued

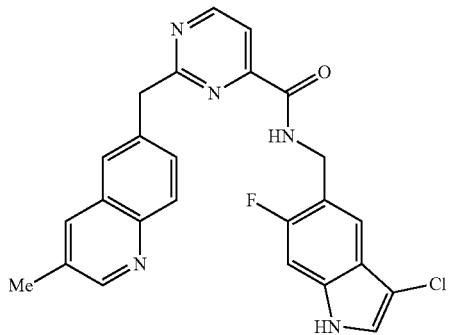 [SMILES: Cc1cnc2ccc(Cc3nccc(C(=O)NCc4cc5c(Cl)c[nH]c5cc4F)n3)cc2c1]

N-((3-chloro-6-fluoro-1H-indol-5-yl)methyl)-2-
((3-methylquinolin-6-yl)methyl)pyrimidine-4-
carboxamide

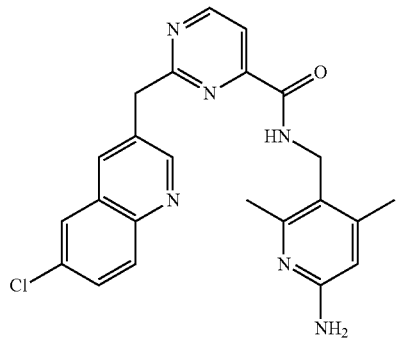 [SMILES: Cc1cc(N)nc(C)c1CNC(=O)c1ccnc(Cc2cnc3ccc(Cl)cc3c2)n1]

N-((6-amino-2,4-dimethylpyridin-3-yl)methyl)-2-
((6-chloroquinolin-3-yl)methyl)pyrimidine-4-
carboxamide

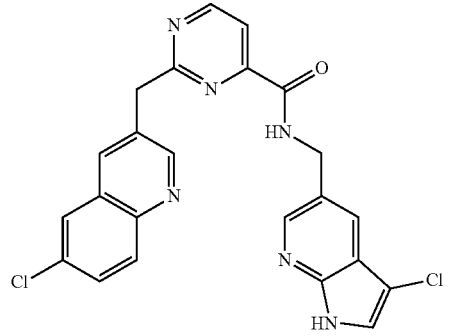

N-((3-chloro-1H-pyrrolo[2,3-b]pyridin-5-
yl)methyl)-2-((6-chloroquinolin-3-
yl)methyl)pyrimidine-4-carboxamide

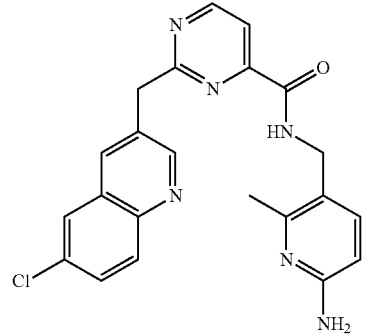 [SMILES: Cc1nc(N)ccc1CNC(=O)c1ccnc(Cc2cnc3ccc(Cl)cc3c2)n1]

N-((6-amino-2-methylpyridin-3-yl)methyl)-2-((6-
chloroquinolin-3-yl)methyl)pyrimidine-4-
carboxamide TABLE 2-continued

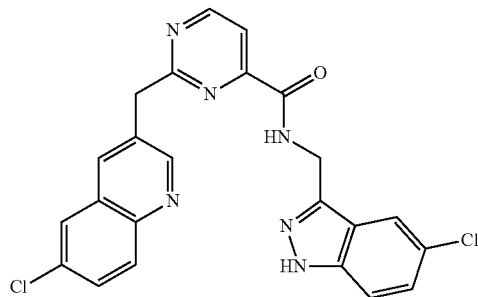 [SMILES: O=C(NCc1n[nH]c2ccc(Cl)cc12)c1ccnc(Cc2cnc3ccc(Cl)cc3c2)n1]

N-((5-chloro-1H-indazol-3-yl)methyl)-2-((6-
chloroquinolin-3-yl)methyl)pyrimidine-4-
carboxamide

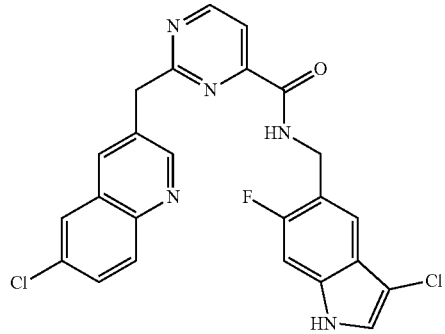 [SMILES: O=C(NCc1cc2c(Cl)c[nH]c2cc1F)c1ccnc(Cc2cnc3ccc(Cl)cc3c2)n1]

N-((3-chloro-6-fluoro-1H-indol-5-yl)methyl)-2-
((6-chloroquinolin-3-yl)methyl)pyrimidine-4-
carboxamide

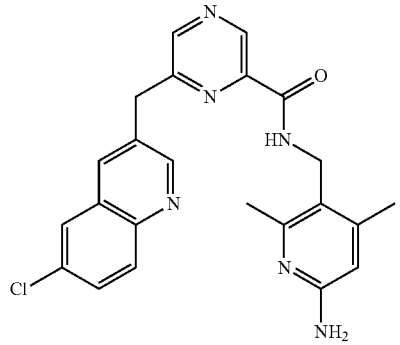 [SMILES: Cc1cc(N)nc(C)c1CNC(=O)c1cncc(Cc2cnc3ccc(Cl)cc3c2)n1]

N-((6-amino-2,4-dimethylpyridin-3-yl)methyl)-6-
((6-chloroquinolin-3-yl)methyl)pyrazine-2-
carboxamide

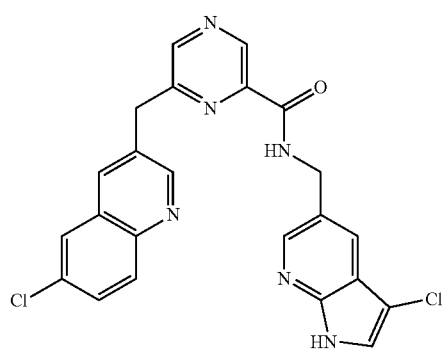 [SMILES: O=C(NCc1cnc2[nH]cc(Cl)c2c1)c1cncc(Cc2cnc3ccc(Cl)cc3c2)n1]

N-((3-chloro-1H-pyrrolo[2,3-b]pyridin-5-
yl)methyl)-6-((6-chloroquinolin-3-
yl)methyl)pyrazine-2-carboxamide TABLE 2-continued

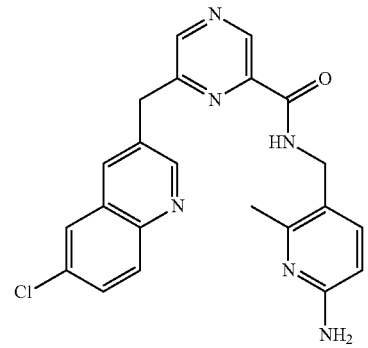 [SMILES: Cc1nc(N)ccc1CNC(=O)c1cncc(Cc2cnc3ccc(Cl)cc3c2)n1]

N-((6-amino-2-methylpyridin-3-yl)methyl)-6-((6-chloroquinolin-3-yl)methyl)pyrazine-2-carboxamide

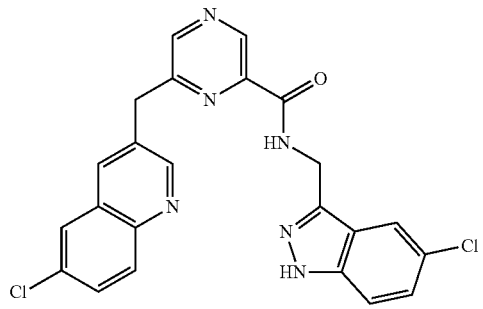 [SMILES: O=C(NCc1n[nH]c2ccc(Cl)cc12)c1cncc(Cc2cnc3ccc(Cl)cc3c2)n1]

N-((5-chloro-1H-indazol-3-yl)methyl)-6-((6-chloroquinolin-3-yl)methyl)pyrazine-2-carboxamide

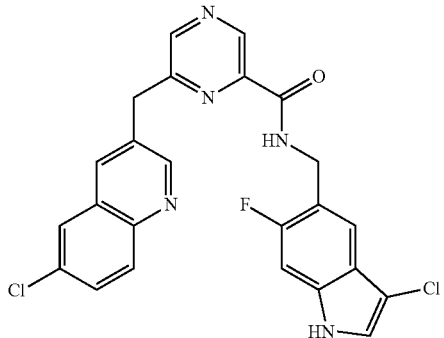 [SMILES: O=C(NCc1cc2c(Cl)c[nH]c2cc1F)c1cncc(Cc2cnc3ccc(Cl)cc3c2)n1]

N-((3-chloro-6-fluoro-1H-indol-5-yl)methyl)-6-((6-chloroquinolin-3-yl)methyl)pyrazine-2-carboxamide

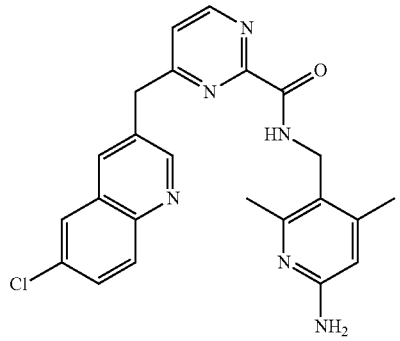

N-((6-amino-2,4-dimethylpyridin-3-yl)methyl)-4-((6-chloroquinolin-3-yl)methyl)pyrimidine-2-carboxamide TABLE 2-continued

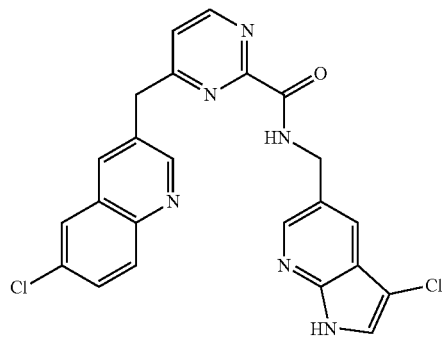 [SMILES: O=C(NCc1cnc2[nH]cc(Cl)c2c1)c1nccc(Cc2cnc3ccc(Cl)cc3c2)n1]

N-((3-chloro-1H-pyrrolo[2,3-b]pyridin-5-yl)methyl)-4-((6-chloroquinolin-3-yl)methyl)pyrimidine-2-carboxamide

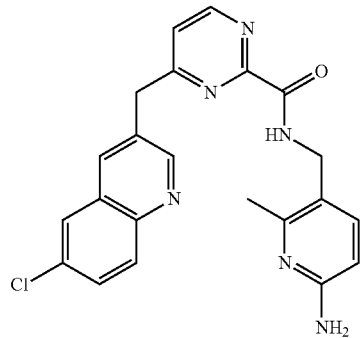 [SMILES: Cc1nc(N)ccc1CNC(=O)c1nccc(Cc2cnc3ccc(Cl)cc3c2)n1]

N-((6-amino-2-methylpyridin-3-yl)methyl)-4-((6-chloroquinolin-3-yl)methyl)pyrimidine-2-carboxamide

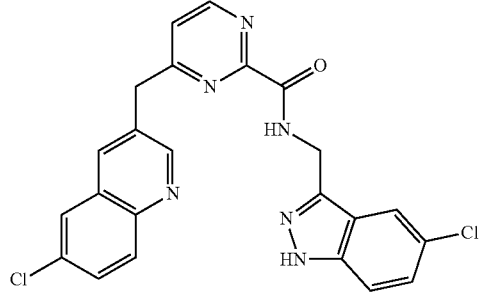 [SMILES: O=C(NCc1n[nH]c2ccc(Cl)cc12)c1nccc(Cc2cnc3ccc(Cl)cc3c2)n1]

N-((5-chloro-1H-indazol-3-yl)methyl)-4-((6-chloroquinolin-3-yl)methyl)pyrimidine-2-carboxamide

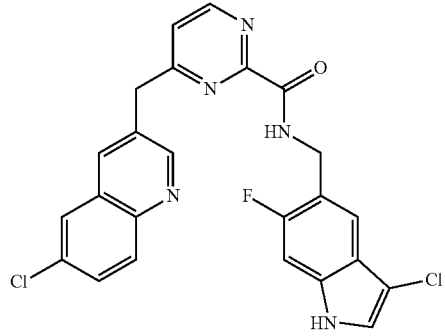 [SMILES: O=C(NCc1cc2c(Cl)c[nH]c2cc1F)c1nccc(Cc2cnc3ccc(Cl)cc3c2)n1]

N-((3-chloro-6-fluoro-1H-indol-5-yl)methyl)-4-((6-chloroquinolin-3-yl)methyl)pyrimidine-2-carboxamide TABLE 2-continued

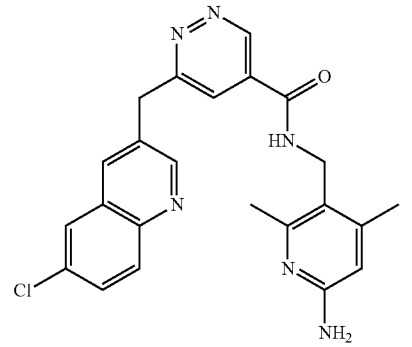 [SMILES: Cc1cc(N)nc(C)c1CNC(=O)c1cnnc(Cc2cnc3ccc(Cl)cc3c2)c1]

N-((6-amino-2,4-dimethylpyridin-3-yl)methyl)-6-
((6-chloroquinolin-3-yl)methyl)pyridazine-4-
carboxamide

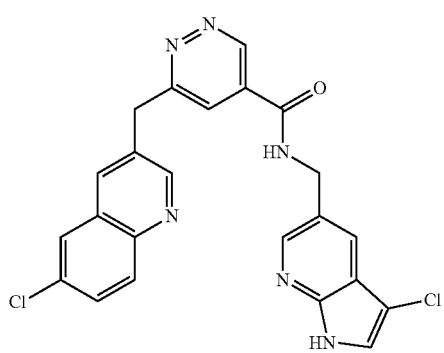 [SMILES: O=C(NCc1cnc2[nH]cc(Cl)c2c1)c1cnnc(Cc2cnc3ccc(Cl)cc3c2)c1]

N-((3-chloro-1H-pyrrolo[2,3-b]pyridin-5-
yl)methyl)-6-((6-chloroquinolin-3-
yl)methyl)pyridazine-4-carboxamide

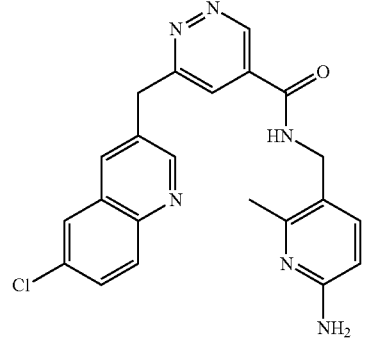 [SMILES: Cc1nc(N)ccc1CNC(=O)c1cnnc(Cc2cnc3ccc(Cl)cc3c2)c1]

N-((6-amino-2-methylpyridin-3-yl)methyl)-6-((6-
chloroquiolin-3-yl)methyl)pyridazine-4-
carboxamide

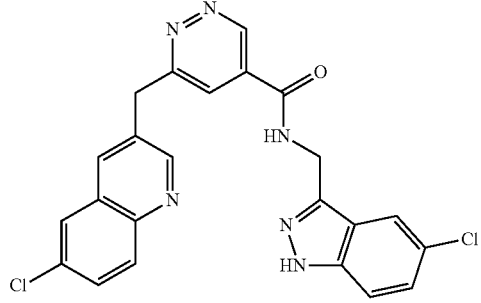 [SMILES: O=C(NCc1n[nH]c2ccc(Cl)cc12)c1cnnc(Cc2cnc3ccc(Cl)cc3c2)c1]

N-((5-chloro-1H-indazol-3-yl)methyl)-6-((6-
chloroquinolin-3-yl)methyl)pyridazine-4-
carboxamide TABLE 2-continued

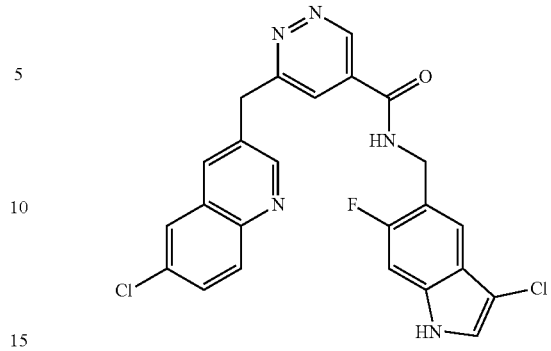

N-((3-chloro-6-fluoro-1H-indol-5-yl)methyl)-6-
((6-chloroquinolin-3-yl)methyl)pyridazine-4-
carboxamide

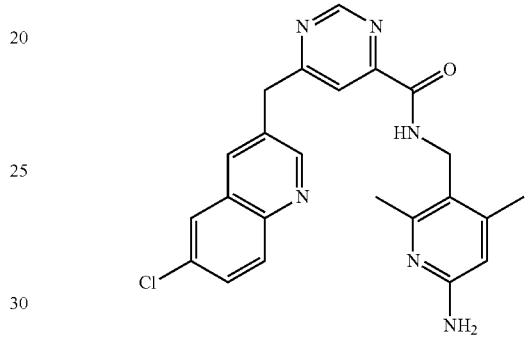

N-((6-amino-2,4-dimethylpyridin-3-yl)methyl)-6-
((6-chloroquinolin-3-yl)methyl)pyrimidine-4-
carboxamide

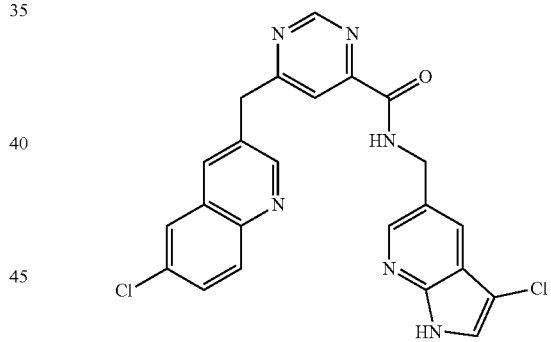

N-((3-chloro-1H-pyrrolo[2,3-b]pyridin-5-
yl)methyl)-6-((6-chloroquinolin-3-
yl)methyl)pyrimidine-4-carboxamide

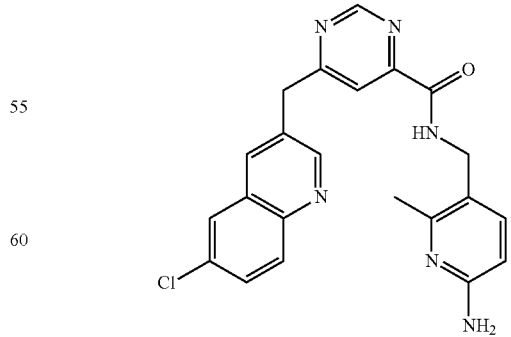

N-((6-amino-2-methylpyridin-3-yl)methyl)-6-((6-
chloroquinolin-3-yl)methyl)pyrimidine-4-
carboxamide TABLE 2-continued

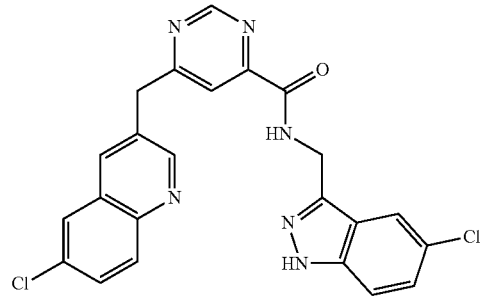 [SMILES: O=C(NCc1n[nH]c2ccc(Cl)cc12)c1cc(Cc2cnc3ccc(Cl)cc3c2)ncn1]

N-((5-chloro-1H-indazol-3-yl)methyl)-6-((6-chloroquinolin-3-yl)methyl)pyrimidine-4-carboxamide

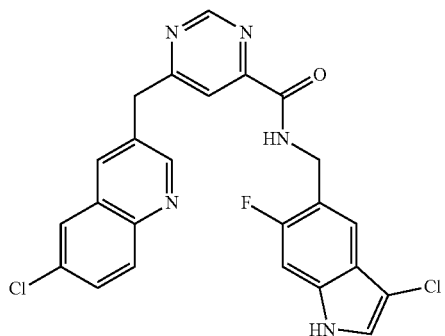 [SMILES: O=C(NCc1cc2c(Cl)c[nH]c2cc1F)c1cc(Cc2cnc3ccc(Cl)cc3c2)ncn1]

N-((3-chloro-6-fluoro-1H-indol-5-yl)methyl)-6-((6-chloroquinolin-3-yl)methyl)pyrimidine-4-carboxamide

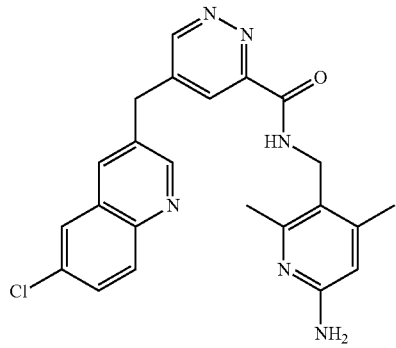 [SMILES: Cc1cc(N)nc(C)c1CNC(=O)c1cc(Cc2cnc3ccc(Cl)cc3c2)cnn1]

N-((6-amino-2,4-dimethylpyridin-3-yl)methyl)-5-((6-chloroquinolin-3-yl)methyl)pyridazine-3-carboxamide

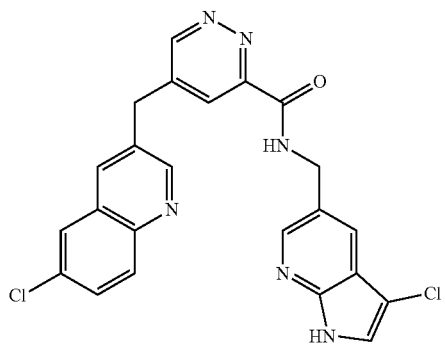 [SMILES: O=C(NCc1cnc2[nH]cc(Cl)c2c1)c1cc(Cc2cnc3ccc(Cl)cc3c2)cnn1]

N-((3-chloro-1H-pyrrolo[2,3-b]pyridin-5-yl)methyl)-5-((6-chloroquinolin-3-yl)methyl)pyridazine-3-carboxamide TABLE 2-continued

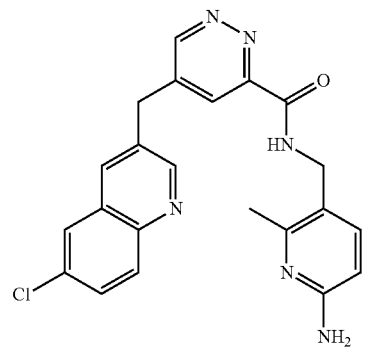 [SMILES: Cc1nc(N)ccc1CNC(=O)c1cc(Cc2cnc3ccc(Cl)cc3c2)cnn1]

N-((6-amino-2-methylpyridin-3-yl)methyl)-5-((6-chloroquinolin-3-yl)methyl)pyridazine-3-carboxamide

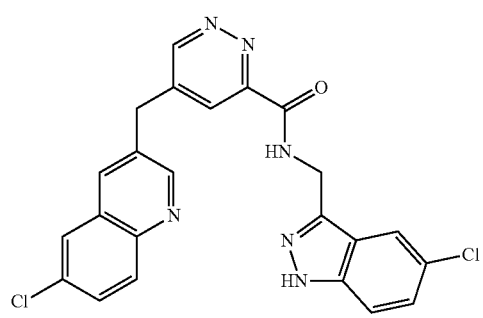 [SMILES: O=C(NCc1n[nH]c2ccc(Cl)cc12)c1cc(Cc2cnc3ccc(Cl)cc3c2)cnn1]

N-((5-chloro-1H-indazol-3-yl)methyl)-5-((6-chloroquinolin-3-yl)methyl)pyridazine-3-carboxamide

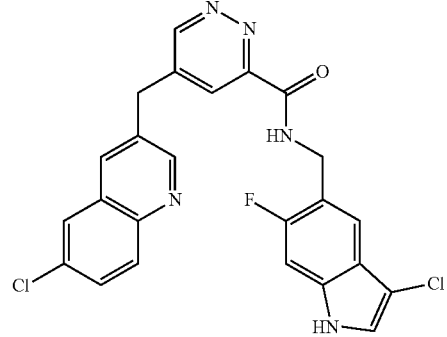 [SMILES: O=C(NCc1cc2c(Cl)c[nH]c2cc1F)c1cc(Cc2cnc3ccc(Cl)cc3c2)cnn1]

N-((3-chloro-6-fluoro-1H-indol-5-yl)methyl)-5-((6-chloroquinolin-3-yl)methyl)pyridazine-3-carboxamide

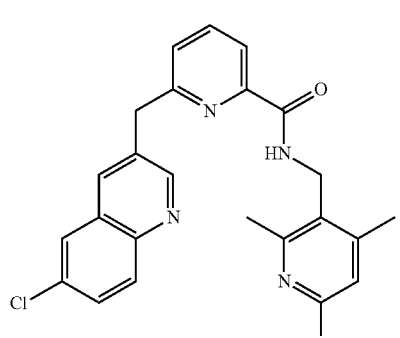

N-((6-amino-2,4-dimethylpyridin-3-yl)methyl)-6-((6-chloroquinolin-3-yl)methyl)picolinamide TABLE 2-continued

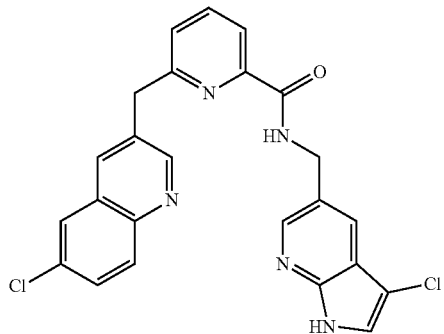

N-((3-chloro-1H-pyrrolo[2,3-b]pyridin-5-yl)methyl)-6-((6-chloroquinolin-3-yl)methyl)picolinamide

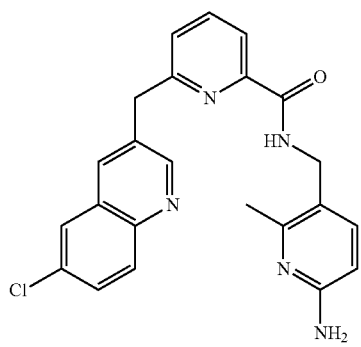

N-((6-amino-2-methylpyridin-3-yl)methyl)-6-((6-chloroquinolin-3-yl)methyl)picolinamide

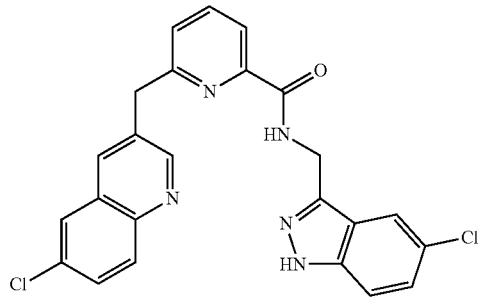 [SMILES: O=C(NCc1n[nH]c2ccc(Cl)cc12)c1cccc(Cc2cnc3ccc(Cl)cc3c2)n1]

N-((5-chloro-1H-indazol-3-yl)methyl)-6-((6-chloroquinolin-3-yl)methyl)picolinamide

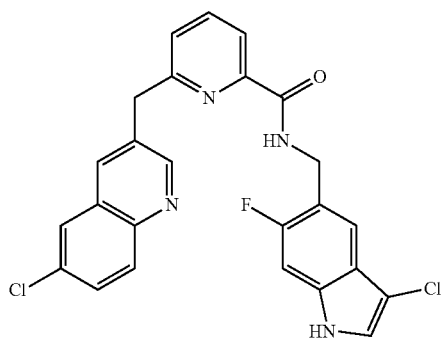

N-((3-chloro-6-fluoro-1H-indol-5-yl)methyl)-6-((6-chloroquinolin-3-yl)methyl)picolinamide TABLE 2-continued

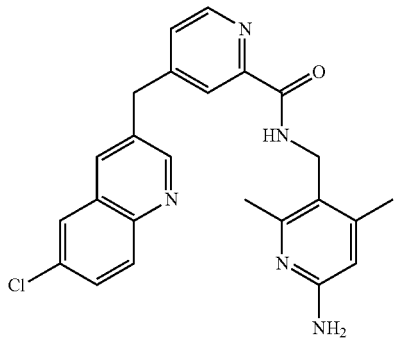

N-((6-amino-2,4-dimethylpyridin-3-yl)methyl)-4-((6-chloroquinolin-3-yl)methyl)picolinamide

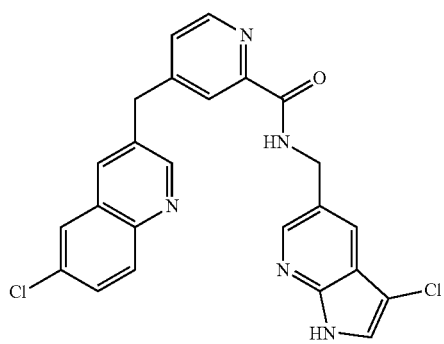

N-((3-chloro-1H-pyrrolo[2,3-b]pyridin-5-yl)methyl)-4-((6-chloroquinolin-3-yl)methyl)picolinamide

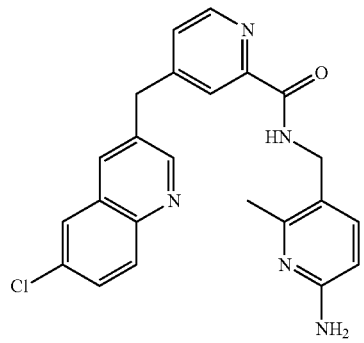

N-((6-amino-2-methylpyridin-3-yl)methyl)-4-((6 chloroquinolin-3-yl)methyl)picolinamide

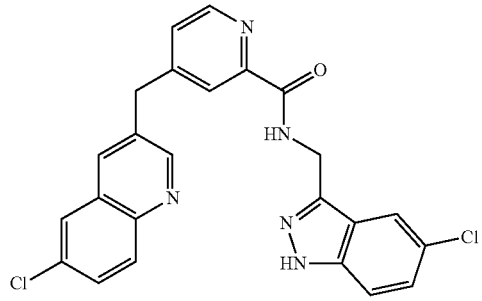 [SMILES: O=C(NCc1n[nH]c2ccc(Cl)cc12)c1cc(Cc2cnc3ccc(Cl)cc3c2)ccn1]

N-((5-chloro-1H-indazol-3-yl)methyl)-4-((6-chloroquinolin-3-yl)methyl)picolinamide

TABLE 2-continued

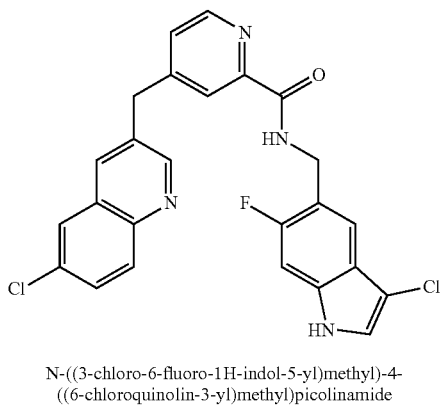

N-((3-chloro-6-fluoro-1H-indol-5-yl)methyl)-4-
((6-chloroquinolin-3-yl)methyl)picolinamide Preparation of Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the kallikrein inhibitory compound described herein is P. H. Stahl & C. G. Wermuth "Handbook of Pharmaceutical Salts", Verlag Helvetica Chimica Acta, Zurich, 2002.

Pharmaceutical Compositions

In certain embodiments, the kallikrein inhibitory compound as described herein is administered as a pure chemical. In other embodiments, the kallikrein inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one kallikrein inhibitory compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (II), or a pharmaceutically acceptable salt thereof, and a pharmaceutically acceptable excipient.

In certain embodiments, the kallikrein inhibitory compound as described by Formula (I) or (II) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

The dose of the composition comprising at least one kallikrein inhibitory compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Kallikrein-Kinin System

Modulation of vascular permeability is important in regulating the passage of small molecules or blood cells between blood vessels and surrounding tissues. Vascular permeability depends upon the physiological states of tissues such as during inflammation, changes in blood pressure, and fluctuations in ion and nutrient gradients. The junctions between the endothelial cells that line blood vessels are the immediate controllers of vascular permeability. The strength of these junctions is tightly regulated by the kinin-kallikrein system of polypeptides and enzymes. Abnormalities in the kinin-kallikrein system lead to a range of pathologies including angioedema, macular edema and brain edema. Angioedema is a potentially fatal blood disorder characterized by swelling that may occur in the face, gastrointestinal tract, extremities, genitals and upper airways. Genetic hereditary angioedema attacks result from the unregulated activation of the kallikrein system with uncontrolled increases in vascular permeability. Currently there is a need for agents that are useful for the treatment of angioedema and for agents that inhibit plasma kallikrein.

The kallikrein-kinin system represents a metabolic cascade that, when activated, triggers the release of vasoactive kinins. The kinin-kallikrein system (KKS) consists of serine proteases involved in the production of kinins, principally bradykinin and Lys-bradykinin (kallidin). The KKS contributes to a variety of physiological processes including inflammation, blood pressure control and coagulation. The activation of this system is particularly important in blood pressure regulation and in inflammatory reactions, due to the ability of bradykinin to elevate vascular permeability and to cause vasodilatation of arteries and veins of the gut, aorta, uterus and urethra. The kinin-kallikrein system, also referred to as the contact system, consists of three serine proenzymes (factor XII (FXII) or Hageman factor, factor IX (FIX), and prekallikrein), and the kinin precursor high molecular weight kinin (HK). Contact activation is triggered by the binding of FXII to a negatively charged surface and involves the formation of α-FXIIa via autocatalysis. Bound α-FXIIa converts prekallikrein into kallikrein. Kallikrein can further convert α-FXIIa to β-FXIIa by an additional cleavage at R334-N335, a positive feedback mechanism that leads to sufficient kallikrein production to drive downstream processes. α-FXIIa consists of a heavy and light chain that are disulphide linked, whereas β-FXIIa lacks the heavy chain and loses its capacity to bind to negatively charged surfaces (Stavrou E, Schmaier A H., Thrombosis Research, 2010, 125(3) pp. 210-215). The N-terminal region of FXII (α-FXIIa heavy chain) shows strong homology with tissue-type plasminogen activator (tPA), with the presence of fibronectin type I, epidermal growth factor, and Kringle domains (Ny et al., Proc Natl Acad Sci USA, 1984, 81(17) pp. 5355-5359; Cool D E, MacGillivray R T, The Journal of Biological Chemistry, 1987, 262(28) pp. 13662-13673). Kallikrein is a trypsin-like serine protease enzyme that cleaves high molecular weight kinin (HK) to produce bradykinin. Bradykinin then binds to the bradykinin 2R receptors (BK2R) on endothelial cells to trigger an increase in vascular permeability.

Protease inhibitors regulate the activation of the contact system. Several known serpins of plasma are C1-inhibitor (C1INH), antithrombin III, α2-macroglobulin, α1-protease inhibitor, and α2-antiplasmin (Kaplan et al., Advances in Immunology, 1997 (66) pp. 225-72; Pixley et al., The Journal of Biological Chemistry, 1985, 260(3) pp. 1723-9). However, C1INH is the major regulator of the intrinsic system, interfering with the activities of factor XIIa and of kallikrein (Cugno et al., The Journal of Laboratory and Clinical Medicine, 1993, 121(1) pp. 38-43). Both C1INH and α2-macroglobulin account for more than 90% of the kallikrein inhibitory activity of plasma. Thus, the FXII-dependent kallikrein-kinin system is tightly regulated by the C1NH and when regulation of the FXII-dependent kallikrein-kinin system fails, in a subject, the subject is believed to suffer from hereditary angioedema (HAE) that is characterized by invalidating edema attacks.

Angioedema is a potentially fatal blood disorder characterized by swelling that may occur in the face, gastrointestinal tract, extremities, genitals and upper airways. Angioedema attacks begin in the deeper layers of the skin and mucous membranes with localized blood vessel dilatation and increased permeability. Symptoms of the disease result from the leakage of plasma from blood vessels into surrounding tissues. Genetic hereditary angioedema attacks result from unregulated activation of the kallikrein system with consequent overproduction of bradykinin and uncontrolled increases in vascular permeability. As vascular permeability rises beyond normal, plasma leaks out of the vasculature into surrounding tissue, causing swelling (Mehta D and Malik A B, Physiol. Rev., 86 (1), 279-367, 2006; Sandoval R et al., J. Physiol., 533(pt 2), 433-45, 2001; Kaplan A P and Greaves M W, Angioedema. J Am. Acad. Dermatol., 2005).

HAE results from mutations in the genes that code for elements of the coagulation and inflammation pathways. The three forms of HAE are distinguished by their underlying causes and levels of the C1-esterase inhibitor (C1INH, serpin peptidase inhibitor, clade G, member 1) protein in the blood, which inhibits the activity of plasma kallikrein. In type I, patients have insufficient levels of functional C1INH, while type II patients have dysfunctional C1INH. While type I and II affect men and women at equal rates, type III, which primarily affects women, results from a mutation in coagulation factor XII (Hageman factor; HAE-FXII). The underlying causes of type I and II HAE are autosomal dominant mutations in C1INH gene (SERPING1 gene) on chromosome 11 (11q12-q13.1).

C1INH accounts for 90% of inhibition of FXIIa and 50% of inhibition of plasma kallikrein (Pixley R A et al., *J Biol. Chem.*, 260, 1723-9, 1985; Schapira M et al., *Biochemistry*, 20, 2738-43, 1981). In addition, C1INH also inactivates prekallikrein (Colman R W et al, *Blood*, 65, 311-8, 1985). When C1INH levels are normal, its activity blocks FXIIa from converting pre-kallikrein to kallikrein and blocks kallikrein's conversion to HK, thus preventing the production of bradykinin and the edemic episodes. When C1INH levels are low, or levels of dysfunctional C1INH are high, this inhibition fails and the pathogenic process ensues.

In addition to HAE, plasma kallikrein also contributes to non-hereditary angioedema, high altitude cerebral edema, cytotoxic cerebral edema, osmotic cerebral edema, diabetic macular edema (DME), clinically significant macular edema, cystoid macular edema (CME, Gao B B, *Nat Med.*, 13(2), 181-8, 2007), retinal edema, radiation induced edema, lymph edema, glioma-associated edema, allergic edema e.g. airflow obstruction in chronic allergic sinusitis or perennial rhinitis. Other disorders of the plasma kallikrein system include retinopathy and diabetic retinopathy (Liu J and Feener E P, *Biol. Chem.* 394(3), 319-28, 2013), proliferative and non-proliferative retinopathy (Liu J et al, *Invest. Ophthalmol. Vis. Sci.*, 54(2), 2013), CME following cataract extraction, CME induced by cryotherapy, CME induced by uveitis, CME following vascular occlusion (e.g., central retinal vein occlusion, branch retinal vein occlusion or hemiretinal vein occlusion), complications related to cataract surgery in diabetic retinopathy, hypertensive retinopathy (J A Phillips et al., *Hypertension*, 53, 175-181, 2009), retinal trauma, dry and wet age-related macular degeneration (AMD), ischemic reperfusion injuries (C Storoni et al., *JPET*, 381, 849-954, 2006), e.g., in a variety of contexts associated with tissue and/or organ transplantation.

Current treatments for angioedema, and those under development, target different elements in the HAE pathway. Three classes of therapies are currently available: (a) replacement therapy with C1INH concentrates (e.g., Cinryze, Berinert), (b) administration of selective kallikrein inhibitors (e.g., Ecallantide) and (c) bradykinin receptors antagonists (e.g., Firazyr).

Replacement therapies have proven useful for both acute attacks, including emergency situations, such as laryngeal edema (Bork K et al., *Transfusion*, 45, 1774-1784, 2005; Bork K and Barnstedt S E, *Arch. Intern. Med.*, 161, 714-718, 2001) and prophylaxis. Selective C1INH inhibitors inactivate both α-FXIIa and 1-FXIIa molecules active early in the HAE pathway that catalyze the production of kallikrein (Muller F and Renne T, *Curr. Opin. Hematol.*, 15, 516-21, 2008; Cugno M et al., *Trends Mol. Med.* 15(2):69-78, 2009). In addition to HAE, plasma kallikrein inhibitors are considered to be useful in the treatment of other edemas such as macular edema and brain edema, and retinopathy, e.g., retinopathy associated with diabetes and/or hypertension. There is evidence that plasma kallikrein inhibitors are also also effective in the treatment of edema formation in diseases, e.g., edema formation related to ischemic reperfusion injuries. The bradykinin receptors antagonists prevent bradykinin from activating the vascular permeability pathway and stop the initiation of swelling.

Methods of Treatment

Disclosed herein are methods of treating diseases or disorders wherein the inhibition of plasma kallikrein is indicated. Such diseases and disorders include but are not limited to angioedema, including hereditary and non-hereditary.

In some embodiments, the methods disclosed herein are useful for the treatment of angioedema. In some embodiments, the angioedema is hereditary angioedema (HAE). One embodiment provides a method of treating angioedema in a patient in need thereof comprising administration of a composition comprising a compound of Formula (I), or a pharmaceutically acceptable salt thereof. Another embodiment provides the method wherein the angioedema is hereditary angioedema.

In some embodiments, the methods disclosed herein are useful for the treatment of angioedema. In some embodiments, the angioedema is hereditary angioedema (HAE). One embodiment provides a method of treating angioedema in a patient in need thereof comprising administration of a composition comprising a compound of Formula (II), or a pharmaceutically acceptable salt thereof. Another embodiment provides the method wherein the angioedema is hereditary angioedema.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

The following abbreviations and terms have the indicated meanings throughout:

AcOH=acetic acid
$B_2pin_2$=bis(pinacolato)diboron
Boc=tert-butoxycarbonyl
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
kg or Kg=kilogram
L or l=liter
LC/MS=LCMS=liquid chromatography-mass spectrometry
LRMS=low resolution mass spectrometry
m/z=mass-to-charge ratio
Me=methyl MeOH=methanol
mg=milligram
min=minute
mL=milliliter
mmol=millimole
NaOAc=sodium acetate
PE=petroleum ether
Ph=phenyl
Prep=preparative
quant.=quantitative
RP-HPLC=reverse phase-high pressure liquid chromatography
rt or RT=room temperature
THF=tetrahydrofuran
UV=ultraviolet Example 20: Preparation of N-((3-aminobenzo[d]isoxazol-6-yl)methyl)-2-(3-(methylsulfonyl)-4-((2-oxopyridin-1(2H)-yl)methyl)benzyl)isonicotinamide

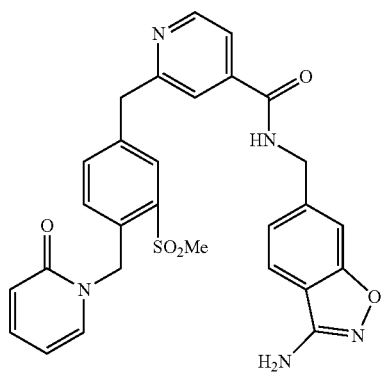 [SMILES: CS(=O)(=O)c1cc(Cc2cc(C(=O)NCc3ccc4c(N)noc4c3)ccn2)ccc1Cn1ccccc1=O]

Step 1: Preparation of tert-butyl {N-[(3-aminobenzo[d]isoxazol-6-yl)methyl](tert-butoxy)carbonylamino}formate

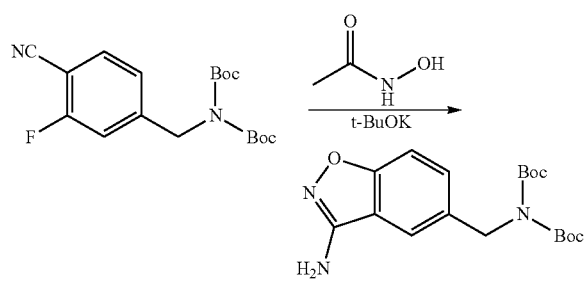

To a mixture of N-hydroxy-acetamide (964 mg, 12.86 mmol, 1.5 eq) in DMF (40 mL) was added t-BuOK (1.4 g, 12.86 mmol, 1.5 eq). After stirring for 30 min at rt, tert-butyl {(tert-butoxy)-N-[(4-cyano-3-fluorophenyl)methyl]carbonylamino}formate (3 g, 8.57 mmol, 1.0 eq) was added. The reaction mixture was stirred for 5 h at rt and then concentrated. The residue was purified by column chromatography on a silica gel (PE/EA=4/1 to 3/1, v/v) to give tert-butyl {N-[(3-aminobenzo[d]isoxazol-6-yl)methyl](tert-butoxy)carbonylamino}formate (2 g, 64%) as a white solid.

Step 2: Preparation of tert-butyl {N-[(3-aminobenzo[d]isoxazol-6-yl)methyl](tert-butoxy)carbonylamino}formate

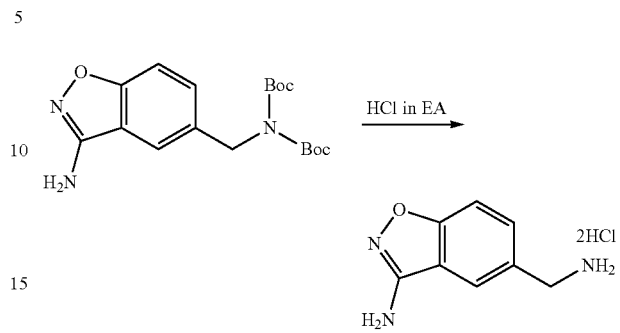

To a mixture of tert-butyl {N-[(3-aminobenzo[d]isoxazol-6-yl)methyl](tert-butoxy)carbonylamino}formate (2 g, 5.51 mmol, 1.0 eq) in MeOH (20 mL) was added 3 N of HCl in EA (5 mL). After stirring for 2 h at rt, the reaction mixture was filtered and the filter cake was washed with Et2O to give the crude 5-aminomethyl-benzo[d]isoxazol-3-ylamine dihydrochloride (1.5 g) as a white solid.

Step 3: Preparation of N-((3-aminobenzo[d]isoxazol-6-yl)methyl)-2-(3-(methylsulfonyl)-4-((2-oxopyridin-1(2H)-yl)methyl)benzyl)isonicotinamide

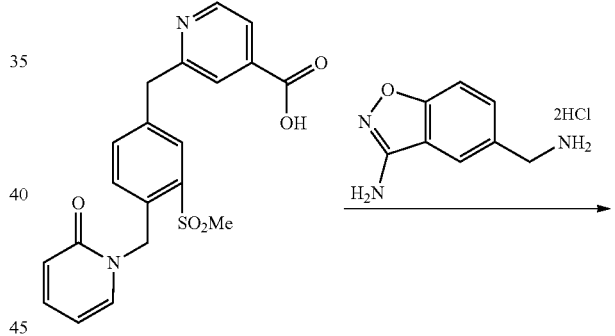

To a solution of 2-[3-methanesulfonyl-4-(2-oxo-2H-pyridin-1-ylmethyl)-benzyl]-isonicotinic acid (150 mg, crude) in DMF (15 mL) was added 5-aminomethyl-benzo[d]isoxazol-3-ylamine dihydrochloride (57 mg, 0.24 mmol, 1.0 eq) followed by EDCI (69 mg, 0.36 mmol, 1.5 eq), HOBT (49 mg, 0.36 mmol, 1.5 eq) and TEA (73 mg, 0.72 mmol, 3.0 eq). The reaction mixture was heated to 45° C. kept stirring for overnight. Water was added, and the mixture was extracted with DCM. The organic layer was washed with water, dried over Na$_2$SO$_4$, filtered, and concentrated. The residue was purified by prep-HPLC to give N-((3-aminobenzo[d]isoxazol-6-yl)methyl)-2-(3-(methylsulfonyl)-4-((2-oxopyridin-1(2H)-yl)methyl)benzyl)isonicotinamide (45 mg, 35%) as a white solid. LRMS (M+H+) m/z calculated 544.2, found 543.9. 1H NMR (DMSO-d6, 400 MHz) δ 9.40 (t, 1H), 8.63 (d, 1H), 7.91 (s, 1H), 7.87 (d, 1H), 7.78 (s, 1H), 7.76 (d, 1H), 7.66 (d, 1H), 7.59 (d, 1H), 7.53 (t, 1H), 7.35 (s, 1H), 7.21 (d, 1H), 6.83 (d, 1H), 6.44 (d, 1H), 6.33-6.38 (m, 3H), 5.43 (s, 2H), 4.59 (d, 2H), 4.25 (s, 2H), 3.40 (s, 3H).

Example 21: Preparation of N-((6-amino-2,4-dimethylpyridin-3-yl)methyl)-1-((3-chloroquinolin-6-yl)methyl)-6-oxo-1,6-dihydropyridine-3-carboxamide

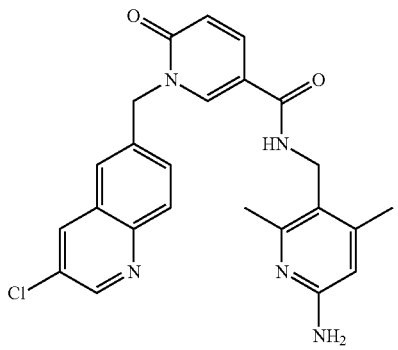 [SMILES: Cc1cc(N)nc(C)c1CNC(=O)c1ccc(=O)n(Cc2ccc3ncc(Cl)cc3c2)c1]

Step 1: Preparation of methyl 3-chloroquinoline-6-carboxylate

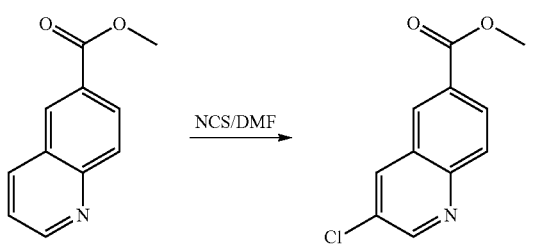

To a solution of methyl quinoline-6-carboxylate (15.0 g, 80.2 mmol, 1.0 eq) in DMF (200 ml) was added N-chlorosuccinimide (21.4 g, 0.16 mol, 2.0 eq) and the reaction mixture was stirred at 120° C. for 20 h. The reaction mixture was allowed to cool to rt, treated with brine and the mixture was extracted with EA. The organic layer was dried over Na$_2$SO$_4$, filtered and concentrated under vacuum. The crude product was purified by chromatography on silica gel (EA/PE=1/8, v/v) to afford methyl 3-chloroquinoline-6-carboxylate (9.1 g, 51%) as a yellow solid.

Step 1: Preparation of methyl 3-chloroquinoline-6-carboxylate

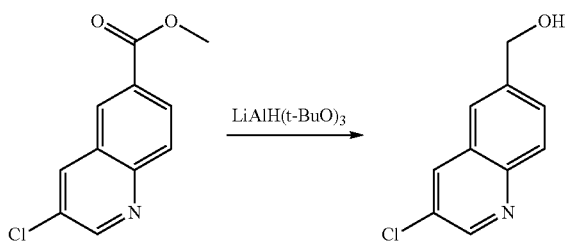

To a solution of methyl 3-chloroquinoline-6-carboxylate (9.0 g, 40.7 mmol, 1.0 eq) was added LiAlH(t-BuO)$_3$ (31.0 g, 0.122 mol, 3.0 eq). The resulting mixture was stirred at 40° C. for 12 h and then quenched by the addition of water, extracted with EA, the combined extracts were dried and concentrated. The residue was purified by silica gel chromatography (PE/EA=2/1, v/v) to afford (3-chloro-quinolin-6-yl)-methanol (5.9 g, 75%) as a white solid.

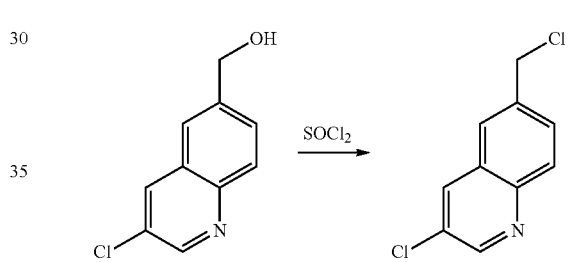

To (3-chloro-quinolin-6-yl)-methanol (3.3 g, 17.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to give 3-chloro-6-chloromethyl-quinoline (3.4 g, 94%) as a yellow solid.

Step 2: Preparation of 1-(3-chloro-quinolin-6-ylmethyl)-6-oxo-1,6-dihydro-pyridine-3-carboxylic Acid methyl ester

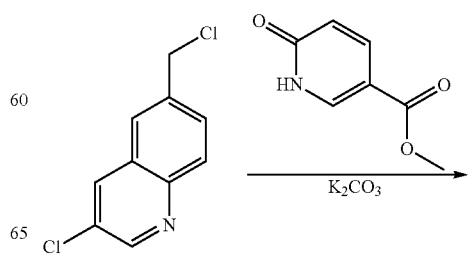

-continued

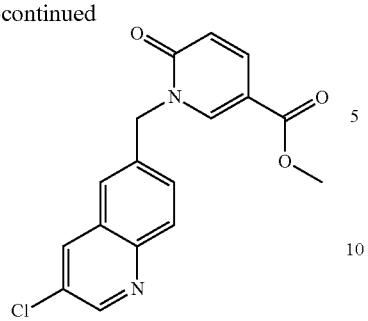

To a solution of 6-oxo-1,6-dihydro-pyridine-3-carboxylic acid methyl ester (216 mg, 1.42 mmol, 1 eq) in DMF (10 mL) was added $K_2CO_3$ (392 mg, 2.84 mmol, 2 eq), and the resulting mixture was stirred for 1 h at rt. 3-Chloro-6-chloromethyl-quinoline (300 mg, 1.42 mmol, 1 eq) was then added. The resulting mixture was stirred overnight at rt. The reaction mixture was diluted with brine (50 mL) and extracted with EA. The organic layer was washed with water, dried over $Na_2SO_4$, filtered, and concentrated. The resulting residue was purified by column chromatography on silica gel (PE/EA=4/1 to EA, v/v) to give 1-(3-chloro-quinolin-6-ylmethyl)-6-oxo-1,6-dihydro-pyridine-3-carboxylic acid methyl ester (270 mg, 60%) as a white solid.

Step 3: Preparation of 1-((3-chloroquinolin-6-yl)methyl)-6-oxo-1,6-dihydropyridine-3-carboxylic Acid

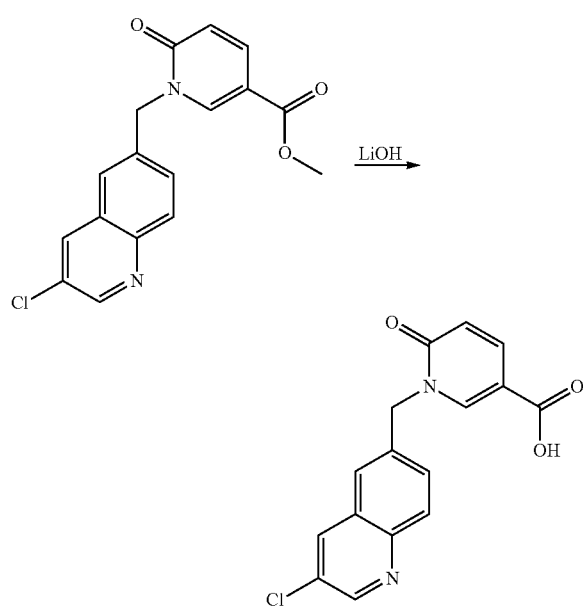

To a mixture of 1-(3-chloro-quinolin-6-ylmethyl)-6-oxo-1,6-dihydro-pyridine-3-carboxylic acid methyl ester (100 mg, 0.30 mmol, 1.0 eq) in THF/water (5 mL/5 mL) was added LiOH.H2O (38 mg, 0.91 mmol, 3 eq). The resulting mixture was stirred for 2 h. The organic solvent was removed. The reaction mixture was acidified to PH=5 by HCl (1 N), and then the mixture was concentrated to give the 1-((3-chloroquinolin-6-yl)methyl)-6-oxo-1,6-dihydropyridine-3-carboxylic acid (150 mg) as a yellow solid, which was used without further purification.

Step 4: Preparation of 5-iodo-4,6-dimethyl-pyridin-2-ylamine

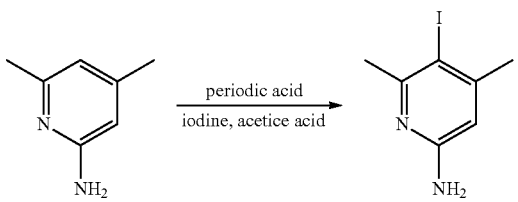

A mixture of 4,6-dimethyl-pyridin-2-ylamine (6 g, 49.1 mmol, 1.0 eq), periodic acid (1.6 g, 7.37 mmol, 0.15 eq) and iodine (6.2 g, 24.5 mmol, 0.5 eq) was added in a mixed solution of acetic acid (120 mL), $H_2O_2$ (6 mL) and $H_2SO_4$ (1 mL) at 80° C. for 4 h, then reaction mixture was poured into 10% aqueous $Na_2S_2O_3$ solution to quench any unrecalled iodine and extracted with ether. The extract was washed with 10% aqueous NaOH, dried over $Na_2SO_4$ and concentrated, the resulting residue was purified by silica gel chromatography (DCM/MeOH=100/1, v/v) to afford 5-iodo-4,6-dimethyl-pyridin-2-ylamine (10 g, 80%) as a yellow solid.

Step 5: Preparation of 6-amino-2,4-dimethyl-nicotinonitrile

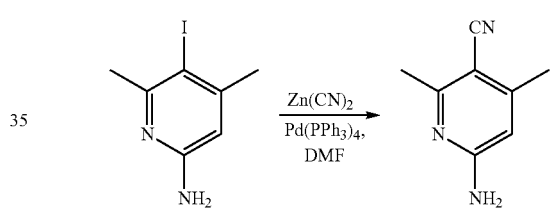

To a solution of 5-iodo-4,6-dimethyl-pyridin-2-ylamine (10 g, 40.3 mmol, 1.0 eq) in DMF (300 mL) was added $Zn(CN)_2$ (14 g, 120.9 mmol, 3.0 eq) and $Pd(PPh_3)_4$ (4.65 g, 4.03 mmol, 0.1 eq) carefully. The mixture was stirred at 90° C. overnight under $N_2$. EA and water was added. The organic layer was separated and concentrated. The resulting residue was purified by silica gel chromatography (DCM/MeOH=100/1, v/v) to afford 6-amino-2,4-dimethyl-nicotinonitrile (5 g, 84%) as a yellow solid.

Step 6: Preparation of tert-butyl (6-amino-2,4-dimethylpyridin-3-yl)methylcarbamate

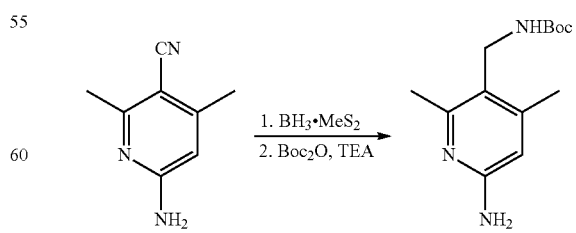

To a solution of 6-amino-2,4-dimethyl-nicotinonitrile (8.1 g, 55 mmol, 1.0 eq) in THF (300 mL) was added $BH_3$.$MeS_2$ (10 M, 55 mL, 550 mmol, 10.0 eq) at rt slowly. The mixture was stirred under reflux for 48 h. After cooling to rt, the mixture was quenched by the addition of concentrated HCl. The mixture was basified to pH 8 with sat. NaHCO₃ solution. To the mixture were added TEA (9.2 mL, 66 mmol, 1.2 eq) and Boc₂O (14.4 g, 66 mmol, 1.2 eq). The reaction mixture was stirred at rt for 1 h and then extracted with EA. The combined organic layers were dried over Na₂SO₄, filtered, and concentrated. The residue was purified on silica gel column (PE/EA=1/1) to give tert-butyl (6-amino-2,4-dimethylpyridin-3-yl)methylcarbamate (4.1 g, 30%) as a yellow solid.

Step 7: Preparation of 5-aminomethyl-4,6-dimethyl-pyridin-2-ylamine hydrochloride

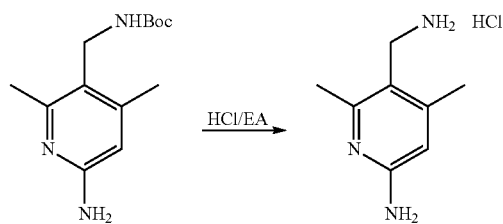

To a solution of tert-butyl (6-amino-2,4-dimethylpyridin-3-yl)methylcarbamate (4.1 g, 16.3 mmol, 1.0 eq) in EA (20 mL) was added a solution of HCl in EA (10 M, 50 mL). The mixture was stirred at rt for 1 h, and the precipitate was collected by filtration to afford 5-aminomethyl-4,6-dimethyl-pyridin-2-ylamine hydrochloride (2.0 g, 66%) as a white solid.

Step 8: Preparation of N-((6-amino-2,4-dimethylpyridin-3-yl)methyl)-1-((3-chloroquinolin-6-yl)methyl)-6-oxo-1,6-dihydropyridine-3-carboxamide

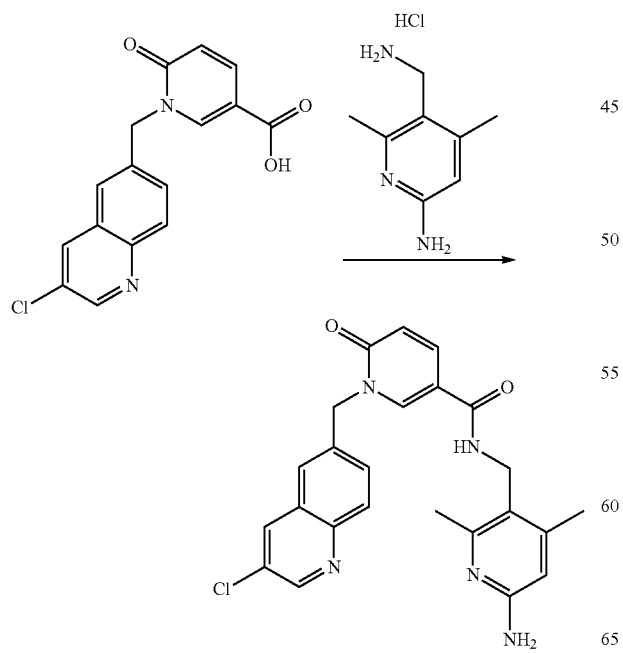

To a solution of 1-(3-chloro-quinolin-6-ylmethyl)-6-oxo-1,6-dihydro-pyridine-3-carboxylic acid (150 mg, crude) in DMF (15 mL) was added 5-aminomethyl-4,6-dimethyl-pyridin-2-ylamine hydrochloride (67 mg, 0.30 mmol, 1 eq) followed by EDCI (86 mg, 0.45 mmol, 1.5 eq), HOBT (61 mg, 0.45 mmol, 1.5 eq) and TEA (91 mg, 0.90 mmol, 3.0 eq). The reaction mixture was heated to 45° C. and kept stirring overnight. Water was added, and the mixture was extracted with DCM. The organic layer was washed with water, dried over Na₂SO₄, filtered, and concentrated. The residue was purified by prep-HPLC to give N-((6-amino-2,4-dimethylpyridin-3-yl)methyl)-1-((3-chloroquinolin-6-yl)methyl)-6-oxo-1,6-dihydropyridine-3-carboxamide (20 mg) as a white solid. LRMS (M+H) m/z calculated 448.2, found 448.0. ¹H NMR (DMSO-d₆, 400 MHz): δ 8.87 (s, 1H), 8.60 (s, 1H), 8.54 (s, 1H), 8.12 (t, 1H), 8.04 (d, 1H), 8.96 (d, 1H), 7.78 (s, 1H), 7.72 (d, 2H), 6.46 (d, 1H), 6.11 (s, 1H), 5.69 (br, 2H), 5.34 (s, 2H), 4.29 (d, 2H), 2.29 (s, 3H), 2.16 (s, 3H).

Example 22: Preparation of N-((6-amino-2,4-dimethylpyridin-3-yl)methyl)-5-((3-chloroquinolin-6-yl)methyl)nicotinamide

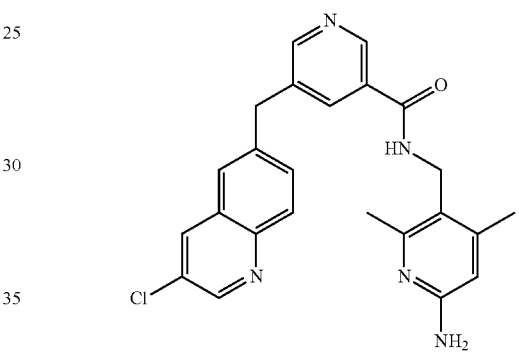

Step 1: Preparation of 5-((3-chloroquinolin-6-yl)methyl)nicotinic Acid

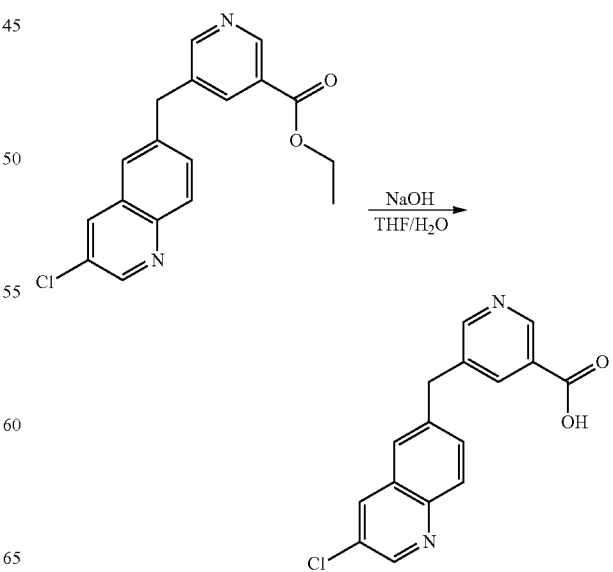

To a solution of 5-(3-chloro-quinolin-6-ylmethyl)-nicotinic acid ethyl ester (100 mg, 0.3 mmol, 1 eq) in THF/H₂O (10 mL/5 mL) was added NaOH (15 mg, 0.36 mmol, 1.2 eq). The mixture was stirred at rt for 3 h, and then aqueous HCl (2 N) was added to adjust pH to 4. The mixture was extracted with EA, and the organic layer was concentrated to provide the crude product (46 mg, 51%), which was used in the next step without further purification.

Step 2: Preparation of N-((6-amino-2,4-dimethylpyridin-3-yl)methyl)-5-((3-chloroquinolin-6-yl)methyl)nicotinamide

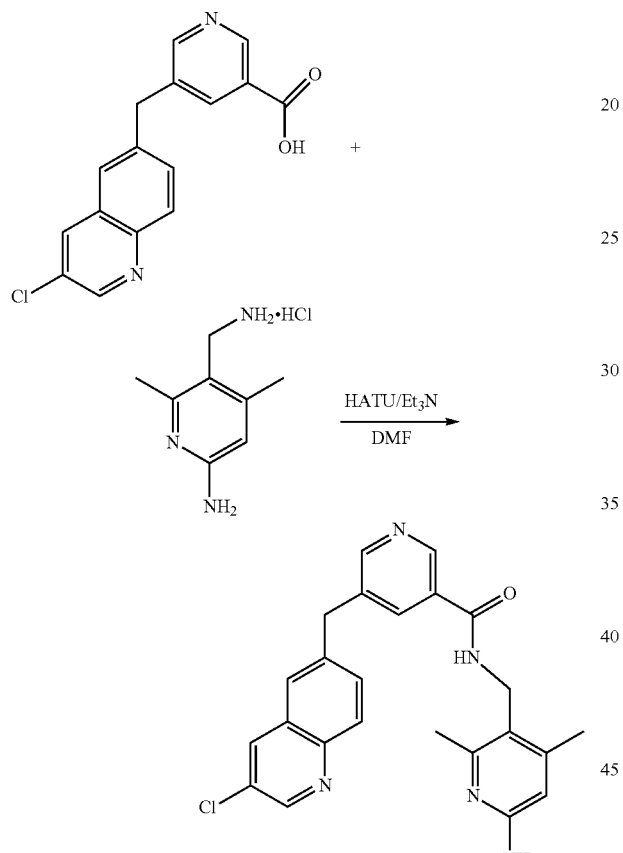

To a solution of 5-(3-chloro-quinolin-6-ylmethyl)-nicotinic acid (46 mg, 0.15 mmol, 1 eq) in DMF (10 mL) were added 5-aminomethyl-4,6-dimethyl-pyridin-2-ylamine (51 mg, 0.23 mmol, 1.5 eq), HATU (68.4 mg, 0.18 mmol, 1.2 eq), and Et₃N (45.4 mg, 0.45 mmol, 3 eq). The mixture was stirred at rt for 3 h. The reaction mixture was quenched with water, and extracted with DCM. The combined extracts were dried, concentrated, and the residue was purified by prep-HPLC to give N-((6-amino-2,4-dimethylpyridin-3-yl)methyl)-5-((3-chloroquinolin-6-yl)methyl)nicotinamide (16 mg, 25%) as a white solid. LRMS (M+H⁺) m/z calculated 432.1, found 431.8. 1H NMR (DMSO-d6, 400 MHz) δ 8.83-8.84 (m, 2H), 8.66 (s, 1H), 8.58 (s, 1H), 8.50 (s, 1H), 8.07 (s, 1H), 8.00-7.98 (s, 1H), 7.82 (s, 1H), 7.68-7.71 (m, 1H), 6.19 (s, 1H), 5.88 (s, 1H), 4.32 (d, 2H), 4.24 (s, 2H), 2.3 (s, 3H), 2.30 (s, 3H).

Example 23: N-((6-amino-2-methylpyridin-3-yl)methyl)-2-(3-(methylsulfonyl)-4-((2-oxopyridin-1(2H)-yl)methyl)benzyl)isonicotinamide

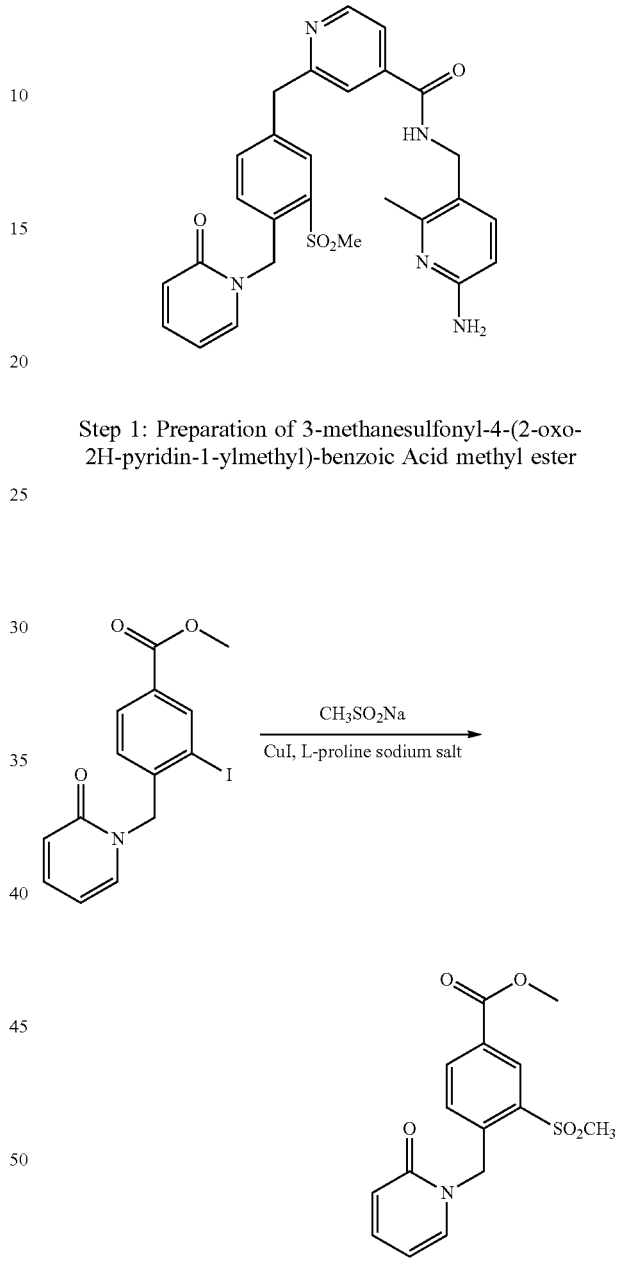

Step 1: Preparation of 3-methanesulfonyl-4-(2-oxo-2H-pyridin-1-ylmethyl)-benzoic Acid methyl ester To a solution of 3-iodo-4-(2-oxo-2H-pyridin-1-ylmethyl)-benzoic acid methyl ester (2.0 g, 5.42 mmol, 1 eq) in DMSO (10 mL) was added L-proline sodium salt (160 mg, 1.08 mmol, 0.2 eq), CuI (103 mg, 0.54 mmol, 0.1 eq) and CH₃SO₂Na (663 mg, 6.50 mmol, 1.2 eq). The mixture was stirred at 110° C. for 24 h. After cooling to rt the mixture was poured into water and the mixture was extracted with EA. The combined extracts were dried and concentrated. The residue was purified by column chromatography on silica gel (DCM/MeOH=100/1, v/v) to give 3-methanesulfonyl-4-(2-oxo-2H-pyridin-1-ylmethyl)-benzoic acid methyl ester (460 mg, 26%) as an off white solid.

Step 2: Preparation of 1-(4-hydroxymethyl-2-methanesulfonyl-benzyl)-1H-pyridin-2-one

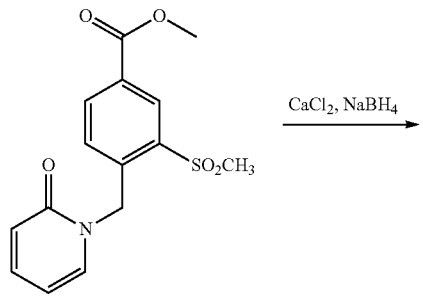

To a solution of 3-methanesulfonyl-4-(2-oxo-2H-pyridin-1-ylmethyl)-benzoic acid methyl ester (450 mg, 1.4 mmol, 1 eq) and CaCl₂ (154 mg, 1.4 mmol, 1 eq) in MeOH (15 mL) was added NaBH₄ (106 mg, 2.8 mmol, 2 eq) portionwise. The mixture was stirred at rt for 2 h and quenched by the addition of water. MeOH was removed by evaporation and the aqueous phase was extracted with EA. The combined extracts were dried and concentrated to give 1-(4-hydroxymethyl-2-methanesulfonyl-benzyl)-1H-pyridin-2-one (390 mg, 95%) as a white solid.

Step 3: Preparation of 1-(4-chloromethyl-2-methanesulfonyl-benzyl)-1H-pyridin-2-one

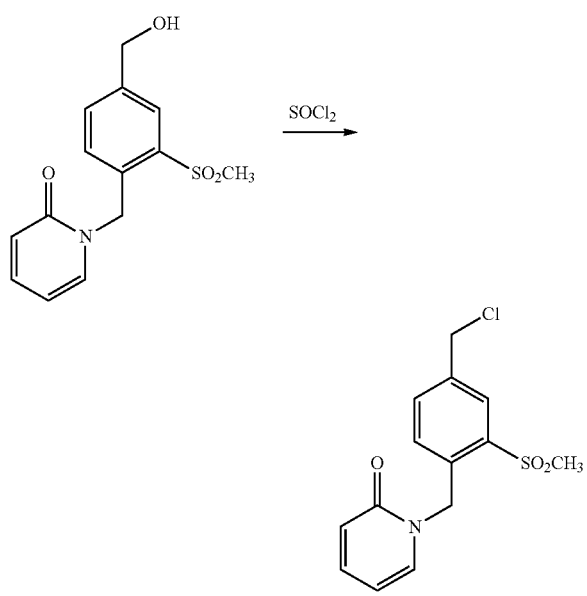

The mixture of 1-(4-hydroxymethyl-2-methanesulfonyl-benzyl)-1H-pyridin-2-one (390 mg, 1.33 mmol, 1 eq) and SOCl₂ (5 mL) was stirred at rt for 1 h. The volatiles were then removed at 40° C. in vacuum and the residue was dissolved in DCM. The mixture was washed with saturated aq. NaHCO₃, dried and concentrated to give 1-(4-chloromethyl-2-methanesulfonyl-benzyl)-1H-pyridin-2-one (390 mg, 94%) as a white solid.

Step 4: Preparation of 2-[3-methanesulfonyl-4-(2-oxo-2H-pyridin-1-ylmethyl)-benzyl]-isonicotinic Acid methyl ester

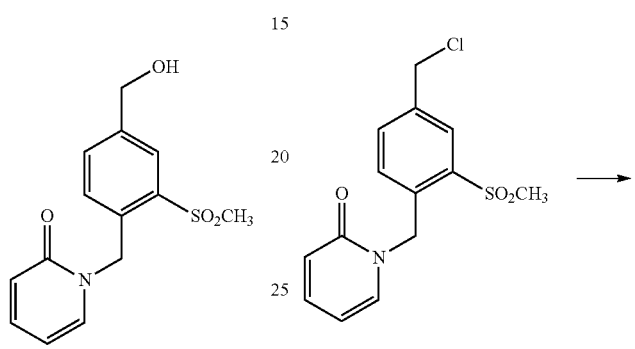

2-[3-Methanesulfonyl-4-(2-oxo-2H-pyridin-1-ylmethyl)-benzyl]-isonicotinic acid methyl ester (320 mg, 62%) was prepared as described in Example 24, Step 1 as a yellow solid.

Step 5: Preparation of 5-(aminomethyl)-6-methylpyridin-2-amine

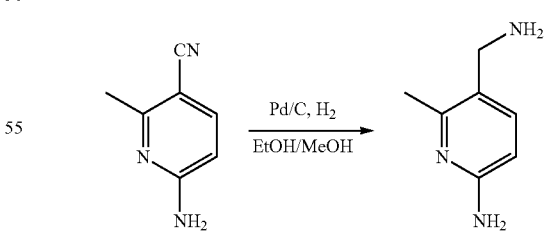

The mixture of 6-amino-2-methyl-nicotinonitrile (2 g, 15.0 mmol, 1.0 eq), Pd/C (10%, 500 mg) con. HCl (3 mL) in a solution of EtOH/MeOH (10 mL/10 mL) under H2 (50 psi) was stirred for overnight at rt. The reaction mixture was filtered, and the filtrate was concentrated to give crude 5-(aminomethyl)-6-methylpyridin-2-amine (3.5 g) as a yellow solid.

Step 6: Preparation of N-((6-amino-2-methylpyridin-3-yl)methyl)-2-(3-(methylsulfonyl)-4-((2-oxopyridin-1(2H)-yl)methyl)benzyl)isonicotinamide Example 24: Preparation of N-((6-amino-2,4-dimethylpyridin-3-yl)methyl)-2-((3-chloroquinolin-6-yl)methyl)pyrimidine-4-carboxamide

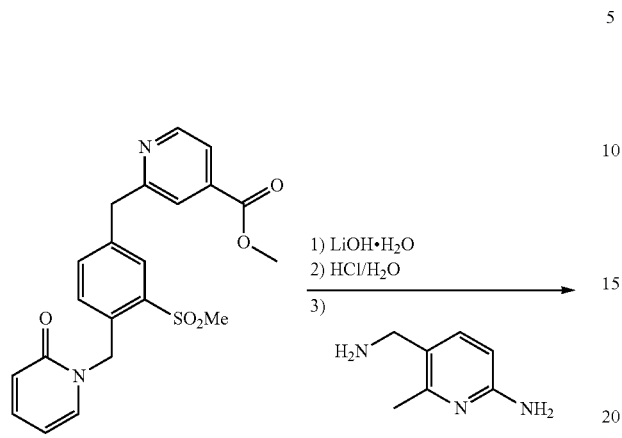

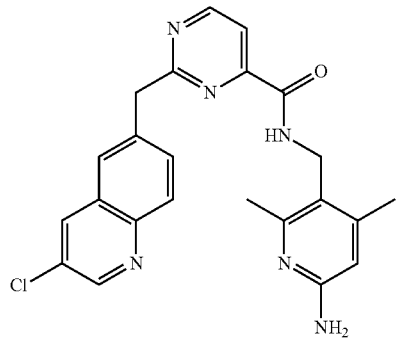

Step 1: Preparation of 2-(3-chloro-quinolin-6-ylmethyl)-pyrimidine-4-carboxylic acid methyl ester

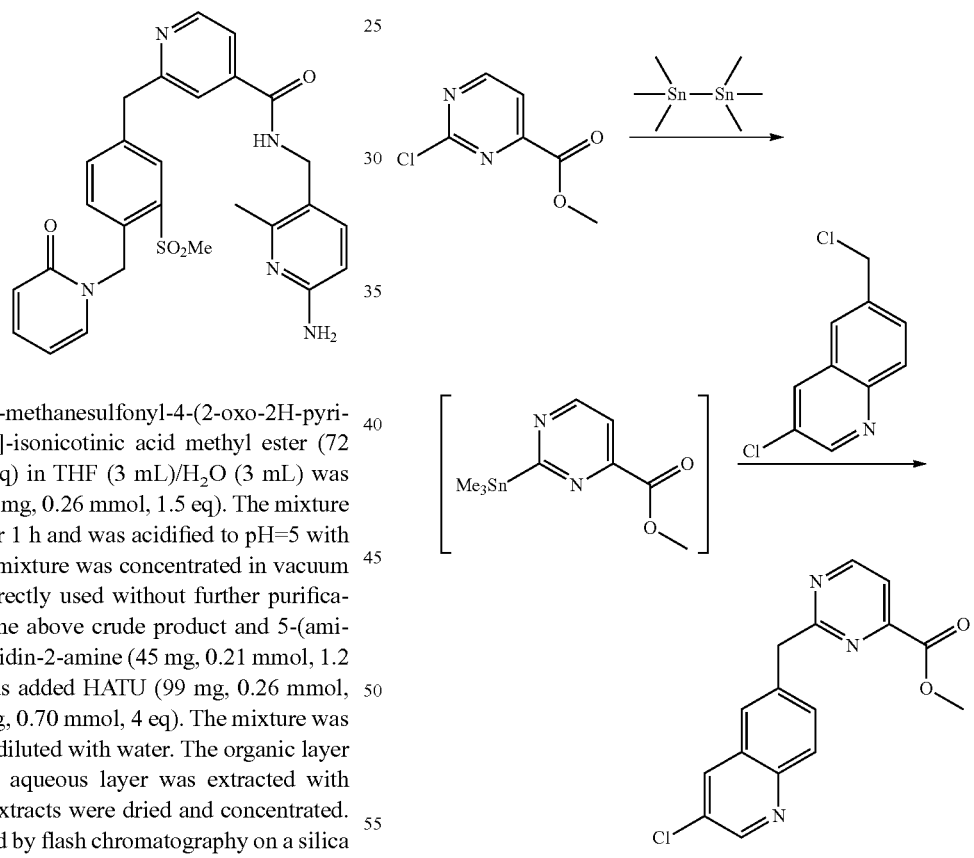

To a solution of 2-[3-methanesulfonyl-4-(2-oxo-2H-pyridin-1-ylmethyl)-benzyl]-isonicotinic acid methyl ester (72 mg, 0.175 mmol, 1.0 eq) in THF (3 mL)/H₂O (3 mL) was added LiOH—H₂O (11 mg, 0.26 mmol, 1.5 eq). The mixture was stirred at 40° C. for 1 h and was acidified to pH=5 with 1 N HCl solution. The mixture was concentrated in vacuum and the residue was directly used without further purification. To a solution of the above crude product and 5-(aminomethyl)-6-methylpyridin-2-amine (45 mg, 0.21 mmol, 1.2 eq) in DMF (5 mL) was added HATU (99 mg, 0.26 mmol, 1.2 eq) and Et₃N (71 mg, 0.70 mmol, 4 eq). The mixture was stirred at rt for 1 h and diluted with water. The organic layer was separated and the aqueous layer was extracted with DCM. The combined extracts were dried and concentrated. The residue was purified by flash chromatography on a silica gel column (DCM/MeOH=10/1, v/v) to give N-((6-amino-2-methylpyridin-3-yl)methyl)-2-(3-(methylsulfonyl)-4-((2-oxopyridin-1 (2H)-yl)methyl)benzyl)isonicotinamide (30 mg, 33% yields for 2 steps) as an off-white solid. LRMS (M+H+) m/z calculated 518.2, found 517.8. ¹H NMR (CD₃OD, 400 MHz) δ 8.46 (d, 1H), 7.87 (s, 1H), 7.68 (s, 1H), 7.67 (d, 1H), 7.57 (s, 1H), 7.49 (t, 1H), 7.47 (d, 1H), 7.40 (d, 1H), 6.86 (d, 1H), 6.47 (d, 1H), 6.35 (t, 1H), 6.33 (s, 1H), 5.44 (s, 2H), 4.32 (s, 2H), 4.14 (s, 2H), 3.24 (s, 3H), 2.14 (s, 3H).

To a solution of 3-chloro-6-chloromethyl-quinoline (1.12 g, 5.26 mmol, 1.0 eq) in dioxane (30 mL) was added 2-trimethylstannanyl-isonicotinic acid methyl ester (1.74 g, 5.79 mmol, 1.1 eq) and Pd(PPh₃)₂Cl₂ (372 mg, 0.53 mmol, 0.1 eq). The mixture was stirred at 90° C. for 3 h under nitrogen. The reaction mixture was concentrated, and the resulting residue was purified by silica gel chromatography (DCM/MeOH=100/1, v/v) to afford 2-(3-chloro-quinolin-6-ylmethyl)-pyrimidine-4-carboxylic acid methyl ester (250 mg, 15%) as a yellow solid.

Step 2: Preparation of N-((6-amino-2,4-dimethylpyridin-3-yl)methyl)-2-((3-chloroquinolin-6-yl)methyl)pyrimidine-4-carboxamide Step 1: Preparation of 6-(3-chloro-quinolin-6-ylmethyl)-pyrazine-2-carboxylic acid methyl ester

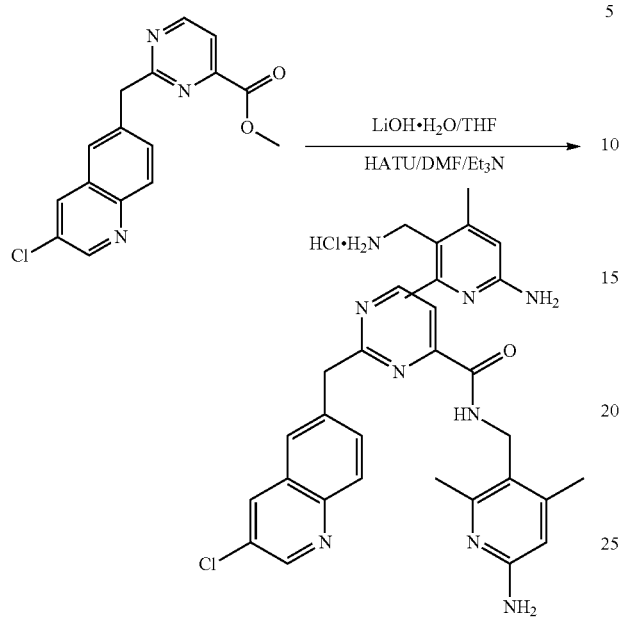

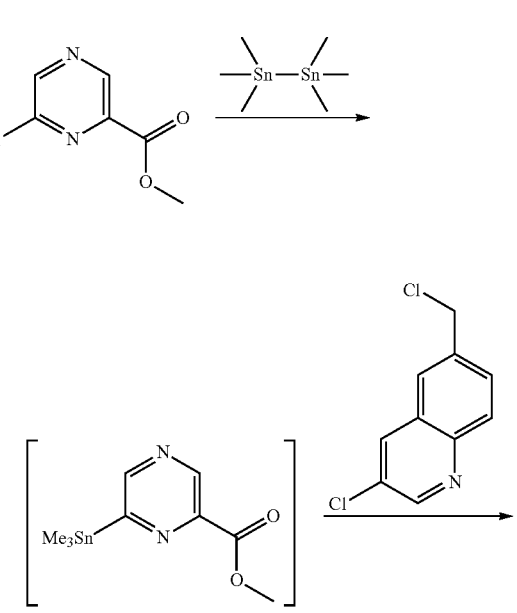

To a solution of 2-(3-chloro-quinolin-6-ylmethyl)-pyrimidine-4-carboxylic acid methyl ester (100 mg, 0.31 mmol, 1.0 eq) in THF (5 mL)/H₂ (5 mixture) was added LiOH H₂ (26.04 mg, 0.62 mmol, 2 eq). The mixture was stirred at 40° C. for 1 h, and acidified to pH 5 with 1 N HCl solution. The mixture was concentrated in vacuo, and the resulting residue was used without further purification. To a solution of the above crude product in DMF (20 mL) was added 5-aminomethyl-4,6-dimethyl-pyridin-2-ylamine (92 mg, 0.41 mmol, 1.3 eq), HATU (157 mg, 0.41 mmol, 1.3 eq), and Et₃N (0.5 mL). The mixture was stirred at rt overnight. The reaction mixture was quenched with water and extracted with DCM. The combined extracts were dried and concentrated. The resulting residue was purified by Prep-HPLC to give N-((6-amino-2,4-dimethylpyridin-3-yl)methyl)-2-((3-chloroquinolin-6-yl)methyl)pyrimidine-4-carboxamide (5 mg, 3.7%) as a gray solid. LRMS (M+H⁺) m/z calculated 433.1, found 433.0. H NMR (CDCl₃, 400 MHz) δ 8.92 (s, 1H), 8.78 (s, 1H), 7.95-8.05 (m, 3H), 7.64-7.71 (m, 3H), 6.21 (s, 1H), 4.43-4.53 (m, 6H), 2.40 (s, 3H), 2.18 (s, 3H).

6-(3-Chloro-quinolin-6-ylmethyl)-pyrazine-2-carboxylic acid methyl ester (50 mg, 5.5%) was prepared as described for 2-(3-chloro-quinolin-6-ylmethyl)-pyrimidine-4-carboxylic acid methyl ester (Example 24).

Step 2: Preparation of N-((6-amino-2,4-dimethylpyridin-3-yl)methyl)-2-((3-chloroquinolin-6-yl)methyl)pyrimidine-4-carboxamide Example 25: Preparation of N-((6-amino-2,4-dimethylpyridin-3-yl)methyl)-6-((3-chloroquinolin-6-yl)methyl)pyrazine-2-carboxamide

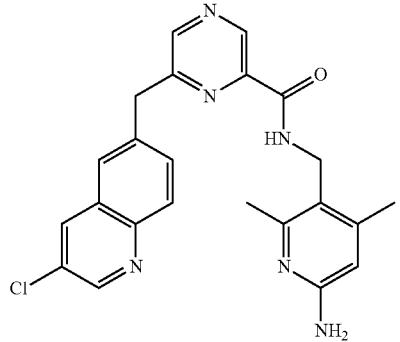 [SMILES: Cc1cc(N)nc(C)c1CNC(=O)c1cncc(Cc2ccc3ncc(Cl)cc3c2)n1]

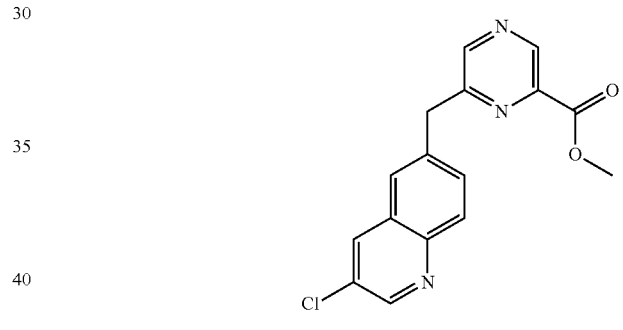

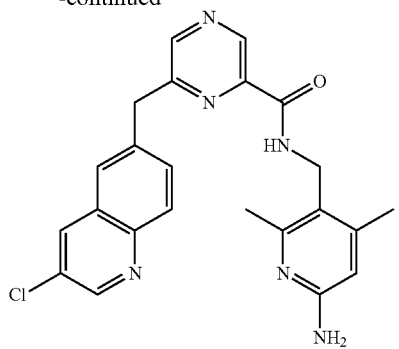

N-((6-amino-2,4-dimethylpyridin-3-yl)methyl)-6-((3-chloroquinolin-6-yl)methyl)pyrazine-2-carboxamide (28 mg, 12.9%) was prepared as described for N-((6-amino-2,4-dimethylpyridin-3-yl)methyl)-2-((3-chloroquinolin-6-yl)methyl)pyrimidine-4-carboxamide as a gray solid. LRMS (M+H⁺) m/z calculated 433.1, found 433.1. ¹H NMR (CDCl₃, 400 MHz) δ 9.02 (s, 1H), 8.85 (s, 2H), 8.47 (m, 2H), 7.96-7.98 (d, 2H), 7.87 (s, 1H), 7.78 (d, 1H), 6.10 (s, 1H), 5.71 (s, 2H), 4.44 (s, 2H), 4.38-4.40 (d, 2H), 2.28 (s, 3H), 2.15 (s, 3H).

Example 26: Preparation of N-((6-amino-2-(trifluoromethyl)pyridin-3-yl)methyl)-2-(3-(methylsulfonyl)-4-((2-oxopyridin-1(2H)-yl)methyl)benzyl)isonicotinamide

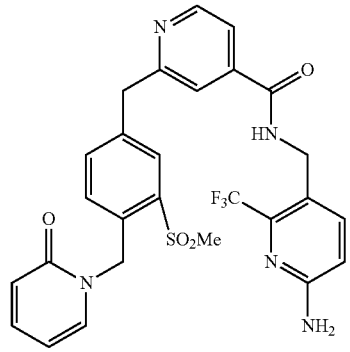 [SMILES: CS(=O)(=O)c1cc(Cc2cc(C(=O)NCc3ccc(N)nc3C(F)(F)F)ccn2)ccc1Cn1ccccc1=O]

Step 1: Preparation of 5-bromo-6-trifluoromethyl-pyridin-2-ylamine

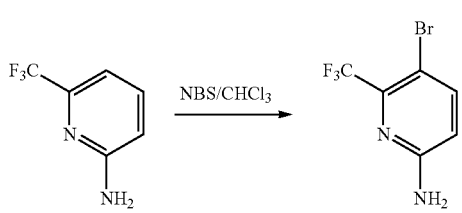 [SMILES: Nc1cccc(C(F)(F)F)n1 ; Nc1ccc(Br)c(C(F)(F)F)n1]

To a solution of 6-trifluoromethyl-pyridin-2-ylamine (10.0 g, 62.1 mmol, 1 eq) in CHCl₃ (200 mL) was added NBS (12.0 g, 67.4 mmol, 1.08 eq). The solution was stirred in the dark for 2 h, at which time it was added to DCM (200 mL) and 1 N NaOH (200 mL). Upon mixing, the layers were separated and the organic layer was dried and concentrated. The residue was purified by silica gel column (EA/PE=1/1, v/v) to give 5-bromo-6-trifluoromethyl-pyridin-2-ylamine (6.5 g, 44%) as an orange solid.

Step 2: Preparation of 6-amino-2-trifluoromethyl-nicotinonitrile

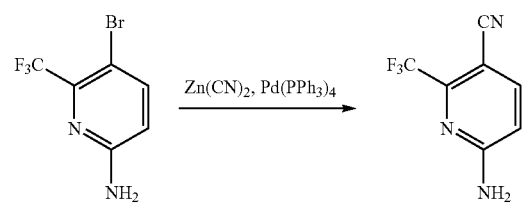 [SMILES: Nc1ccc(Br)c(C(F)(F)F)n1 ; N#Cc1ccc(N)nc1C(F)(F)F]

To a solution of 5-bromo-6-trifluoromethyl-pyridin-2-ylamine (6.5 g, 27.08 mmol, 1 eq) in DMF (70 mL) was added Zn(CN)₂ (6.3 g, 54.16 mmol, 2 eq) and Pd(PPh₃)₄ (3.1 g, 2.71 mmol, 0.1 eq). The mixture was stirred at 100° C. for 3 h and then cooled to rt. The precipitate was filtered off and the filtrate was concentrated. The residue was purified by flash chromatography on a silica gel column (PE/EA=1/1, v/v) to give 6-amino-2-trifluoromethyl-nicotinonitrile (1.9 g, 38%) as a yellow solid.

Step 3: Preparation of tert-butyl (6-amino-2-(trifluoromethyl)pyridin-3-yl)methylcarbamate

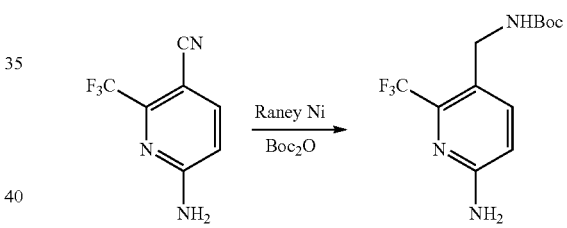

To a solution of 6-amino-2-trifluoromethyl-nicotinonitrile (1.5 g, 8.02 mmol, 1 eq) in MeOH (40 mL) was added Raney Ni (500 mg), Et₃N (1.62 g, 16.04 mmol, 2 eq) and Boc₂O (3.50 g, 16.04 mmol, 2 eq). The mixture was stirred at rt overnight under hydrogen atmosphere. Raney Ni was filtered off and the filtrate was concentrated in vacuum. The residue was purified by flash chromatography on a silica gel column (PE/EA=1/1, v/v) to give tert-butyl (6-amino-2-(trifluoromethyl)pyridin-3-yl)methylcarbamate (2.1 g, 90%) as a yellow solid.

Step 4: Preparation of tert-butyl (6-amino-2-(trifluoromethyl)pyridin-3-yl)methylcarbamate

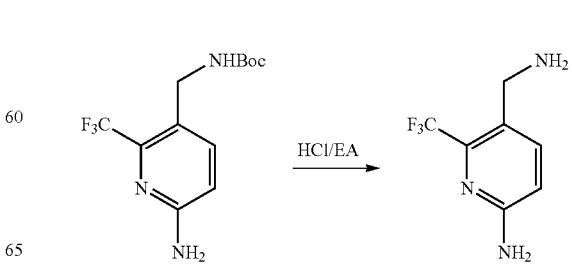

To a solution of tert-butyl (6-amino-2-(trifluoromethyl)pyridin-3-yl)methylcarbamate (2.1 g, 7.2 mmol, 1 eq) in EA (10 mL) was added HCl/EA solution. The mixture was stirred at rt for 1 h. The precipitate was collected by filtration to give 5-aminomethyl-6-trifluoromethyl-pyridin-2-ylamine hydrochloride (1.7 g, 89%) as a white solid.

Step 5: Preparation of N-((6-amino-4-methylpyridin-3-yl)methyl)-2-(3-(methylsulfonyl)-4-((2-oxopyridin-1(2H)-yl)methyl)benzyl)isonicotinamide

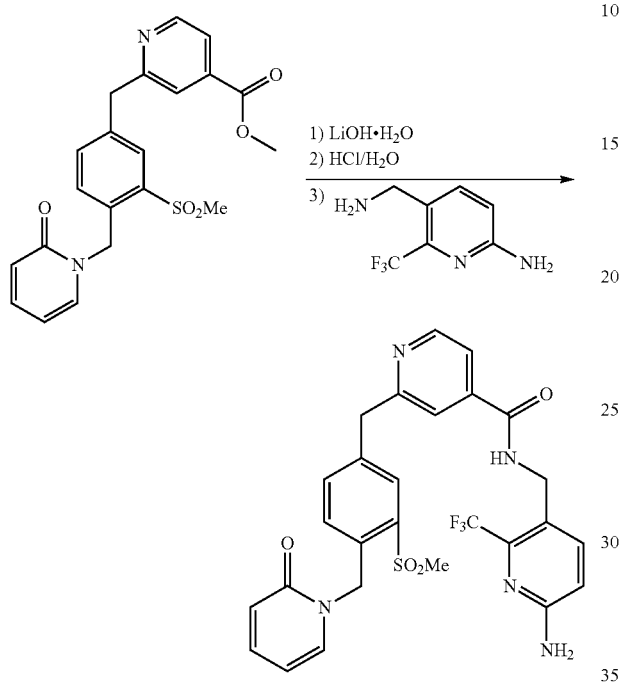

N-((6-amino-2-(trifluoromethyl) pyridin-3-yl)methyl)-2-(3-(methylsulfonyl)-4-((2-oxopyridin-1(2H)-yl)methyl)benzyl)isonicotinamide (30 mg, 30% yields for 2 steps) was prepared as described for N-((6-amino-4-methylpyridin-3-yl)methyl)-2-(3-(methylsulfonyl)-4-((2-oxopyridin-1 (2H)-yl)methyl)benzyl)isonicotinamide as a white solid. LRMS (M+H$^+$) m/z calculated 572.2, found 571.8. $^1$H NMR (CD$_3$OD, 400 MHz) δ 8.60 (d, 1H), 8.00 (d, 1H), 7.81 (d, 1H), 7.71 (s, 1H), 7.65-7.59 (m, 3H), 7.55 (d, 1H), 6.98 (d, 1H), 6.73 (d, 1H), 6.60 (d, 1H), 6.49 (t, 1H), 5.57 (s, 2H), 4.58 (s, 2H), 4.29 (s, 2H), 3.32 (s, 3H).

Example 27: Preparation of N-((6-amino-4-(trifluoromethyl)pyridin-3-yl)methyl)-2-(3-(methylsulfonyl)-4-((2-oxopyridin-1(2H)-yl)methyl)benzyl)isonicotinamide

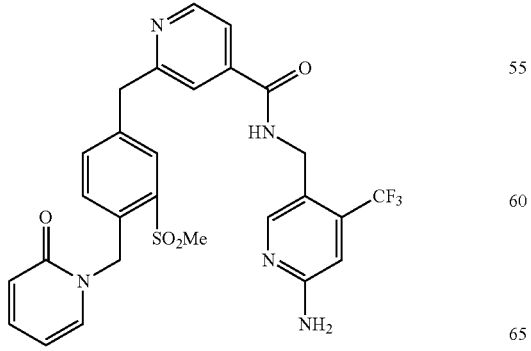

N-((6-amino-4-(trifluoromethyl)pyridin-3-yl)methyl)-2-(3-(methylsulfonyl)-4-((2-oxopyridin-1(2H)-yl)methyl)benzyl)isonicotinamide (22 mg, 22% yields for 2 steps) was prepared as described for N-((6-amino-4-methylpyridin-3-yl)methyl)-2-(3-(methylsulfonyl)-4-((2-oxopyridin-1 (2H)-yl)methyl)benzyl)isonicotinamide (Example 26) as a white solid. LRMS (M+H$^+$) m/z calculated 572.2, found 571.8.
$^1$H NMR (CD$_3$OD, 400 MHz) δ 8.49 (d, 1H), 7.98 (s, 1H), 7.89 (s, 1H), 7.69 (d, 1H), 7.58 (s, 1H), 7.50 (t, 1H), 7.43 (d, 1H), 6.87 (d, 1H), 6.74 (s, 1H), 6.49 (d, 1H), 6.38 (t, 1H), 5.47 (s, 2H), 4.46 (s, 2H), 4.18 (s, 2H), 3.22 (s, 3H).

Example 28: Preparation of N-((6-amino-2-methylpyridin-3-yl)methyl)-2-(3-(methylsulfonyl)-4-((2-oxopyridin-1(2H)-yl)methyl)benzyl)isonicotinamide

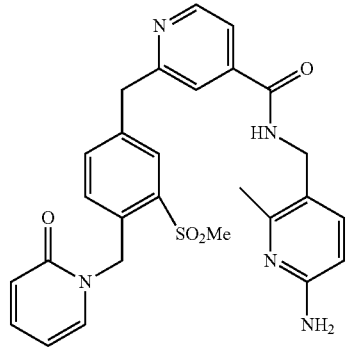 [SMILES: Cc1nc(N)ccc1CNC(=O)c1ccnc(Cc2ccc(Cn3ccccc3=O)c(S(C)(=O)=O)c2)c1]

N-((6-amino-2-methylpyridin-3-yl)methyl)-2-(3-(methylsulfonyl)-4-((2-oxopyridin-1(2H)-yl)methyl)benzyl)isonicotinamide (20 mg, 23% yield for 2 steps) was prepared as described for N-((6-amino-4-methylpyridin-3-yl)methyl)-2-(3-(methylsulfonyl)-4-((2-oxopyridin-1 (2H)-yl)methyl)benzyl)isonicotinamide (Example 26) as an off-white solid. LRMS (M+H$^+$) m/z calculated 518.1, found 517.8. $^1$H NMR (DMSO-d$_6$, 400 MHz) δ 9.00 (s, 1H), 8.62 (d, 1H), 7.91 (s, 1H), 7.88 (d, 1H), 7.75 (s, 1H), 7.62-7.53 (m, 3H), 7.26 (d, 1H), 6.85 (d, 1H), 6.46 (d, 1H), 6.35 (t, 1H), 6.25 (d, 1H), 5.76 (s, 2H), 5.44 (s, 2H), 4.30 (d, 1H), 4.24 (s, 2H), 3.42 (s, 3H), 2.28 (s, 3H).

Example 29: Preparation of N-((3-chloro-1H-indol-5-yl)methyl)-2-(3-(methylsulfonyl)-4-((2-oxopyridin-1(2H)-yl)methyl)benzyl)isonicotinamide

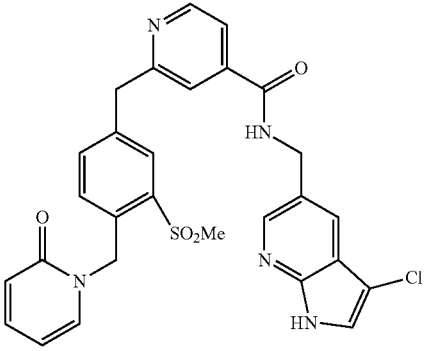 [SMILES: CS(=O)(=O)c1cc(Cc2cc(C(=O)NCc3cnc4[nH]cc(Cl)c4c3)ccn2)ccc1Cn1ccccc1=O]

N-((3-chloro-1H-indol-5-yl)methyl)-2-(3-(methylsulfonyl)-4-((2-oxopyridin-1(2H)-yl)methyl)benzyl)isonicotinamide (20 mg, 21% yield for 2 steps) was prepared as described for N-((6-amino-4-methylpyridin-3-yl)methyl)-2-(3-(methylsulfonyl)-4-((2-oxopyridin-1(2H)-yl)methyl)benzyl)isonicotinamide (Example 26) as an off-white solid. LRMS (M+H$^+$) m/z calculated 562.1, found 562.1. $^1$H NMR (DMSO-d$_6$, 400 MHz): δ 11.98 (s, 1H), 9.36 (t, 1H), 8.65 (d, 1H), 8.31 (s, 1H), 7.90-7.78 (m, 4H), 7.68-7.52 (m, 4H), 6.64 (d, 1H), 6.45 (d, 1H), 6.34 (t, 1H), 5.43 (s, 2H), 4.60 (d, 2H), 4.25 (s, 2H), 3.50 (s, 3H).

Example 30: Preparation of N-((5-chloro-1H-indazol-3-yl)methyl)-2-(3-(methylsulfonyl)-4-((2-oxopyridin-1(2H)-yl)methyl)benzyl)isonicotinamide

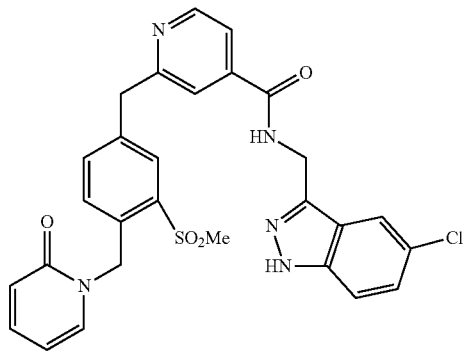 [SMILES: CS(=O)(=O)c1cc(Cc2cc(C(=O)NCc3n[nH]c4ccc(Cl)cc34)ccn2)ccc1Cn1ccccc1=O]

N-((5-chloro-1H-indazol-3-yl)methyl)-2-(3-(methylsulfonyl)-4-((2-oxopyridin-1(2H)-yl)methyl)benzyl)isonicotinamide (20 mg, 20% yield for 2 steps) was prepared as described for N-((6-amino-4-methylpyridin-3-yl)methyl)-2-(3-(methylsulfonyl)-4-((2-oxopyridin-1(2H)-yl)methyl)benzyl)isonicotinamide (Example 26) as an off-white solid. LRMS (M+H$^+$) m/z calculated 562.1, found 561.8. $^1$H NMR (DMSO-d$_6$, 300 MHz): δ 9.42 (t, 1H), 8.64 (d, 1H), 7.93-7.80 (m, 4H), 7.67 (d, 1H), 7.58-7.53 (m, 3H), 7.35 (dd, 1H), 6.83 (d, 1H), 6.45 (d, 1H), 6.34 (t, 1H), 5.43 (s, 2H), 4.79 (d, 2H), 4.25 (s, 2H), 3.39 (s, 2H).

II. Biological Evaluation

Example 1: In Vitro Enzyme Inhibition

The ability of the compounds disclosed herein to inhibit human plasma kallikrein activity was quantified according to the procedures below.

A 10 mM solution of the test compound was made in DMSO. This solution was serially diluted 1:5 in DMSO to yield 2000, 400, 80, 16, 3.2, 0.64, 0.128, 0.0256 and 0.00512 µM compound test solutions. A control tube containing only DMSO is included. 16 µL of each compound test solution was combined with 384 µL of assay buffer (50 mM Tris-HCl pH 7.5, 150 mM NaCl, 0.01% Triton X-100) to yield a "4× test compound buffer stock".

Separately, a 40 nM solution of human Plasma Kallikrein (Abcam) and a 93.6 µM solution Pro-Phe-Arg-AMC (Bachem) were made using assay buffer. These solutions are hereby refereed to as 4×hPK and 2×PFR-AMC, respectively.

60 µL of each 4× test compound buffer stock was combined with 60 µL of 4× hPK to yield 120 µL of "2× test compound buffer stock/2×hPK". 50 µL was removed from this mixture and placed into duplicate wells on a Microfluor 1 Black U-bottom microtiter plate (Thermo Scientific). This plate was incubated for 5 minutes at 37° C. To each well, 50 µL of pre-warmed 2×PFR-AMC was added to start the enzymatic reaction. Cleavage of PFR-AMC was monitored in a Biotek Synergy H4 reader set at 37° C. Readings are taken every 43 seconds for 1 hour. The highest mean velocity over 20 reads (~15 minutes) is used to calculate the IC$_{50}$. The IC$_{50}$ is calculated using the Gen5 (Biotek Instruments).

The ability of the compounds in Table 1 to inhibit human plasma kallikrein activity was determined and the data is shown in Table 3.

TABLE 3

| Chemical Synthesis Example | Name | hPK IC50 (µM) |
| --- | --- | --- |
| 1 | N-((5-chloro-1H-indazol-3-yl)methyl)-5-(2-(trifluoromethyl)benzyl)nicotinamide | C |
| 2 | N-((5-chloro-1H-indazol-3-yl)methyl)-5-(4-cyanobenzyl)nicotinamide | C |
| 3 | N-((5-chloro-1H-indazol-3-yl)methyl)-5-(4-(trifluoromethyl)benzyl)nicotinamide | C |
| 4 | N-((5-chloro-1H-indazol-3-yl)methyl)-5-(4-methylbenzyl)nicotinamide | C |
| 5 | 5-benzyl-N-((5-chloro-1H-indazol-3-yl)methyl)nicotinamide | C |
| 6 | 5-(2-carbamoylbenzyl)-N-((5-chloro-1H-indazol-3-yl)methyl)nicotinamide | C |
| 7 | N-((3-chloro-6-fluoro-1H-indol-5-yl)methyl)-5-((4-cyano-1H-pyrazol-1-yl)methyl)nicotinamide | C |
| 8 | 5-((4-carbamoyl-1H-pyrazol-1-yl)methyl)-N-((3-chloro-6-fluoro-1H-indol-5-yl)methyl)nicotinamide | D |
| 9 | N-((3-chloro-6-fluoro-1H-indol-5-yl)methyl)-2-((3-((N-cyclopropylacetamido)methyl)-1H-pyrazol-1-yl)methyl)isonicotinamide | D |
| 10 | N-((5-chloro-1H-indazol-3-yl)methyl)-6-(methyl(4-((2-oxopyridin-1(2H)-yl)methyl)phenyl)amino)picolinamide | D |
| 11 | N-(2-amino-1-(5-chloro-1H-indazol-3-yl)-2-oxoethyl)-5-(4-((2-oxopyridin-1(2H)-yl)methyl)benzyl)nicotinamide | C |
| 12 | 2-(5-chloro-1H-indazol-3-yl)-2-(5-(4-((2-oxopyridin-1(2H)-yl)methyl)benzyl)nicotinamido)acetic acid | C |
| 13 | N-((5-chloro-1H-indazol-3-yl)methyl)-3-(1-(4-((2-oxopyridin-1(2H)-yl)methyl)phenyl)vinyl)benzamide | C |
| 14 | N-(4-carbamoylbenzyl)-5-(4-((2-oxopyridin-1(2H)-yl)methyl)benzyl)nicotinamide | C |
| 15 | N-(4-chlorobenzyl)-5-(4-((2-oxopyridin-1(2H)-yl)methyl)benzyl)nicotinamide | C |
| 16 | N-(4-methoxybenzyl)-5-(4-((2-oxopyridin-1(2H)-yl)methyl)benzyl)nicotinamide | C |
| 17 | N-((3-chloro-6-fluoro-1H-indol-5-yl)methyl)-6-oxo-1-((3-((2-oxopyridin-1(2H)-yl)methyl)bicyclo[1.1.1]pentan-1-yl)methyl)-1,6-dihydropyridine-3-carboxamide | C |
| 18 | N-(4-bromo-3-fluorobenzyl)-2-(4-((2-oxopyridin-1(2H)-yl)methyl)benzyl)isonicotinamide | D |
| 19 | N-(4-cyano-2-methylbenzyl)-2-(4-((2-oxopyridin-1(2H)-yl)methyl)benzyl)isonicotinamide | D |
| 20 | N-((3-aminobenzo[d]isoxazol-6-yl)methyl)-2-(3-(methylsulfonyl)-4-((2-oxopyridin-1(2H)-yl)methyl)benzyl)isonicotinamide | B |
| 21 | N-((6-amino-2,4-dimethylpyridin-3-yl)methyl)-1-((3-chloroquinolin-6-yl)methyl)-6-oxo-1,6-dihydropyridine-3-carboxamide | A |
| 22 | N-((6-amino-2,4-dimethylpyridin-3-yl)methyl)-5-((3-chloroquinolin-6-yl)methyl)nicotinamide | A |
| 23 | N-((6-amino-2-methylpyridin-3-yl)methyl)-2-(3-(methylsulfonyl)-4-((2-oxopyridin-1(2H)-yl)methyl)benzyl)isonicotinamide | A |
| 24 | N-((6-amino-2,4-dimethylpyridin-3-yl)methyl)-2-((3-chloroquinolin-6-yl)methyl)pyrimidine-4-carboxamide | A |
| 25 | N-((6-amino-2,4-dimethylpyridin-3-yl)methyl)-6-((3-chloroquinolin-6-yl)methyl)pyrazine-2-carboxamide | A |

TABLE 3-continued

| Chemical Synthesis Example | Name | hPK IC50 (µM) |
|---|---|---|
| 26 | N-((6-amino-2-(trifluoromethyl)pyridin-3-yl)methyl)-2-(3-(methylsulfonyl)-4-((2-oxopyridin-1(2H)-yl)methyl)benzyl)isonicotinamide | C |
| 27 | N-((6-amino-4-(trifluoromethyl)pyridin-3-yl)methyl)-2-(3-(methylsulfonyl)-4-((2-oxopyridin-1(2H)-yl)methyl)benzyl)isonicotinamide | B |
| 28 | N-((6-amino-2-methylpyridin-3-yl)methyl)-2-(3-(methylsulfonyl)-4-((2-oxopyridin-1(2H)-yl)methyl)benzyl)isonicotinamide | A |
| 29 | N-((3-chloro-1H-indol-5-yl)methyl)-2-(3-(methylsulfonyl)-4-((2-oxopyridin-1(2H)-yl)methyl)benzyl)isonicotinamide | A |
| 30 | N-((5-chloro-1H-indazol-3-yl)methyl)-2-(3-(methylsulfonyl)-4-((2-oxopyridin-1(2H)-yl)methyl)benzyl)isonicotinamide | A |

Note:
Biochemical assay $IC_{50}$ data are designated within the following ranges:
A: ≤0.10 µM
B: >0.10 µM to ≤1.0 µM
C: >1.0 µM to ≤10 µM
D: >10 µM

Example 2: In Vitro Cellular Assay

The ability of the compounds disclosed herein to inhibit cellular kallikrein activity was quantified and the respective $EC_{50}$ value was determined.

Materials:

Plasma kallikrein inhibitor C1NH (Athens Research & Technology, Cat #16-16-031509); Ellagic acid (Sigma, E2250); Substrate Z—FR-2-AMC (GL Biochem, Cat #55352); Nunc™ 96-Well Polypropylene MicroWell™ Plates (Nunc, Cat #267342)

Methods:

All dilutions were prepared in an assay buffer comprising 50 mM Tris-HCl pH 7.2, 150 mM NaCl, and 0.01% Triton X-100.

Four fold serial dilutions were prepared from a 107.53 µM plasma kallikrein inhibitor C1NH stock solution, to yield ten solutions with concentrations between 20 µM and 0.76 nM. Similarly, four fold serial dilutions were prepared from 10 mM stock solutions of various test compounds, to yield ten solutions with concentrations between 4 mM and 0.015 µM. The ten solutions of the test compounds, prepared by serial dilution, were further diluted 50-fold in the assay buffer.

Human plasma is thawed on ice and centrifuged for 15 min at 4° C. to remove platelets. A 1 mM stock solution of ellagic acid is diluted to 8 µM and mixed with human plasma, after removing platelets, at a ratio of 1:0.8. The mixture of human plasma and ellagic acid was further diluted 32-fold in the assay buffer, to yield the final mixture for use in the inhibition assay.

A 22.5 µL volume of the final mixture of human plasma and ellagic acid was added to a 96-well microwell plate and the plate was incubated for 15 min at 37° C.

The C1NH inhibitor at various concentrations, prepared by serial dilutions as described above, were added to the inhibitor control wells. The volume of C1NH inhibitor added to each inhibitor control well was 12.5 µL, to yield final concentrations of 5 µM, 1.25 µM, 312.5 nM, 78.125 nM, 19.531 nM, 4.883 nM, 1.221 nM, 0.305 nM, 0.076 nM, and 0.019 nM. Each C1NH concentration is tested in duplicates.

The test compounds at various concentrations, also prepared by serial dilutions as described above, are added to the test wells. The volume of test compound added to each test well was 12.5 µL, to yield final concentrations of 20 µM, 5 µM, 1.25 µM, 312.5 nM, 78.125 nM, 19.531 nM, 4.883 nM, 1.221 nM, 0.305 nM, and 0.076 nM. Each test compound concentration was tested in duplicates.

In addition to the inhibitor control and test wells, the 96 well assay plate includes positive control wells which contained the mixture of human plasma and ellagic acid without C1NH inhibitor or test compounds, and background wells which contained neither the mixture of human plasma and ellagic acid nor the test compounds. The total volume of liquid in positive control and background wells was brought up to 35 µL, using the assay buffer.

The assay plate containing C1NH inhibitors and test compounds mixed with human plasma and ellagic acid and appropriate controls was incubated at 37° C. for 5 min. A 10 mM stock solution of substrate Z—FR-2-AMC was diluted to 133.2 µM in the assay buffer, and 15 µL of the diluted substrate was added to each well, to yield a final substrate concentration of 40 µM in each well. The reagents were mixed well by shaking the plate gently for 30 sec.

The enzyme reaction was quantified by immediate kinetic reading of the assay plate using excitation/emission wavelengths of 330 nm/440 nm respectively. Fluorescence intensity was recorded for 60 min, using a time interval of 43 sec.

The inhibition activity of the test compounds were evaluated using the IC50 values, calculated according to the dose-response curve of the test compounds, fitted using the "log(inhibitor)-response(variable slope)" equation in GraphPadPrism software (GraphPad Software, Inc.).

The percentage inhibition was calculated using the following equation:

$$\text{Inhibition \%} = 100 - \frac{\text{Sample value} - \text{Mean}(BG)}{\text{Mean}(PC) - \text{Mean}(BG)} \times 100$$

where, Mean(BG) is the average value of the fluorescence intensity of the background wells and Mean(PC) is the average value of the fluorescence intensity of the positive control wells. Table 4 provides the $EC_{50}$ values of various compounds disclosed herein.

TABLE 4

| Chemical Synthesis Example | Name | Contact Assay EC50 (µM) |
|---|---|---|
| 21 | N-((6-amino-2,4-dimethylpyridin-3-yl)methyl)-1-((3-chloroquinolin-6-yl)methyl)-6-oxo-1,6-dihydropyridine-3-carboxamide | A |
| 22 | N-((6-amino-2,4-dimethylpyridin-3-yl)methyl)-5-((3-chloroquinolin-6-yl)methyl)nicotinamide | A |
| 23 | N-((6-amino-2-methylpyridin-3-yl)methyl)-2-(3-(methylsulfonyl)-4-((2-oxopyridin-1(2H)-yl)methyl)benzyl)isonicotinamide | A |
| 25 | N-((6-amino-2,4-dimethylpyridin-3-yl)methyl)-6-((3-chloroquinolin-6-yl)methyl)pyrazine-2-carboxamide | A |
| 29 | N-((3-chloro-1H-indol-5-yl)methyl)-2-(3-(methylsulfonyl)-4-((2-oxopyridin-1(2H)-yl)methyl)benzyl)isonicotinamide | A |

Note:
Contact assay $EC_{50}$ data are designated within the following ranges:
A: ≤0.10 µM
B: >0.10 µM to ≤1.0 µM
C: >1.0 µM to ≤10 µM
D: >10 µM III. Preparation of Pharmaceutical Dosage Forms Example 1: Oral Tablet A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a pharmaceutically acceptable salt thereof, selected from:
   N-((6-amino-2,4-dimethylpyridin-3-yl)methyl)-2-((3-chloroquinolin-6-yl)methyl)pyrimidine-4-carboxamide;
   N-((6-amino-2-methylpyridin-3-yl)methyl)-2-((3-chloroquinolin-6-yl)methyl)pyrimidine-4-carboxamide;
   N-((3-chloro-1H-pyrrolo[2,3-b]pyridin-5-yl)methyl)-2-((3-chloroquinolin-6-yl)methyl)pyrimidine-4-carboxamide;
   N-((3-chloro-6-fluoro-1H-indol-5-yl)methyl)-2-((3-chloroquinolin-6-yl)methyl)pyrimidine-4-carboxamide;
   N-((5-chloro-1H-indazol-3-yl)methyl)-2-((3-chloroquinolin-6-yl)methyl)pyrimidine-4-carboxamide;
   N-((6-amino-2,4-dimethylpyridin-3-yl)methyl)-2-((3-methylquinolin-6-yl)methyl)pyrimidine-4-carboxamide;
   N-((3-chloro-1H-pyrrolo[2,3-b]pyridin-5-yl)methyl)-2-((3-methylquinolin-6-yl)methyl)pyrimidine-4-carboxamide;
   N-((6-amino-2-methylpyridin-3-yl)methyl)-2-((3-methylquinolin-6-yl)methyl)pyrimidine-4-carboxamide;
   N-((5-chloro-1H-indazol-3-yl)methyl)-2-((3-methylquinolin-6-yl)methyl)pyrimidine-4-carboxamide;
   N-((3-chloro-6-fluoro-1H-indol-5-yl)methyl)-2-((3-methylquinolin-6-yl)methyl)pyrimidine-4-carboxamide;
   N-((6-amino-2,4-dimethylpyridin-3-yl)methyl)-2-((6-chloroquinolin-3-yl)methyl)pyrimidine-4-carboxamide;
   N-((3-chloro-1H-pyrrolo[2,3-b]pyridin-5-yl)methyl)-2-((6-chloroquinolin-3-yl)methyl)pyrimidine-4-carboxamide;
   N-((6-amino-2-methylpyridin-3-yl)methyl)-2-((6-chloroquinolin-3-yl)methyl)pyrimidine-4-carboxamide;
   N-((5-chloro-1H-indazol-3-yl)methyl)-2-((6-chloroquinolin-3-yl)methyl)pyrimidine-4-carboxamide; and
   N-((3-chloro-6-fluoro-1H-indol-5-yl)methyl)-2-((6-chloroquinolin-3-yl)methyl)pyrimidine-4-carboxamide.

2. A pharmaceutical composition comprising a compound of claim 1, or a pharmaceutically acceptable salt thereof, and a pharmaceutically acceptable excipient.

* * * * *